US011261234B2

(12) United States Patent
Xiao et al.

(10) Patent No.: US 11,261,234 B2
(45) Date of Patent: Mar. 1, 2022

(54) MUTANT FACTOR VIII COMPOSITIONS AND METHODS

(71) Applicant: IVYGEN CORPORATION, Fort Washington, PA (US)

(72) Inventors: Weidong Xiao, Fort Washington, PA (US); Wenjing Cao, Ardmore, PA (US); Biao Dong, Philadelphia, PA (US)

(73) Assignee: IVYGEN CORPORATION, Fort Washington, PA (US)

( * ) Notice: Subject to any disclaimer, the term of this patent is extended or adjusted under 35 U.S.C. 154(b) by 0 days.

(21) Appl. No.: 16/164,208

(22) Filed: Oct. 18, 2018

(65) Prior Publication Data

US 2019/0177399 A1 Jun. 13, 2019

Related U.S. Application Data

(63) Continuation of application No. 14/893,878, filed as application No. PCT/US2014/043777 on Jun. 24, 2014, now abandoned.

(60) Provisional application No. 61/838,867, filed on Jun. 24, 2013.

(51) Int. Cl.
C07K 14/755 (2006.01)
A61K 38/00 (2006.01)

(52) U.S. Cl.
CPC ............ *C07K 14/755* (2013.01); *A61K 38/00* (2013.01)

(58) Field of Classification Search
CPC .............................. C07K 14/755; A61K 38/00
See application file for complete search history.

(56) References Cited

U.S. PATENT DOCUMENTS

| | | | |
|---|---|---|---|
| 4,501,729 A | 2/1985 | Boucher et al. | |
| 5,364,771 A | 11/1994 | Lollar et al. | |
| 5,478,745 A | 12/1995 | Samulski et al. | |
| 6,491,907 B1 | 12/2002 | Rabinowitz et al. | |
| 6,759,216 B1 | 7/2004 | Lollar | |
| 7,855,274 B2 | 12/2010 | Fay et al. | |
| 8,519,111 B2 | 8/2013 | Lollar | |
| 2004/0029106 A1 | 2/2004 | Samulski et al. | |
| 2004/0092442 A1 | 5/2004 | Kaufman et al. | |
| 2004/0197875 A1 | 10/2004 | Hauser et al. | |
| 2005/0100990 A1* | 5/2005 | Saenko | C07K 14/755 435/69.6 |
| 2007/0265199 A1 | 11/2007 | Fay et al. | |
| 2011/0286988 A1 | 11/2011 | Jiang et al. | |
| 2012/0065136 A1 | 3/2012 | Fay | |
| 2013/0183280 A1 | 7/2013 | Oestergaard et al. | |

FOREIGN PATENT DOCUMENTS

WO 2003/31598 † 4/2003

OTHER PUBLICATIONS

Siner et al., Blood, 121(21): 4396-4403, May 23, 2013.*
Alignment of SEQ ID No. 1 with SEQ ID No. 1 of US 2005/100990, pp. 1-13.*
CHAMP (CDC Hemophilia Mutation Project) accessed online at www.cdc.gov/ncbddd/hemophilia/champs.html. On Jun. 19, 2018.
Doering et al., "Directed Engineering of a High-Expression Chimeric Transgene as a Strategy for Gene Therapy of Hemophilia A", Molecular Therapy, pp. 1-10, online publication Mar. 3, 2009.
Doering et al., "Identification of Porcine Coagulation Factor VIII Domains Responsible for High Level Expression via Enhanced Secretion", The Journal of Biological Chemistry (2004), vol. 279, No. 8, Issue of Feb. 20, pp. 6546-6552, published Dec. 1, 2003.
Doering et al., "High Level Expression of Recombinant Porcine Coagulation Factor VIII", The Journal of Biological Chemistry (2002), vol. 277, No. 41, Issue of Oct. 11, pp. 38345-38349.
European Search Report dated Nov. 13, 2017 issued in EP 14817835.3.
First Office Action issued in CN201480035965.2.
First Search Documents Report issued in CN2014800359652.
Liu et al., British Journal of Haematology (1998), vol. 103: pp. 1051-1060.
Margaglione et al., Haematologica (2008), vol. 93(5): pp. 722-728.
Ravanbod et al., Haemophilia (2012), e340-e346.
Reiter et al., Thrombosis and Haemostasis (2010), vol. 104: pp. 78-85.
Supplemental Search Report dated Nov. 2, 2017 issued in EP 14817835.
Third Party Observation Report issued in Publication No. 7635763; Publication Date: Dec. 22, 2009.
Wakabayashi et al., Journal of Biological Chemistry, 286(29): 25748-25755, 2011.
Wakabayashi et al., Identification of Residues Contributing to A2 Domain-dependent Structural Stability in Factor VIII and Factor VIIIa, J. Biol. Chem. 2008, 283(17); pp. 11645-11651.
Connelly, et al., Blood, vol. 91, No. 9 (1998), pp. 3273-3281.
Sarkar, et al., Blood, vol. 103, No. 4 (2004), pp. 1253-1260.
Altschul, et al., 1990, J Mol Biol 215:403-410.
Amano, et al. "Mutation at Either Arg336 or Arg562 in Factor VIII is Insufficient for Complete Resistance to Activated Protein C (APC)-Mediated Inactivation: implications for the APC Resistance Test," Thrombosis & Haemostasis 79(3):557-63 (1998).
Gale, et al., "An Engineered Interdomain Disulfide Bond Stabilizes Human Blood Coagulation Factor VIIIa," J. Thrombosis and Haemostasis 1(9): 1966-1971 (2003).

(Continued)

Primary Examiner — Thaian N. Ton
(74) Attorney, Agent, or Firm — Troutman Pepper Hamilton Sanders LLP

(57) ABSTRACT

In one aspect, present invention provides a recombinant mutant human factor VIII having increased expression and/or secretion as compared to wild-type factor VIII. In certain embodiments, the recombinant factor VIII includes one or more amino acid substitution(s) selected from the group consisting of I86, Y105, A108, D115, Q117, F129, G132, H134, M147 and L152. In other aspects, the present invention provides FVIII encoding nucleic acids, FVIII-expression vectors, as well as methods of using the modified FVIII genes in the treatment of FVIII deficiencies, such as hemophilia A.

16 Claims, 15 Drawing Sheets

Specification includes a Sequence Listing.

(56) References Cited

OTHER PUBLICATIONS

Fay, et al., "Factor VIIIa A2 Subunit Residues 558-565 Represent a Factor IXa Interactive Site," J. Biol. Chem. 269(32):20522-7 (1994).
Bajaj, et al., "Factor IXa: Factor VIIIa Interaction. Helix 330-338 of Factor IXa Interacts with Residues 558-565 and Spatially Adjacent Regions of the A2 Subunit of Factor VIIIa," J. Biol. Chem. 276(19):16302-9 (2001).
Lenting, et al., "The Sequence Glu1811-Lys1818 of Human Blood Coagulation Factor VIII Comprises a Binding Site for Activated Factor IX," J. Biol. Chem. 271(4):1935-40 (1996).
Lapan, et al., "Localization of a Factor X Interactive Site in the A1 Subunit of Factor VIIIa," J. Biol. Chem. 272:2082-88 (1997).
Swaroop, et al., "Mutagenesis of a Potential Immunoglobulin-Binding Protein-Binding Site Enhances Secretion of Coagulation Factor VIII," J. Biol. Chem. 272(39):24121-4 (1997).
Sarafanov, et al., "Cell Surface Heparan Sulfate Proteoglycans Participate in Factor VIII Catabolism Mediated by Low Density Lipoprotein Receptor-Related Protein," J. Biol. Chem. 276(15):11970-9 (2001).
Saenko, et al., "Role of the Low Density Lipoprotein-Related Protein Receptor in Mediation of Factor VIII Catabolism," J. Biol. Chem. 274(53):37685-92 (1999).
Saenko, et al., "The Future of Recombinant Coagulation Factors," J. Thrombosis and Haemostasis 1:922-930 (2003).
Roth, et al., New Engl. J. Med. 344:1735-1742 (2001).
Gnatenko, et al., Br. J. Haematol. 104:27-36 (1999).
Lusher, et al., New Engl. J. Med. 328:453-459 (1993).
Pittman, et al., Blood 79:389-397 (1992).
Brinkhous, et al., Proc. Natl. Acad. Sci. 82:8752-8755 (1985).
Kardar et al., Iranian Journal of Biotechnology, vol. 8, No. 3, pp. 139-149 (2010).
Castaman, et al., Haemophilia, vol. 13, No. 3, pp. 311-316 (2007).
International Search Report of International Application No. PCT/US2014/043777 dated Nov. 3, 2014.
International Preliminary Report on Patentability and Written Opinion of International Application No. PCT/US2014/043777 dated Jan. 7, 2016.
Office Action dated Jan. 6, 2020 in connection with Chinese Application No. 201480035965.2.
Parker Ernest T., et al., "A1 Subunit-mediated Regulation of Thrombin-activated Factor VIII A2 Subunit Dissociation", The Journal of Biological Chemistry, May 19, 2006, vol. 281, No. 20, pp. 13922-13930.
Office Action dated Jun. 2, 2020 in connection with Chinese Application No. 201480035965.2.
Kardar GA, et.al., "The effects of novel mutations in A1 domain of human coagulation factor VIII on its secretion level in cultured mammalian cells", Iranian Journal of Biotechnology, vol. 8, No. 3, Jul. 31, 2010.
Parker, The Journal of Biological Chemistry, vol. 281, pp. 13922-13930, Mar. 2, 2006, USA.†

\* cited by examiner
† cited by third party

```
hF8        1   ATRRYYLGAV ELSWDYMQSD LGELPVDARF PPRVPKSFPF NTSVVYKKTL SEQ ID NO 7
hF8-x10        ATRRYYLGAV ELSWDYMQSD LGELPVDARF PPRVPKSFPF NTSVVYKKTL SEQ ID NO 8 hF8        51  FVEFTDHLFN IAKPRPPWMG LLGPTIQAEV YDTVVITLKN MASHPVSLHA
hF8-x10        FVEFTDHLFN IAKPRPPWMG LLGPTIQAEV YDTVVTLKN MASHPVSLHA
                                                        * hF8        101 VGVSYWKASE GAEYDDQTSQ REKEDDKVFP GGSHTYVWQV LKENGPMASD
hF8-x10        VGVSFWKSSE GAEYEDHTSQ REKEDDKVLP GKSQTYVWQV LKENGPTASD
                    *  *        *  *            *   *           * hF8        151 PLCLTYSYLS HVDLVKDLNS GLIGALLVCR EGSLAKEKTQ TLHKFILLFA
hF8-x10        PPCLTYSYLS HVDLVKDLNS GLIGALLVCR EGSLAKEKTQ TLRKFILLFA
                *                                            *
```

FIG. 2

```
                1                                                              50
hF8     ATRRYYLGAV ELSWDYMQSD LGELPVDARF PRRVPKSFPF NTSVVYKKTL SEQ ID NO: 7
hF8-x5  ATRRYYLGAV ELSWDYMQSD LGELPVDARF PRRVPKSFPF NTSVVYKKTL SEQ ID NO: 9

51                                                             100
hF8     FVEFTDHLFN IAKPRPPWMG LLGPTIQAEV YDTVVITLKN MASHPVSLHA
hF8-x5  FVEFTDHLFN IAKPRPPWMG LLGPTIQAEV YDTVVYTLAN MASHPVSLHA
                                                  *

101                                                            150
hF8     VGVSYWKASE GAEYDDQTSQ REKEDDKVFP GGSHTYVWQV LKENGEMASD
hF8-x5  VGVSYWKSSE GAETDDQTSQ REKEDDKVFP GKSHTYVWQV LKENGETASD
                    *              *                 *          *

151                                                            200
hF8     PLCLTYSYLS HVDLVKDLNS GLIGALLVCR EGSLAKEKTQ TLHKFILLFA
hF8-x5  PPCLTYSYLS HVDLVKDLNS GLIGALLVCR EGSLAKEKTQ TLHKFILLPA
          *                                                  *
```

FIG. 3

| Human factor VIII amino acids | Exemplary substitutions with enhanced secretion |
|---|---|
| I86 | V,L,M |
| Y105 | F,W |
| A108 | S,G,T,P |
| D115 | E,N,H,Q,R,K |
| Q117 | H,N,E,D,R,K |
| F129 | L,V,I,M,P,T,K |
| G132 | K,E,D,R,T,M,N,S,W |
| H134 | O,G,Y,N,E,D,R,K |
| M147 | T,A,G,S,P |
| L152 | P,S,G,T |

| Substitutions of amino acids hBDD-F8-X10 | Exemplary substitutions with enhanced secretion |
| --- | --- |
| hBDD-F8-X10-V86I | 80 |
| hBDD-F8-X10-S108A | 71 |
| hBDD-F8-X10-E115D | 89 |
| hBDD-F8-X10-H117Q | 88 |
| hBDD-F8-X10-L129F | 77 |
| hBDD-F8-X10-K132G | 55 |
| hBDD-F8-X10-T147M | 75 |
| hBDD-F8-X10-P152L | 63 |
| hBDD-F8-X10-6p | 42 |
| hBDD-F8-X10 | 100 |

FIG. 9

MUTANT FACTOR VIII COMPOSITIONS AND METHODS

This application is a continuation application of U.S. application Ser. No. 14/893,878, filed Nov. 24, 2015, which is a National Stage Application of International Application PCT/US2014/043777, filed Jun. 24, 2014, which claims priority to U.S. Provisional Patent Application No. 61/838,867, filed on Jun. 24, 2013. The entirety of the aforementioned applications are incorporated herein by reference.

GOVERNMENT LICENSE RIGHTS

This invention was made with U.S. government support under grant HL084381 awarded by the National Institutes of Health. The U.S. government thus may have certain license rights in this invention.

SEQUENCE LISTING

This application contains a Sequence Listing which has been submitted in ASCII format via EFS-Web and is hereby incorporated by reference herein in its entirety. The ASCII text file was created on Sep. 13, 2018, is named Sequence.txt and is 81,419 bytes in size.

FIELD

The present invention relates to recombinant human factor VIII mutants exhibiting higher expression levels than the corresponding wild-type human factor VIII. The present invention also relates to methods of making and using the recombinant human factor VIII mutants.

BACKGROUND

Hemophilia A, the most common of the severe, inherited bleeding disorders, results from a deficiency or defect in the plasma protein factor VIII. In patients with Hemophilia A, the blood does not clot properly resulting in excessive bleeding when the hemophiliac is injured. Treatment consists of replacement therapy using preparations of (purified) plasma or the recombinant protein. Blood clotting begins when platelets adhere to the cut wall of an injured blood vessel at a lesion site. Subsequently, in a cascade of enzymatically regulated reactions, soluble fibrinogen molecules are converted by the enzyme thrombin to insoluble strands of fibrin that hold the platelets together in a thrombus. At each step in the cascade, a protein precursor is converted to a protease that cleaves the next protein precursor in the series. Cofactors are required at most of the steps.

Factor VIII circulates as an inactive, non-covalent, metal ion-dependent heterodimer precursor in blood, bound tightly and non-covalently to von Willebrand factor. This procofactor form of the protein contains a heavy chain (HC) comprised of A1(a1)A2(a2)B domains and a light chain (LC) comprised of (a3)A3C1C2 domains, with the lower case a representing short (~30-40 residue) segments rich in acidic residues. Factor VIII is proteolytically activated by proteolytic cleavages at the A1A2, A2B and A3A3 junctions catalyzed by thrombin or factor Xa, which serves to dissociate it from von Willebrand factor and activate its procoagulant function in the cascade. In its active form, the protein factor VIIIa is a cofactor that increases the catalytic efficiency of the serine protease factor IXa in the membrane-dependent conversion of zymogen factor X to the serine protease, factor Xa factor by several orders of magnitude.

Gene therapy has been proposed as treatment modality for supplementing deficiencies in clotting factors in hemophiliacs and there have been attempts to engineer FVIII constructs that are suitable for treatment of humans. For example, Connelly, et al. reported that treatment of FVIII-deficient mice with human FVIII-encoding adenoviral vectors resulted in expression of biologically active human FVIII (Connelly, et al., Blood, Vol. 91, No. 9 (1998), pp. 3273-3281). Sarkar, et al. reported that use of AAV8 serotype in combination with FVIII corrected plasma FVIII activity in mouse models (Sarkar, et al., Blood, Vol. 103, No. 4 (2004), pp. 1253-1260).

However, as in many areas of gene therapy, theory is much more straightforward than successful, effective implementation. Difficulties in implementation of gene therapy techniques include problems encountered in the use of viruses as gene vectors and insufficient expression levels of FVIII. For example, human FVIII secretes very inefficiently and the yield is logs lower comparing to similar proteins such as factor V. Further, while viruses are effective as gene vectors because they can be used to transduce cells leading to protein expression in vivo, the proteins coating the virus particle may activate the body's immune system.

Thus, in view of the foregoing, there is a need for approaches that can efficiently express the target FVIII protein in sufficient quantity to reduce the required dose of viral vector to tolerable levels.

SUMMARY

The present invention provides modified factor VIII (FVIII) proteins, FVIII encoding nucleic acids, and FVIII-expression vectors, as well as methods of using the modified FVIII genes in the treatment of FVIII deficiencies, such as hemophilia A.

In one aspect, present invention provides a mutant human factor VIII having increased expression or secretion as compared to wild-type factor VIII.

In one embodiment, the recombinant mutant human factor VIII includes one or more amino acid substitution(s) selected from the group consisting of I86, Y105, A108, D115, Q117, F129, G132, H134, M147, L152 and combinations thereof.

In another embodiment, the recombinant mutant human factor VIII includes one or more amino acid substitution(s) selected from the group consisting of I86V, Y105F, A108S, D115E, Q117H, F129L, G132K, H134Q, M147T, L152P and combinations thereof.

In another embodiment, the recombinant mutant human factor VIII includes amino acid substitutions in each of the amino acids I86, Y105, A108, D115, Q117, F129, G132, H134, M147 and L152.

In another embodiment, the recombinant mutant human factor VIII includes the amino acid substitutions I86V, Y105F, A108S, D115E, Q117H, F129L, G132K, H134Q, M147T and L152P.

In another embodiment, the recombinant mutant human factor VIII includes one or more amino acid substitution(s) selected from the group consisting of I86, A108, G132, M147, L152 and combinations thereof.

In another embodiment, the recombinant mutant human factor VIII includes one or more amino acid substitution(s) selected from the group consisting of I86V, A108S, G132K, M147T, L152P and combinations thereof.

In another embodiment, the recombinant mutant human factor VIII includes amino acid substitutions in each of I86V, A108S, G132K, M147T and L152P.

In another embodiment, the recombinant mutant human factor VIII includes the amino acid substitutions I86V, A108S, G132K, M147T and L152P.

In other embodiments, the human factor VIII mutants further include a deletion in the B domain of human factor VIII.

In other embodiments, the human factor VIII mutants further include the a2 and/or a3 domain(s) of human factor VIII.

In another aspect, the present invention provides isolated polynucleotide sequences encoding the human factor VIII mutants described herein.

In yet another aspect, the present invention provides an expression vector operatively linked to the polynucleotides encoding the human factor VIII mutants described herein.

In a further aspect, the present invention provides a pharmaceutical composition comprising an expression vector operatively linked to the polynucleotides encoding the human factor VIII mutants described herein.

In another aspect, the present invention provides a method for treating a patient with a factor VIII deficiency comprising administering to a patient in need thereof a pharmaceutical composition comprising an expression vector operatively linked to the polynucleotides encoding a human factor VIII mutant described herein in an amount effective for treating the factor VIII deficiency.

In yet another aspect, the present invention provides a method for expressing a human factor VIII polypeptide mutant comprising: (a) transforming a host cell with an expression vector operatively linked to a polynucleotides encoding a human factor VIII mutant according to the present invention; (b) growing the host cell under conditions suitable for expressing the human factor VIII polypeptide mutant; and (c) purifying the human factor VIII polypeptide mutant from host cells expressing said mutant.

BRIEF DESCRIPTION OF DRAWINGS

FIG. 2 is a graph showing an alignment of the first 200 amino acids of the secreted human factor VIII heavy chain alongside a modified factor VIII with 10 exemplary substitutions for enhanced secretion.

FIG. 3 is a graph showing the alignment of the first 200 amino acids of the secreted human factor VIII heavy chain alongside a modified human factor VIII mutant with 5 exemplary substitutions for enhanced secretion.

FIG. 4 summarizes exemplary amino acids determined to affect human factor VIII secretion.

FIG. 9 show a comparison of the secretion of different human factor VIII mutants in 293 cells. Amino acids in hBDD-F8-X10 were reverted back to their corresponding wild type amino acids. In hBDD-F8-X10-6p, 6 of 10 amino acids in hBDD-F8-X10 differing from wild type F8 were reverted back to their wild type amino acids.

DETAILED DESCRIPTION

Figure 1:
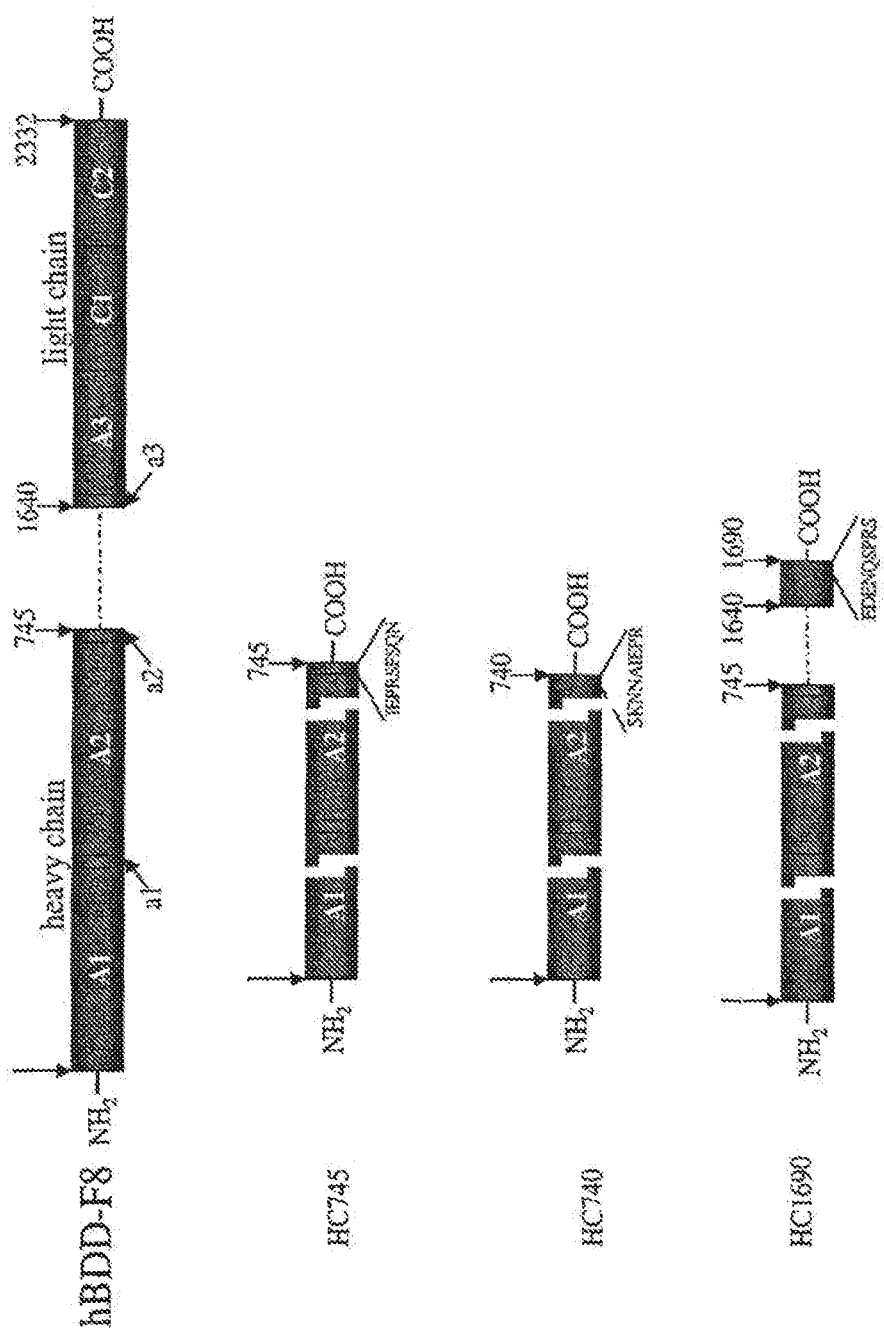
FIG. 1 illustrates the structural domains of the human factor VIII heavy and light chains, including several heavy chain constructions utilized in the present invention.
Figure 5:
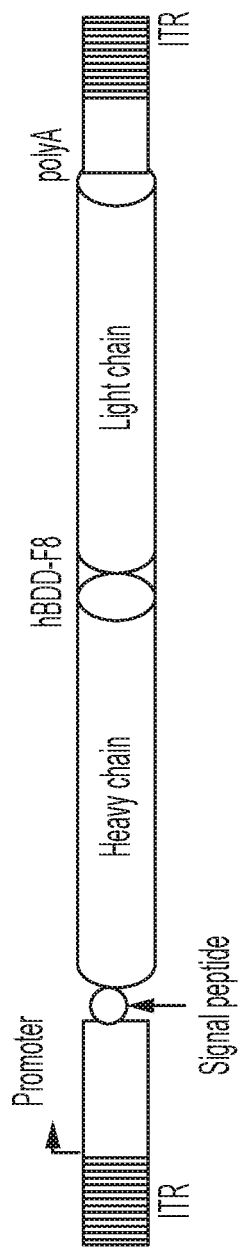
FIGS. 5 and 6 depict exemplary AAV vectors for expressing B-domain deleted human factor VIII mutants or human factor VIII heavy chain.

Various terms relating to the biological molecules of the present invention are used hereinabove and also throughout the specification and claims.

The phrase "secretion enhanced factor VIII (seFVIII, seF8)" refers to a modified FVIII (F8) which has been genetically altered such that the encoded protein exhibits at least 10% or 20% or 50% or 100% increase in secretion when compared to unmodified FVIII. The nucleotide sequences described herein are readily obtainable from GenBank. For human FVIII, see Accession No. NG-011403.1.

The phrase "BDD" refers to a "B-domainless" factor VIII (F8 or FVIII) mutant lacking the B domain.

The phrase "one or more" followed by a list of elements or species is intended to encompass any permutation of elements or species in the list. Thus, for example, the phrase "one or more substitution mutations selected from the group consisting of A, B, C, D, E and F" may include any combination of substitution mutations containing A, B, C, D, E and/or F.

As used herein, ranges may be expressed from one particular integer value to another particular integer value. When such a range is expressed, it should understand that any and all integer values within that range define separate embodiments according to the present invention and that the full scope of embodiments includes within the range further includes any and all sub-ranges between any pair of integer values in the initial range.

With reference to nucleic acids of the invention, the term "isolated nucleic acid", when applied to DNA, refers to a DNA molecule that is separated from sequences with which it is immediately contiguous (in the 5' and 3' directions) in the naturally occurring genome of the organism from which it originates. For example, the "isolated nucleic acid" may comprise a DNA or cDNA molecule inserted into a vector, such as a plasmid or virus vector, or integrated into the DNA of a prokaryote or eukaryote. The nucleic acid codons can be optimized for enhanced expression in the mammalian cells.

With respect to RNA molecules of the invention, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form (the term "substantially pure" is defined below).

With respect to protein, the term "isolated protein" or "isolated and purified protein" is sometimes used herein. This term refers primarily to a protein produced by expression of an isolated nucleic acid molecule of the invention. Alternatively, this term may refer to a protein which has been sufficiently separated from other proteins with which it would naturally be associated, so as to exist in "substantially pure" form.

The term "promoter region" refers to the transcriptional regulatory regions of a gene, which may be found at the 5' or 3' side of the coding region, or within the coding region, or within introns.

The term "vector" refers to a small carrier DNA molecule into which a DNA sequence can be inserted for introduction into a host cell where it will be replicated. An "expression vector" is a specialized vector that contains a gene or nucleic acid sequence with the necessary regulatory regions needed for expression in a host cell.

The term "operably linked" means that the regulatory sequences necessary for expression of a coding sequence are placed in the DNA molecule in the appropriate positions relative to the coding sequence so as to effect expression of the coding sequence. This same definition is sometimes applied to the arrangement of coding sequences and transcription control elements (e.g., promoters, enhancers, and termination elements) in an expression vector. This definition is also sometimes applied to the arrangement of nucleic acid sequences of a first and a second nucleic acid molecule wherein a hybrid nucleic acid molecule is generated.

The term "substantially pure" refers to a preparation comprising at least 50-60% by weight the compound of interest (e.g., nucleic acid, oligonucleotide, protein, etc.). More preferably, the preparation comprises at least 75% by weight, and most preferably 90-99% by weight, of the compound of interest. Purity is measured by methods appropriate for the compound of interest (e.g., chromatographic methods, agarose or polyacrylamide gel electrophoresis, HPLC analysis, and the like).

The phrase "consisting essentially of when referring to a particular nucleotide sequence or amino acid sequence means a sequence having the properties of a given SEQ ID NO. For example, when used in reference to an amino acid sequence, the phrase includes the sequence per se and molecular modifications that would not affect the basic and novel characteristics of the sequence.

The term "oligonucleotide," as used herein refers to primers and probes of the present invention, and is defined as a nucleic acid molecule comprised of two or more ribo- or deoxyribonucleotides, preferably more than three. The exact size of the oligonucleotide will depend on various factors and on the particular application for which the oligonucleotide is used. The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and method of use. For example, for diagnostic applications, depending on the complexity of the target sequence, the oligonucleotide probe typically contains 15-25 or more nucleotides, although it may contain fewer nucleotides.

The term "percent identical" is used herein with reference to comparisons among nucleic acid or amino acid sequences. Nucleic acid and amino acid sequences are often compared using computer programs that align sequences of nucleic or amino acids thus defining the differences between the two. Comparisons of nucleic acid sequences may be performed using the GCG Wisconsin Package version 9.1, available from the Genetics Computer Group in Madison, Wis. For convenience, the default parameters (gap creation penalty=12, gap extension penalty=4) specified by that program are intended for use herein to compare sequence identity. Alternately, the Blastn 2.0 program provided by the National Center for Biotechnology Information (found on the world wide web at ncbi.nlm.nih.gov/blast/; Altschul, et al., 1990, J Mol Biol 215:403-410) using a gapped alignment with default parameters, may be used to determine the level of identity and similarity between nucleic acid sequences and amino acid sequences.

A "corresponding" nucleic acid or amino acid or sequence of either, as used herein, is one present at a site in a factor VIII or hybrid factor VIII molecule or fragment thereof that has the same structure and/or function as a site in the factor VIII molecule of another species, although the nucleic acid or amino acid number may not be identical. A sequence "corresponding to" another factor VIII sequence substantially corresponds to such sequence, and hybridizes to the human factor VIII DNA sequence designated SEQ ID NO: 1 under stringent conditions. A sequence "corresponding to" another factor VIII sequence also includes a sequence that results in the expression of a factor VIII or claimed procoagulant hybrid factor VIII or fragment thereof and would hybridize to a nucleic molecule comprising SEQ ID NO: 1 but for the redundancy of the genetic code.

A "unique" amino acid residue or sequence, as used herein, refers to an amino acid sequence or residue in the factor VIII molecule of one species that is different from the homologous residue or sequence in the factor VIII molecule of another species.

"Specific activity," as used herein, refers to the activity that will correct the coagulation defect of human factor VIII-deficient plasma. Specific activity is measured in units of clotting activity per milligram total factor VIII protein in a standard assay in which the clotting time of human factor VIII deficient plasma is compared to that of normal human plasma. One unit of factor VIII activity is the activity present in one milliliter of normal human plasma. In the assay, the shorter the time for clot formation, the greater the activity of the factor VIII being assayed. Hybrid human/porcine factor VIII has coagulation activity in a human factor VIII assay. This activity, as well as that of other hybrid or hybrid equivalent factor VIII molecules or fragments thereof, may be less than, equal to, or greater than that of either plasma-derived or recombinant human factor VIII.

"Subunits" of human or animal factor VIII, as used herein, are the heavy and light chains of the protein. The heavy chain of factor VIII contains three domains, A1, A2, and B. The light chain of factor VIII also contains three domains, A3, C1, and C2.

The terms "epitope", "antigenic site", and "antigenic determinant", as used herein, are used synonymously and are defined as a portion of the human, animal, hybrid, or hybrid equivalent factor VIII or fragment thereof that is specifically recognized by an antibody. It can consist of any number of amino acid residues, and it can be dependent upon the primary, secondary, or tertiary structure of the protein. In accordance with this disclosure, a hybrid factor VIII, hybrid factor VIII equivalent, or fragment of either that includes at least one epitope may be used as a reagent in the diagnostic assays described below. In some embodiments, the hybrid or hybrid equivalent factor VIII or fragment thereof is not cross-reactive or is less cross-reactive with all naturally occurring inhibitory factor VIII antibodies than human or porcine factor VIII.

The term "immunogenic site", as used herein, is defined as a region of the human or animal factor VIII, hybrid or hybrid equivalent factor VIII, or fragment thereof that specifically elicits the production of antibody to the factor VIII, hybrid, hybrid equivalent, or fragment in a human or animal, as measured by routine protocols, such as immunoassay, e.g., ELISA, or the Bethesda assay, described herein. It can consist of any number of amino acid residues, and it can be dependent upon the primary, secondary, or tertiary structure of the protein. In some embodiments, the hybrid or hybrid equivalent factor VIII or fragment thereof is nonimmunogenic or less immunogenic in an animal or human than human or porcine factor VIII.

"Factor VIII deficiency," as used herein, includes deficiency in clotting activity caused by production of defective factor VIII, by inadequate or no production of factor VIII, or by partial or total inhibition of factor VIII by inhibitors. Hemophilia A is a type of factor VIII deficiency resulting from a defect in an X-linked gene and the absence or deficiency of the factor VIII protein it encodes.

In one aspect, the present invention relates to a recombinant factor VIII mutant molecule (e.g., protein or nucleic acid) characterized by increased expression and/or secretion as compared to wild-type factor VIII.

Exemplary human factor VIII cDNA (nucleotide) and predicted amino acid sequences are shown in SEQ ID NOs: 1 and 2, respectively. Human factor VIII is synthesized and secreted as an approximately 300 kDa single chain protein of 2332 amino acids with internal sequence homologies defining a series of structural "domains" as follows: NH2-A1-a1-A2-a2-B-a3-A3-C1-C2-COOH (FIG. 4). As used herein, a factor VIII "domain" is defined by a continuous sequence of amino acids characterized by e.g., internal amino acid sequence identity to structurally related domains and by sites of proteolytic cleavage by thrombin. Further, the terms "domainless" or "lacking a domain" should be understood to mean that at least 95% or 100% of the domain has been deleted. Unless otherwise specified, factor VIII domains are defined by the following amino acid residues in the human factor VIII amino acid sequence set forth in SEQ ID NO:2:

A1, residues Ala1-Arg372
A2, residues Ser373-Arg740
B, residues Ser741-Arg1648;
a3, residues P1640-Arg1649;
A3, residues Ser1690-Ile2032;
C1, residues Arg2033-Asn2172; and
C2, residues Ser2173-Tyr2332

The A3-C1-C2 sequence includes residues Ser1690-Tyr2332. The remaining sequence, residues Glu1649-Arg1689, is usually referred to as the factor VIII light chain activation peptide (FIG. 1). Factor VIII is proteolytically activated by thrombin or factor Xa, which dissociates it from von Willebrand factor, forming factor VIIIa, which has procoagulant function. The biological function of factor VIIIa is to increase the catalytic efficiency of factor IXa toward factor X activation by several orders of magnitude. Thrombin-activated factor VIIIa is a 160 kDa A1/A2/A3-C1-C2 heterotrimer that forms a complex with factor IXa and factor X on the surface of platelets or monocytes.

A cDNA sequence encoding the wild-type human factor VIII has the nucleotide sequence set forth in SEQ ID NO:1. In SEQ ID NO:1, the first 57 nucleotides of the factor VIII open reading frame encodes a signal peptide sequence which is typically cleaved off from the mature factor VIII protein represented by SEQ ID NO:2.

Preferred recombinant factor VIII mutants include or encode one or more amino acid substitutions in the region from as 86 to as 152 of the wild-type human factor VIII amino acid sequence set forth in SEQ ID NO:2. Substitutions within any of these positions may employ any of the other 19 amino acids.

With reference to mutants described herein, the notion represented by "(amino acid a)-(SEQ ID NO:2 amino acid #b)-(amino acid c)" should be understood to mean that wild type amino acid a (one-letter code) at amino acid number b of SEQ ID NO:2 has been mutated to amino acid c.

In certain preferred embodiments, the human factor VIII polypeptide mutant comprises amino acid substitution(s) in one or more amino acids in SEQ ID NO:2 selected from the group consisting of I86, Y105, A108, D115, Q117, F129, G132, H134, M147 and L152. Further, the human factor VIII mutants may include any permutation of mutations encompassing these ten amino acid sites. Exemplary human factor VIII mutants are described in FIG. 4.

An exemplary recombinant factor VIII of this invention includes a point mutation involving a substitution at I86 of SEQ ID NO:2. A preferred substitution includes valine (i.e., I86V). Further preferred substitutions include leucine (I86L) and methionine (I86M).

Another exemplary recombinant factor VIII includes a point mutation involving a substitution at Y105 of SEQ ID NO:2. The substitution may include any of the other 19 amino acids. Preferred substitutions include Y105F and Y105W.

Another exemplary recombinant factor VIII includes a point mutation involving a substitution of at positions A108 of SEQ ID NO:2. A preferred substitution includes: A108S. Further preferred substitutions include A108S, A108G, A108T and A108P.

Another exemplary recombinant factor VIII includes a point mutation involving a substitution of at positions D115 of SEQ ID NO:2. A preferred substitution includes: D115E. Further preferred substitutions include D115N, D115H, D115Q, D115R and D115K.

Another exemplary recombinant factor VIII includes a point mutation involving a substitution of at positions Q117 of SEQ ID NO:2. A preferred substitution includes: Q117H. Further preferred substitutions include Q117N, Q117E, Q117D, Q117R and Q117K.

Another exemplary recombinant factor VIII includes a point mutation involving a substitution of at positions F129 of SEQ ID NO:2. A preferred substitution include: F129L. Further preferred substitutions include F129V, F129I, F129M, F129P, F129T and F129K.

Another exemplary recombinant factor VIII includes a point mutation involving a substitution of at positions G132 of SEQ ID NO:2. A preferred substitution include: G132K. Further preferred substitutions include G132E, G132D, G132R, G132T, G132M, G132N, G132S and G132W.

Another exemplary recombinant factor VIII includes a point mutation involving a substitution of at positions H134 of SEQ ID NO:2. A preferred substitution includes: H134Q. Further preferred substitutions include H134G, H134Y, H134N, H134E, H134D, H134R and H134K.

Another exemplary recombinant factor VIII includes a point mutation involving a substitution of at positions M147 of SEQ ID NO:2. A preferred substitution includes: M147T. Further preferred substitutions include M147A, M147G, M147S and M147P.

Another exemplary recombinant factor VIII includes a point mutation involving a substitution of at positions L152 of SEQ ID NO:2. A preferred substitution includes: L152P. Further preferred substitutions include L152S, L152G and L152T.

Another exemplary recombinant factor VIII includes multiple substitutions of one or more amino acid residues at positions I86, A108, G132, M147, L152 of SEQ ID NO:2. The substitution(s) can include any permutation of mutations encompassing these five amino acid sites. Specific embodiments may include mutations at one or more substitution mutations selected from the group consisting of I86V, A108S, G132K, M147T, L152P. Further preferred embodiments include 2, 3, 4 or 5 substitutions, including any combination (or permutation) of substitutions selected from I86V, A108S, G132K, M147T and L152P.

Exemplary recombinant factor VIII mutants include point mutation(s) involving substitution(s) at one or more amino acid residues in SEQ ID NO:2 selected from the group consisting of I86, Y105, A108, D115, Q117, F129, G132, H134, M147 and L152. The substitution(s) can include any permutation of mutations encompassing these ten amino acid sites. Specific embodiments may include mutations at one or more substitution mutations selected from the group consisting of I86V, Y105F, A108S, D115E, Q117H, F129L, G132K, H134Q, M147T and L152P. Further preferred embodiments include 2, 3, 4 or up to 9 substitutions, including any combination (or permutation) of substitutions selected from I86V, Y105F, A108S, D115E, Q117H, F129L, G132K, H134Q, M147T and L152P.

The nucleic acids encoding the above mentioned factor VIII substitutions are included in this invention and include all possible nucleic acids encoding the breadth of substitution mutants described herein.

Compared to wild type factor VIII in production (in cell lines or in vivo), the above described factor VIII mutants may exhibit increases in factor VIII secretion of between 5% to 10,000 fold, 10% to 2,000 fold, 50% up to 500 fold, 2 to 200 fold, 5 to 100 fold, 10 to 50 fold, at least 2 fold, at least 5 fold, at least 10 fold, at least 20 fold, at least 50 fold, at least 100 fold, at least 200 fold, at least 500 fold, at least 2,000 fold or at least 10,000 fold.

In certain embodiments, suitable mutant factor VIII sequences may be further modified to include, delete, or modify other factor VIII sequences to confer properties with regard to other attributes, including, without limitation, antigenicity, circulating half-life, protein secretion, affinity for factor IXa and/or factor X, altered factor VIII-inactivation cleavage sites, stability of the activated factor VIII form, immunogenicity, and shelf-life.

In certain specific embodiments, the mutant factor VIII may be modified to produce a B-domain deleted (BDD) or "B-domainless" factor VIII product. FIG. 1 shows an exemplary BDD factor VIII embodiment containing amino acid residues 1-740 and 1690-2332 of SEQ ID NO:2. Preferably, the recombinant B-domainless factor VIII contains one or multiple substitutions at positions I86, Y105, A108, D115, Q117, F129, G132, H134, M147, L152 as described herein.

In one embodiment, a B-domainless recombinant factor VIII is produced, whereby the B-domain is replaced with a DNA linker segment and at least one codon is replaced with a codon encoding an amino acid residue having the same charge as a corresponding residue of porcine factor VIII (see, e.g., U.S. Patent Application Publication No. 2004/0197875 to Hauser, et al.).

In another embodiment, a B-domainless recombinant factor VIII is produced having a truncated factor IX intron 1 inserted in one or more locations (see, e.g., U.S. Pat. No. 6,800,461 to Negrier and U.S. Pat. No. 6,780,614 to Negrier). This recombinant factor VIII can be used for yielding higher production of the recombinant factor VIII in vitro as well as in a transfer vector for gene therapy (see, e.g., U.S. Pat. No. 6,800,461 to Negrier). In a particular embodiment, the recombinant factor VIII can be encoded by a nucleotide sequence having a truncated factor IX intron 1 inserted in two locations and having a promoter that is suitable for driving expression in hematopoietic cell lines, and specifically in platelets (see, e.g., U.S. Pat. No. 6,780,614 to Negrier).

A second example of a suitable mutant factor VIII that can be modified in accordance with the present invention is a chimeric human/animal factor VIII that contains one or more animal amino acid residues as substitution(s) for human amino acid residues that are responsible for the antigenicity of human factor VIII. In particular, animal (e.g., porcine) residue substitutions can include, without limitation, one or more of the following: R484A, R488G, P485A, L486S, Y487L, Y487A, S488A, S488L, R489A, R489S, R490G, L491S, P492L, P492A, K493A, G494S, V495A, K496M, H497L, L498S, K499M, D500A, F501A, P502L, I503M, L504M, P505A, G506A, E507G, I508M, I508A, M2199I, F2200L, L2252F, V2223A, K2227E and/or L225I (U.S. Pat. No. 5,859,204 to Lollar, U.S. Pat. No. 6,770,744 to Lollar, and U.S. Patent Application Publication No. 2003/0166536 to Lollar). Preferably, the recombinant chimeric factor VIII contains one or multiple substitutions at positions I86, Y105, A108, D115, Q117, F129, G132, H134, M147 and L152 as described herein.

In a further embodiment, the mutant factor VIII is modified to confer greater stability of activated factor VIII by virtue of fused A2 and A3 domains. In particular, a factor VIII can be modified by substituting cysteine residues at positions 664 and 1826, (i.e., Y664C, T1826C) resulting in a mutant factor VIII forming a Cys664-Cys1826 disulfide bond covalently linking the A2 and A3 domains (Gale, et al., "An Engineered Interdomain Disulfide Bond Stabilizes Human Blood Coagulation Factor VIIIa," J. Thrombosis and Haemostasis 1(9): 1966-1971 (2003)). Preferably, the recombinant fused domain (A2-A3) factor VIII contains one or multiple substitutions at positions I86, Y105, A108, D115, Q117, F129, G132, H134, M147 and L152 as described herein.

In a further embodiment, a mutant factor VIII in accordance with the present invention (e.g., containing one or multiple substitutions at positions I86, Y105, A108, D115, Q117, F129, G132, H134, M147 and/or L152) is further modified to confer altered inactivation cleavage sites. For example, Arg336 or Arg562 may be substituted used to decrease the mutant factor VIII's susceptibility to cleavage enzymes that normally inactivate the wild type factor VIII (see, e.g., Amano, et al., "Mutation at Either Arg336 or Arg562 in Factor VIII is Insufficient for Complete Resistance to Activated Protein C (APC)-Mediated Inactivation: implications for the APC Resistance Test," Thrombosis & Haemostasis 79(3):557-63 (1998)).

In a further embodiment, a mutant factor VIII in accordance with the present invention (e.g., containing one or multiple substitutions at positions I86, Y105, A108, D115, Q117, F129, G132, H134, M147 and/or L152) is further modified to confer enhanced affinity for factor IXa (see, e.g., Fay, et al., "Factor VIIIa A2 Subunit Residues 558-565 Represent a Factor IXa Interactive Site," J. Biol. Chem. 269(32):20522-7 (1994); Bajaj, et al., "Factor IXa: Factor VIIIa Interaction. Helix 330-338 of Factor IXa Interacts with Residues 558-565 and Spatially Adjacent Regions of the A2 Subunit of Factor VIIIa," J. Biol. Chem. 276(19):16302-9 (2001); and Lenting, et al., "The Sequence Glu1811-Lys1818 of Human Blood Coagulation Factor VIII Comprises a Binding Site for Activated Factor IX," J. Biol. Chem. 271(4):1935-40 (1996)) and/or factor X (see, e.g., Lapan, et al., "Localization of a Factor X Interactive Site in the A1 Subunit of Factor VIIIa," J. Biol. Chem. 272:2082-88 (1997)).

In yet another further embodiment, a mutant factor VIII in accordance with the present invention (e.g., containing one or multiple substitutions at positions I86, Y105, A108, D115, Q117, F129, G132, H134, M147 and/or L152) is further modified to further enhance secretion of factor VIII (see, e.g., Swaroop, et al., "Mutagenesis of a Potential Immunoglobulin-Binding Protein-Binding Site Enhances Secretion of Coagulation Factor VIII," J. Biol. Chem. 272 (39):24121-4 (1997)).

In a further embodiment, a mutant factor VIII in accordance with the present invention (e.g., containing one or multiple substitutions at positions I86, Y105, A108, D115, Q117, F129, G132, H134, M147 and/or L152) is further modified to confer increased circulating half-life. This may be achieved through various approaches, including, without limitation, by reducing interactions with heparan sulfate (Sarafanov, et al., "Cell Surface Heparan Sulfate Proteoglycans Participate in Factor VIII Catabolism Mediated by Low Density Lipoprotein Receptor-Related Protein," J. Biol. Chem. 276(15): 11970-9 (2001)) and/or low-density lipoprotein receptor-related protein ("LRP") (Saenko, et al., "Role of the Low Density Lipoprotein-Related Protein Receptor in Mediation of Factor VIII Catabolism," J. Biol. Chem. 274(53):37685-92 (1999); and "The Light Chain of Factor VIII Comprises a Binding Site for Low Density Lipoprotein Receptor-Related Protein," J. Biol. Chem. 274 (34):23734-9 (1999)).

An eighth example of a suitable mutant factor VIII that can be modified in accordance with the present invention is a modified factor VIII encoded by a nucleotide sequence modified to code for amino acids within known, existing epitopes to produce a recognition sequence for glycosylation at asparagine residues (see, e.g., U.S. Pat. No. 6,759,216 to Lollar). Such modification can be useful escaping detection by existing inhibitory antibodies (low antigenicity factor VIII) and decreasing the likelihood of developing inhibitory antibodies (low immunogenicity factor VIII). In one representative embodiment, the modified factor VIII is mutated to incorporate a consensus amino acid sequence for N-linked glycosylation, such as N-X-S/T (see U.S. Pat. No. 6,759,216 to Lollar).

A ninth example of a suitable mutant factor VIII that can be modified in accordance with the present invention is a modified factor VIII that is a procoagulant-active factor VIII having various mutations (see, e.g., U.S. Patent Application Publication No. 2004/0092442 to Kaufman, et al.). One example of this embodiment relates to a modified factor VIII that has been modified to (i) delete the von Willebrand factor binding site, (ii) add a mutation at Arg 740, and (iii) add an amino acid sequence spacer between the A2- and A3-domains, where the amino acid spacer is of a sufficient length so that upon activation, the procoagulant-active factor VIII protein becomes a heterodimer (see U.S. Patent Application Publication No. 2004/0092442 to Kaufman, et al).

Further, the mutant factor VIII can be modified to take advantage of various advancements regarding recombinant coagulation factors generally (see, e.g., Saenko, et al., "The Future of Recombinant Coagulation Factors," J. Thrombosis and Haemostasis 1:922-930 (2003)).

The recombinant factor VIII of the present invention can be modified at position I86, Y105, A108, D115, Q117, F129, G132, H134, M147, L152, as well as be modified to be B-domainless, to be chimeric, to have fused A2-A3 domains, to have altered inactivation cleavage sites, to have enhanced factor IXa and/or factor X affinity, to have enhanced specific activity, to have an increased circulating half-life, to have mutant glycosylation sites, or to possess any two or more of such modifications in addition to the modifications at position(s) I86, Y105, A108, D115, Q117, F129, G132, H134, M147 and/or L152.

Another aspect of the present invention relates to a method of making a recombinant factor VIII having increased specific activity compared to that of a wild-type factor VIII. This method involves altering the amino acid sequence of a wild-type factor VIII to yield a recombinant factor VIII. Alteration of the amino acid sequence of the wild-type factor VIII can include, for example, introducing at least one point mutation in or near at least one calcium binding site of the wild-type factor VIII. Thereafter, using protein analysis techniques well-known in the art, a determination can be made as to whether the recombinant factor VIII has increased specific activity compared to that of the wild-type factor VIII.

The recombinant factor VIII is preferably produced in a substantially pure form. In a particular embodiment, the substantially pure recombinant factor VIII is at least about 80% pure, more preferably at least 90% pure, most preferably at least 95% pure, 98% pure, 99% pure or 99.9% pure. A substantially pure recombinant factor VIII can be obtained by conventional techniques well known in the art. Typically, the substantially pure recombinant factor VIII is secreted into the growth medium of recombinant host cells. Alternatively, the substantially pure recombinant factor VIII is produced but not secreted into growth medium. In such cases, to isolate the substantially pure recombinant factor VIII, the host cell carrying the recombinant plasmid is propagated, lysed by sonication, heat, or chemical treatment, and the homogenate is centrifuged to remove cell debris. The supernatant is then subjected to sequential ammonium sulfate precipitation. The fraction containing the substantially pure recombinant factor VIII is subjected to gel filtration in an appropriately sized dextran or polyacrylamide column to separate the recombinant factor VIII. If necessary, a protein fraction (containing the substantially pure recombinant factor VIII) may be further purified by high performance liquid chromatography ("HPLC").

Another aspect of the present invention relates to an isolated nucleic acid molecule that encodes a recombinant mutant factor VIII as described herein. The isolated nucleic acid molecule encoding the recombinant mutant factor VIII can be an RNA or DNA. The nucleic acid codons can be further optimized for enhanced expression.

In one embodiment, the isolated nucleic acid molecule can have a nucleotide sequence encoding the amino acid sequence of SEQ ID NO:2 as modified with one of the substitutions at positions identified in this invention (i.e., possessing one to three nucleotide substitutions within codon 86 (nt 256-258), codon 105 (nt: 313-315), codon 108 (nt: 322-324), codon 115 (nt: 343-345), codon 117 (nt:

349-351), codon 129 (nt: 385-387), codon 132 (nt: 394-396), codon 134 (nt: 400-402), codon 147 (nt: 439-441) and/or codon 152 (nt: 454-456) of SEQ ID NO:1 (the first 57 nucleotides are not counted since they encode the signal peptides). The isolated nucleic acid molecule may have one or multiple changes in these positions in any combination.

In another embodiment, the isolated nucleic acid molecule can have a nucleotide sequence encoding a B-domainless factor VIII of the type described above, as modified with one or multiple substitutions at position(s) I86, Y105, A108, D115, Q117, F129, G132, H134, M147 and/or L152.

In another embodiment, the isolated nucleic acid molecule can have a nucleotide sequence encoding a chimeric human/porcine of the type described above, as modified with one or multiple substitutions at position(s) I86, Y105, A108, D115, Q117, F129, G132, H134, M147 and/or L152.

In a further embodiment, the isolated nucleic acid molecule can have a nucleotide sequence encoding a fused A2-A3 domain factor VIII of the type described above, as modified with one or multiple substitutions at position(s) I86, Y105, A108, D115, Q117, F129, G132, H134, M147 and/or L152.

In another embodiment, the isolated nucleic acid molecule can have a nucleotide sequence encoding a factor VIII whose inactivation sites have been modified as described above, as further modified with one or multiple substitutions at position(s) I86, Y105, A108, D115, Q117, F129, G132, H134, M147 and/or L152.

In yet another embodiment, the isolated nucleic acid molecule can have a nucleotide sequence encoding a factor VIII whose affinity for factor IXa and/or factor X has been enhanced, along with one or multiple substitutions at position(s) I86, Y105, A108, D115, Q117, F129, G132, H134, M147 and/or L152.

In a still further embodiment, the isolated nucleic acid molecule can have a nucleotide sequence encoding a factor VIII whose affinity for various serum-binding proteins has been altered to increase its circulating half-life and further modified with one or multiple substitutions at position(s) I86, Y105, A108, D115, Q117, F129, G132, H134, M147 and/or L152.

In a further embodiment, the isolated nucleic acid molecule can have a nucleotide sequence encoding a factor VIII that has increased secretion in culture, as further modified with one or multiple substitutions at position(s) I86, Y105, A108, D115, Q117, F129, G132, H134, M147 and/or L152.

In a further embodiment, the isolated nucleic acid molecule can have a nucleotide sequence encoding a factor VIII that possesses one or more non-naturally occurring glycosylation site(s) along with one or multiple substitutions at position(s) I86, Y105, A108, D115, Q117, F129, G132, H134, M147 and/or L152.

In yet another embodiment, the isolated nucleic acid molecule encodes a recombinant factor VIII that is modified with one or more substitutions at position(s) I86, Y105, A108, D115, Q117, F129, G132, H134, M147 and/or L152 and is further modified to possess any combination of the following modification: modified to be B-domainless, modified to be chimeric, modified to have fused A2-A3 domains, modified to have one or more altered inactivation cleavage site(s), modified to have enhanced factor IXa and/or factor X affinity, modified to have enhanced secretion, modified to have an increased circulating half-life, and modified to possess one or more non-naturally occurring glycosylation site(s).

Another aspect of the present invention relates to an expression vector for expressing the mutant factor VIII polynucleotides described herein. As used herein, the term "expression vector" refers to a viral or non-viral vector that comprise a polynucleotide encoding the novel peptide of the present invention in a form suitable for expression of the polynucleotide in a host cell. One type of non-viral vector is a "plasmid," which includes a circular double-stranded DNA loop into which additional DNA segments can be ligated. In the present specification, "plasmid" and "vector" can be used interchangeably as the plasmid is the most commonly used form of vector.

When preparing an expression vector, the transgene sequences may be inserted into a plasmid containing suitable bacterial sequences for replication in bacterial, as well as eukaryotic cells. Any convenient plasmid may be employed, which can include markers allowing for selection in a bacterium, and generally one or more unique, conveniently located restriction sites. The selection of a vector will depend on the preferred transformation technique and target host for transformation.

Expression vectors for expressing mutant factor VIII polypeptides include one or more regulatory sequences operably linked to the polynucleotide sequence to be expressed. It will be appreciated by those skilled in the art that the design of the expression vector can depend on such factors as the choice of the host cell to be transformed, the level of expression of protein desired, and the like. The expression vectors of the invention can be introduced into host cells to thereby produce the mutant factor VIII proteins described herein.

As used herein, the term "control sequences" or "regulatory sequences" refers to DNA sequences necessary for the expression of an operably linked coding sequence in a particular host organism. The term "control/regulatory sequence" is intended to include promoters, enhancers and other expression control elements (e.g., polyadenylation signals). Control/regulatory sequences include those which direct constitutive expression of a nucleotide sequence in many types of host cells and those which direct expression of the nucleotide sequence only in certain host cells (e.g., tissue-specific regulatory sequences).

A nucleic acid sequence is "operably linked" to another nucleic acid sequence when the former is placed into a functional relationship with the latter. For example, a DNA for a presequence or secretory leader peptide is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, synthetic oligonucleotide adaptors or linkers are used in accordance with conventional practice.

Suitable expression vectors for directing expression in mammalian cells generally include a promoter, as well as other transcription and translation control sequences known in the art. In certain embodiments, the mammalian expression vector is capable of directing expression of the polynucleotide preferentially in a particular cell type (e.g., tissue-specific regulatory elements are used to express the polynucleotide). Tissue-specific regulatory elements are known in the art and may include, for example, liver cell-specific promoters and/or enhancers (e.g., albumin promoter, a-I antitrypsin promoter, apoE enhancer). Alternatively, a constitutive promoter (e.g., HCMV) active in virtually any cell type may be used.

In certain preferred embodiments, the expression vectors are viral vectors. Viral vectors typically have one or more viral genes removed and include a gene/promotor cassette inserted into a viral genome insertion site for insertion of exogenous transgenes, including the mutant factor VIII genes described herein. The necessary functions of the removed gene(s) may be supplied by cell lines which have been engineered to express the gene products of the early genes in trans. Exemplary viral vectors include, but are not limited to, adeno-associated viral (AAV) vectors, retroviral vectors, including lentiviral vectors, adenoviral vectors, herpes viral vectors, and alphavirus vectors. Other viral vectors include astrovirus, coronavirus, orthomyxovirus, papovavirus, paramyxovirus, parvovirus, picornavirus, poxvirus, togavirus viral vectors and the like. The viral vector may comprise any suitable nucleic acid construct, such as a DNA or RNA construct and may be single stranded, double stranded, or duplexed.

Once the DNA construct of the present invention has been prepared, it is ready to be incorporated into a host cell. Accordingly, another aspect of the present invention relates to a method of making a recombinant cell comprising a factor VIII nucleic acid. Basically, this entails introducing the DNA construct into cells via transformation, transduction, electroporation, calcium phosphate precipitation, liposomes and the like and selecting for cells that have incorporated the DNA episomally or integrated into the host genome.

Thus, a further aspect of the present invention relates to a host cell including an isolated nucleic acid molecule encoding the recombinant factor VIII of the present invention. The host cell can contain the isolated nucleic acid molecule as a DNA molecule in the form of an episomal plasmid or stably integrated into the host cell genome. Further, the host cell can constitute an expression system for producing the recombinant mutant factor VIII protein. Suitable host cells can be, without limitation, animal cells (e.g., baby hamster kidney ("BHK") cells), Chinese hamster ovary cells ("CHO"), bacterial cells (e.g., *E. coli*), insect cells (e.g., Sf9 cells), fungal cells, yeast cells (e.g., *Saccharomyces* or *Schizosaccharomyces*), plant cells (e.g., *Arabidopsis* or tobacco cells), algal cells and the like.

Another aspect of the present invention relates to a method of making a recombinant factor VIII of the present invention. This method involves growing a host cell of the present invention under conditions whereby the host cell expresses the recombinant factor VIII. The recombinant factor VIII is then isolated. In one embodiment, the host cell is grown in vitro in a growth medium. In a particular embodiment, suitable growth media can include, without limitation, a growth medium containing a von Willebrand Factor (referred to herein as "VWF"). In this embodiment, the host cell can contain a transgene encoding a VWF or the VWF can be introduced to the growth medium as a supplement. VWF in the growth medium will allow for greater expression levels of the recombinant factor VIII. Once the recombinant factor VIII is secreted into the growth medium, it can then be isolated from the growth medium using techniques well-known by those of ordinary skill in the relevant recombinant DNA and protein arts (including those described herein). In another embodiment, the method of making the recombinant factor VIII of the present invention further involves disrupting the host cell prior to isolation of the recombinant factor VIII. In this embodiment, the recombinant factor VIII is isolated from cellular debris.

When recombinantly produced, the factor VIII protein or polypeptide (or fragment or mutant thereof) is expressed in a recombinant host cell, typically, although not exclusively, a eukaryote. In certain preferred embodiments, eukaryotic host cells, such as mammalian cells, are used to produce mutant factor VIII polypeptides as described herein. Mammalian cells suitable for carrying out the present invention include, among others: COS (e.g., ATCC No. CRL 1650 or 1651), BHK (e.g., ATCC No. CRL 6281), CHO (ATCC No. CCL 61), HeLa (e.g., ATCC No. CCL 2), 293 (ATCC No. 1573), CHOP, and NS-1 cells.

Another aspect of the present invention relates to a method for treating patient with a factor VIII deficiency. In one embodiment, this involves administering to a patient in need thereof a recombinant mutant factor VIII (as described herein) in an amount effective for treating the factor VIII deficiency.

In a particular embodiment, the recombinant factor VIII, alone, or in the form of a pharmaceutical composition (i.e., in combination with stabilizers, delivery vehicles, and/or carriers) is infused into patients intravenously according to the same procedure that is used for infusion of human or animal factor VIII. A suitable effective amount of the recombinant factor VIII can include, without limitation, between about 10 to about 500 units/kg body weight of the patient.

In another embodiment, a method for treating patient with a factor VIII deficiency comprises administering to a patient in need thereof a pharmaceutical composition comprising an expression vector encoding a mutant factor VIII, or a functional fragments thereof, in an amount effective for treating the factor VIII deficiency. In certain embodiments, the recombinant factor VIII can be administered by transplanting cells genetically engineered to produce the recombinant factor VIII, typically via implantation of a device containing such cells. Such transplantation typically involves using recombinant dermal fibroblasts, a non-viral approach (Roth, et al., New Engl. J. Med. 344:1735-1742 (2001)).

Administration of FVIII-encoding expression vectors to factor VIII deficient patients can result in sufficient expression of FVIII polypeptide to functionally reconstitute the coagulation cascade. The expression vector(s) may be administered alone or in combination with other therapeutic agents in a pharmaceutically acceptable or biologically compatible composition.

Figure 10:
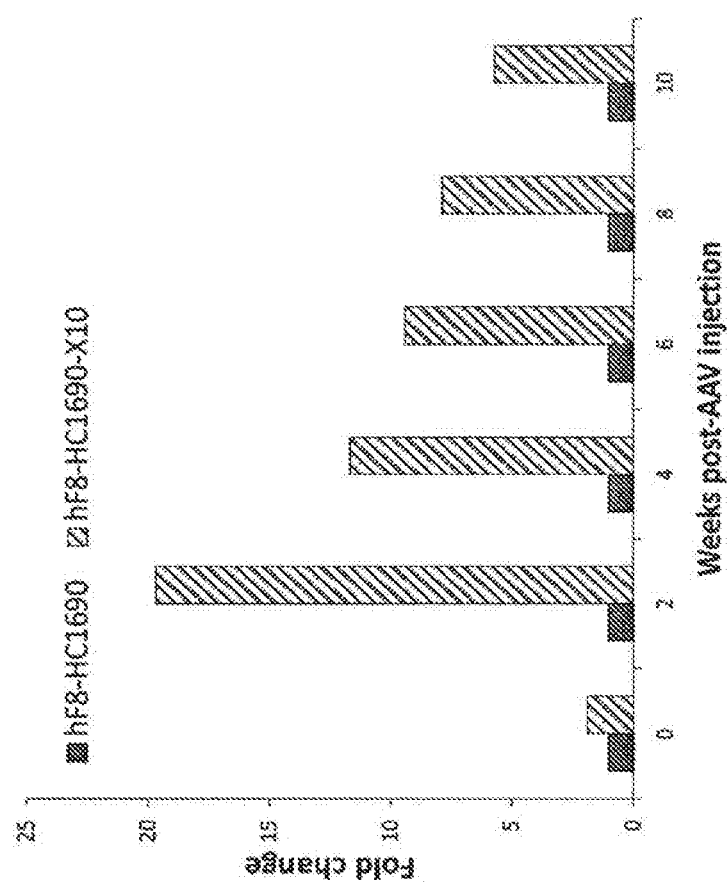
FIG. 10 shows a comparison of the expression and secretion of a mutant factor VIII (F8) heavy chain (HC1690-X10) in an AAV vector construct with a wild type hF8-HC1690 AAV vector construct (AAV/hF8HC1690) in vivo.
Figure 11:
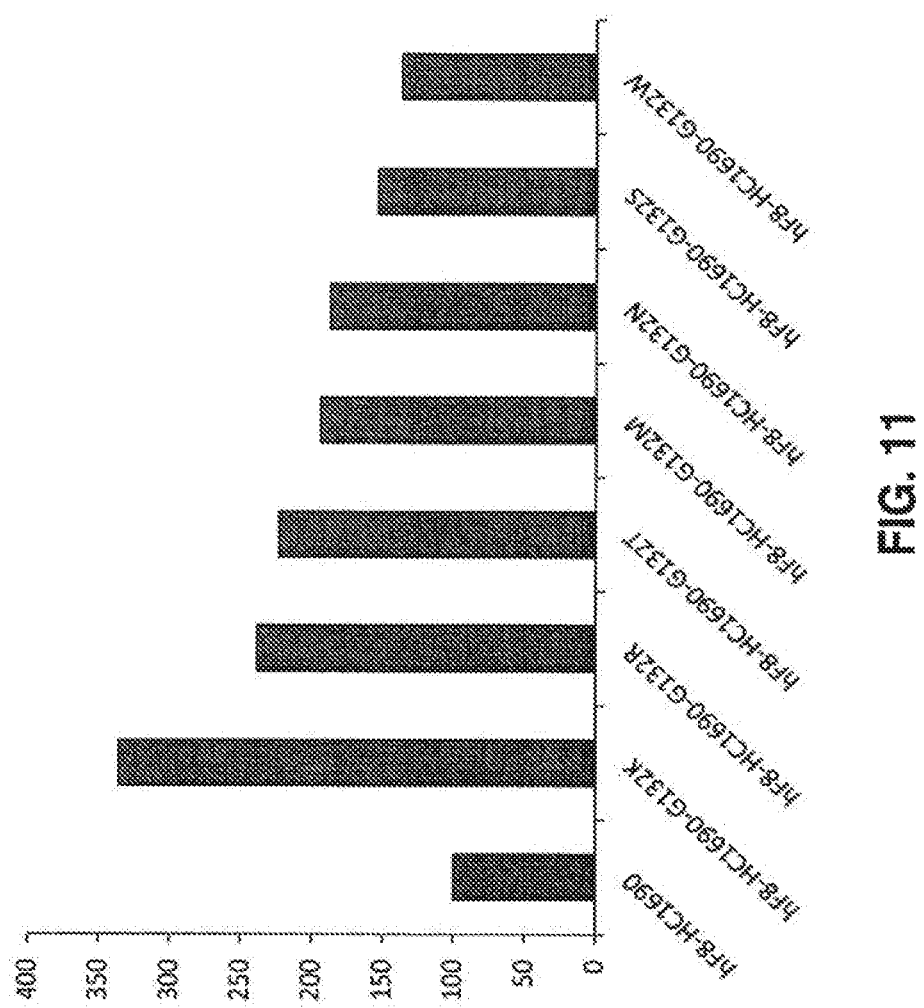
FIG. 11 shows a comparison of the secretion of different G132 factor VIII heavy chain mutants in 293 cells.

The FVIII-encoding polynucleotide can be employed as a single chain molecule containing both heavy and light chain portions (FIG. 10) or split into two or multiple molecules (e.g., heavy and light chain; FIG. 11) in viral or non-viral vectors for delivery into host cells of the patient.

In a preferred embodiment of the invention, the expression vector comprising nucleic acid sequences encoding the mutant FVIII mutants is a viral vector. Viral vectors which may be used in the present invention include, but are not limited to, adenoviral vectors (with or without tissue specific promoters/enhancers), adeno-associated virus (AAV) vectors of multiple serotypes (e.g., AAV-1 to AAV-12, and others) and hybrid AAV vectors, lentivirus vectors and pseudo-typed lentivirus vectors [e.g., Ebola virus, vesicular stomatitis virus (VSV), and feline immunodeficiency virus (FIV)], herpes simplex virus vectors, vaccinia virus vectors, retroviral vectors, lentiviral vectors, non-viral vectors and others.

In certain preferred embodiments, methods are provided for the administration of a viral vector comprising nucleic acid sequences encoding a mutant FVIII, or a functional fragment thereof involve the use of AAV vectors or lentiviral vectors. Most preferably, only the essential parts of vector e.g., the ITR and LTR elements, respectively are included. Direct delivery of vectors or ex-vivo transduction of human cells and followed by infusion into the body will result in expression of mutant FVIIIs thereby exerting a beneficial therapeutic effect on hemostasis by enhancing pro-coagulation activity.

Recombinant AAV and lentiviral vectors have found broad utility for a variety of gene therapy applications. Their utility for such applications is due largely to the high efficiency of in vivo gene transfer achieved in a variety of organ contexts. AAV and lentiviral particles may be used to advantage as vehicles for effective gene delivery. Such virions possess a number of desirable features for such applications, including tropism for dividing and non-dividing cells. Early clinical experience with these vectors also demonstrated no sustained toxicity and immune responses were minimal or undetectable. AAV are known to infect a wide variety of cell types in vivo and in vitro by receptor-mediated endocytosis or by transcytosis. These vector systems have been tested in humans targeting retinal epithelium, liver, skeletal muscle, airways, brain, joints and hematopoietic stem cells. It is likely that non-viral vectors based on plasmid DNA or minicircles will be also suitable gene transfer vectors for a large gene as that encoding FVIII.

It is desirable to introduce a vector that can provide, for example, sufficient expression of a desired gene and minimal immunogenicity. Improved AAV and lentiviral vectors and methods for producing such vectors have been described in detail in a number of references, patents, and patent applications, including Wright J. F. (Hum Gene Ther 20:698-706, 2009) which describes the production of clinical grade vectors. Lentiviral vector can be produced at CHOP and the other vectors are available through the Lentivirus vector production core laboratory by NHLBI Gene Therapy Resource Program (GTRP)-Lentivirus Vector Production Core Laboratory.

For some applications, an expression construct may further comprise regulatory elements which serve to drive expression in a particular cell or tissue type. Such regulatory elements are known to those of skill in the art and discussed in depth in Sambrook, et al. (1989) and Ausubel, et al. (1992). The incorporation of tissue specific regulatory elements in the expression constructs of the present invention provides for at least partial tissue tropism for the expression of the mutant FVIIIs or functional fragments thereof. For example, nucleic acid sequences encoding mutant FVIII under the control of a cytomegalovirus (CMV) promoter can be employed for skeletal muscle expression or the hAAT-ApoE and others for liver specific expression. Hematopoietic specific promoters in lentiviral vectors may also be used to advantage in the methods of the present invention.

In a preferred embodiment, the mutant FVIII sequence is provided as a component of a viral vector packaged in a capsid. In a particularly preferred embodiment, an AAV vector is used for in vivo delivery of the mutant FVIIIs (Gnatenko, et al., Br. J. Haematol. 104:27-36 (1999)). In this case, the AAV vector includes at least one mutant FVIII and associated expression control sequences for controlling expression of the mutant FVIII sequence. As shown in FIGS. 10 and 11, exemplary AAV vectors for expressing mutant FVIII sequences may include promoter-enhancer regulatory regions for FVIII expression and cis-acting ITRs functioning to enable promote replication and packaging of the mutant FVIII nucleic acids into AAV capsids and integration of the mutant FVIII nucleic acid into the genome of a target cell. Preferably, the AAV vector has its rep and cap genes deleted and replaced by the mutant hFVIII sequence and its associated expression control sequences. As shown in FIGS. 10 and 11, the mutant FVIII sequence is typically inserted adjacent to one or two (i.e., flanked by) AAV TRs or TR elements adequate for viral replication. Other regulatory sequences suitable for facilitating tissue-specific expression of the mutant hFVIII sequence in the target cell may also be included.

The viral capsid component of the packaged viral vectors may be a parvovirus capsid. AAV Cap and chimeric capsids are preferred. Examples of suitable parvovirus viral capsid components are capsid components from the Parvoviridae family, such as an autonomous parvovirus or a dependovirus. For example, the viral capsid may be an AAV capsid (e.g., AAV1, AAV2, AAV3, AAV4, AAV5, AAV6, AAV7, AAV8, AAV 9, AAV10, AAV 11 or AAV12 capsid; one skilled in the art would know there are likely other variants not yet identified that perform the same or similar function), or may include components from two or more AAV capsids. A full complement of AAV Cap proteins includes VP1, VP2, and VP3. The ORF comprising nucleotide sequences encoding AAV VP capsid proteins may comprise less than a full complement AAV Cap proteins or the full complement of AAV Cap proteins may be provided.

One or more of the AAV Cap proteins may be a chimeric protein, including amino acid sequences AAV Caps from two or more viruses, preferably two or more AAVs, as described in Rabinowitz et al., U.S. Pat. No. 6,491,907. For example, the chimeric virus capsid can include an AAV I Cap protein or subunit and at least one AAV2 Cap or subunit. The chimeric capsid can, for example, include an AAV capsid with one or more B19 Cap subunits, e.g., an AAV Cap protein or subunit can be replaced by a B19 Cap protein or subunit. For example, the Vp3 subunit of the AAV capsid can be replaced by the Vp2 subunit of B19.

Packaging cells may be cultured to produce packaged viral vectors of the invention. The packaging cells may include heterologous (1) viral vector function(s), (2) packaging function(s), and (3) helper function(s). The viral vector functions typically include a portion of a parvovirus genome, such as an AAV genome, with rep and cap deleted and replaced by the mutant FVIII sequence and its associated expression control sequences as described above.

In certain embodiments, the viral vector functions may suitably be provided as duplexed vector templates, as described in U.S. Patent Publication No. 2004/0029106 to Samulski et al. Duplexed vectors are dimeric self-complementary (sc) polynucleotides (typically, DNA). For example, the DNA of the duplexed vectors can be selected so as to form a double-stranded hairpin structure due to intrastrand base pairing. Both strands of the duplexed DNA vectors may be packaged within a viral capsid. The duplexed vector provides a function comparable to double-stranded DNA virus vectors and can alleviate the need of the target cell to synthesize complementary DNA to the single-stranded genome normally encapsidated by the virus.

The TR(s) (resolvable and non-resolvable) selected for use in the viral vectors are preferably AAV sequences (from any AAV serotype). Resolvable AAV ITRs need not have a wild-type TR sequence (e.g., a wild-type sequence may be altered by insertion, deletion, truncation or missense mutations), as long as the TR mediates the desired functions, e.g., virus packaging, integration, and/or provirus rescue, and the like. The TRs may be synthetic sequences that function as AAV inverted terminal repeats, such as the "double-D sequence" as described in U.S. Pat. No. 5,478,745 to Samulski et al. Typically, but not necessarily, the TRs are from the same parvovirus, e.g., both TR sequences are from AAV2.

The packaging functions include capsid components. The capsid components are preferably from a parvoviral capsid, such as an AAV capsid or a chimeric AAV capsid function. Examples of suitable parvovirus viral capsid components are capsid components from the family Parvoviridae, such as an autonomous parvovirus or a Dependovirus. For example, the capsid components may be selected from AAV capsids, e.g., AAV1-AAV12 and other novel capsids as yet unidentified or from non-human primate sources. Capsid components may include components from two or more AAV capsids.

In certain embodiments, one or more of the VP capsid proteins may comprise chimeric proteins, comprising amino acid sequences from two or more viruses, preferably two or more AAVs, as described in Rabinowitz et al., U.S. Pat. No. 6,491,907. For example, the chimeric virus capsid can include a capsid region from an adeno-associated virus (AAV) and at least one capsid region from a B19 virus. The chimeric capsid can, for example, include an AAV capsid with one or more B19 capsid subunits, e.g., an AAV capsid subunit can be replaced by a B19 capsid subunit. For example, the VP1, VP2 or VP3 subunit of the AAV capsid can be replaced by the VP1, VP2 or VP3 subunit of B19. As another example, the chimeric capsid may include an AAV type 2 capsid in which the type 2 VP1 subunit has been replaced by the VP1 subunit from an AAV type 1, 3, 4, 5, or 6 capsid, preferably a type 3, 4, or 5 capsid. Alternatively, the chimeric parvovirus has an AAV type 2 capsid in which the type 2 VP2 subunit has been replaced by the VP2 subunit from an AAV type 1, 3, 4, 5, or 6 capsid, preferably a type 3, 4, or 5 capsid. Likewise, chimeric parvoviruses in which the VP3 subunit from an AAV type 1, 3, 4, 5 or 6 (more preferably, type 3, 4 or 5) is substituted for the VP3 subunit of an AAV type 2 capsid are preferred. As a further alternative, chimeric parvoviruses in which two of the AAV type 2 subunits are replaced by the subunits from an AAV of a different serotype (e.g., AAV type 1, 3, 4, 5 or 6) are preferred. In exemplary chimeric parvoviruses according to this embodiment, the VP1 and VP2, or VP1 and VP3, or VP2 and VP3 subunits of an AAV type 2 capsid are replaced by the corresponding subunits of an AAV of a different serotype (e.g., AAV type 1, 3, 4, 5 or 6). Likewise, in other preferred embodiments, the chimeric parvovirus has an AAV type 1, 3, 4, 5 or 6 capsid (preferably the type 2, 3 or 5 capsid) in which one or two subunits have been replaced with those from an AAV of a different serotype, as described above for AAV type 2.

The packaged viral vector generally includes the mutant FVIII sequence and expression control sequences flanked by TR elements sufficient to result in packaging of the vector DNA and subsequent expression of the mutant FVIII sequence in the transduced cell. The viral vector functions may, for example, be supplied to the cell as a component of a plasmid or an amplicon. The viral vector functions may exist extrachromosomally within the cell line and/or may be integrated into the cells' chromosomal DNA.

In a preferred embodiment, the mutant FVIII described herein are used for gene therapy of FVIII associated disorders, such as hemophilia A. In this case, expression of the mutant FVIII transgene can enhance clotting in a subject otherwise vulnerable to uncontrolled bleeding due to factor VIII deficiency (e.g., intraarticular, intracranial, or gastrointestinal hemorrhage), including hemophiliacs who have developed antibodies to human factor VIII. The target cells of the vectors are cells capable of expressing polypeptides with FVIII activity, such as those of the hepatic system of a mammal, endothelial cells and other cells with the proper cellular machinery to process the precursor to yield protein with FVIII activity.

In particular embodiments, the present invention provides a pharmaceutical composition comprising a vector of the present invention including a modified gene of FVIII in a pharmaceutically-acceptable carrier and/or other medicinal agents, pharmaceutical agents, carriers, adjuvants, diluents, etc.

The treatment dosages of recombinant factor VIII that should be administered to a patient in need of such treatment will vary depending on the severity of the factor VIII deficiency. Generally, dosage level is adjusted in frequency, duration, and units in keeping with the severity and duration of each patient's bleeding episode. Accordingly, the recombinant factor VIII is included in a pharmaceutically acceptable carrier, delivery vehicle, or stabilizer in an amount sufficient to deliver to a patient a therapeutically effective amount of the protein to stop bleeding, as measured by standard clotting assays.

Factor VIII is classically defined as that substance present in normal blood plasma that corrects the clotting defect in plasma derived from individuals with hemophilia A. The coagulant activity in vitro of purified and partially-purified forms of factor VIII is used to calculate the dose of recombinant factor VIII for infusions in human patients and is a reliable indicator of activity recovered from patient plasma and of correction of the in vivo bleeding defect. There are no reported discrepancies between standard assay of novel factor VIII molecules in vitro and their behavior in the dog infusion model or in human patients, according to Lusher, et al., New Engl. J. Med. 328:453-459 (1993); Pittman, et al., Blood 79:389-397 (1992); and Brinkhous, et al., Proc. Natl. Acad. Sci. 82:8752-8755 (1985).

Usually, the desired plasma factor VIII activity level to be achieved in the patient through administration of the recombinant factor VIII is in the range of 30-200% of normal. In one embodiment, administration of the therapeutic recombinant factor VIII is given intravenously at a preferred dosage in the range from about 5 to 500 units/kg body weight, and particularly in a range of 10-100 units/kg body weight, and further particularly at a dosage of 20-40 units/kg body weight; the interval frequency is in the range from about 8 to 24 hours (in severely affected hemophiliacs); and the duration of treatment in days is in the range from 1 to 10 days or until the bleeding episode is resolved. See, e.g., Roberts, H. R., and M. R. Jones, "Hemophilia and Related Conditions—Congenital Deficiencies of Prothrombin (Factor II, Factor V, and Factors VII to XII)," Ch. 153, 1453-1474, 1460, in Hematology, Williams, W. J., et al., ed. (1990). Patients with inhibitors may require a different amount of recombinant factor VIII than their previous form of factor VIII. For example, patients may require less recombinant factor VIII because of its higher specific activity than the wild-type VIII and its decreased antibody reactivity. As in treatment with human or plasma-derived factor VIII, the amount of therapeutic recombinant factor VIII infused is defined by the one-stage factor VIII coagulation assay and, in selected instances, in vivo recovery is determined by measuring the factor VIII in the patient's plasma after infusion. It is to be understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed recombinant factor VIII.

Treatment can take the form of a single intravenous administration of the recombinant factor VIII or periodic or continuous administration over an extended period of time, as required. Alternatively, therapeutic recombinant factor VIII can be administered subcutaneously or orally with liposomes in one or several doses at varying intervals of time.

For injection, the carrier will typically be a liquid. For other methods of administration, the carrier may be either solid or liquid. For inhalation administration, the carrier will be respirable, and will preferably be in solid or liquid particulate form. As an injection medium, it is preferred to use water that contains the additives usual for injection solutions, such as stabilizing agents, salts or saline, and/or buffers.

Exemplary pharmaceutically acceptable carriers include sterile, pyrogen-free water and sterile, pyrogen-free, phosphate buffered saline. Physiologically-acceptable carriers include pharmaceutically-acceptable carriers. Pharmaceutically acceptable carriers are those which are that is not biologically or otherwise undesirable, i.e., the material may be administered to a subject without causing undesirable biological effects which outweigh the advantageous biological effects of the material. A pharmaceutical composition may be used, for example, in transfection of a cell ex vivo or in administering a viral vector or cell directly to a subject.

Recombinant virus vectors comprising the modified gene of FVIII are preferably administered to the cell in a biologically-effective amount. If the virus vector is administered to a cell in vivo (e.g., the virus is administered to a subject as described below), a biologically-effective amount of the virus vector is an amount that is sufficient to result in transduction and expression of the transgene in a target cell.

The cells transduced with a viral vector are preferably administered to the subject in a "therapeutically-effective amount" in combination with a pharmaceutical carrier. Those skilled in the art will appreciate that the therapeutic effects need not be complete or curative, as long as some benefit is provided to the subject.

Dosages of the cells to administer to a subject will vary upon the age, condition and species of the subject, the type of cell, the nucleic acid being expressed by the cell, the mode of administration, and the like. Typically, at least about $10^2$ to about $10^8$, preferably about $10^3$ to about $10^8$ cells, will be administered per dose. Preferably, the cells will be administered in a therapeutically-effective amount.

Administration of the vector to a human subject or an animal in need thereof can be by any means known in the art for administering virus vectors. Exemplary modes of administration include rectal, transmucosal, topical, transdermal, inhalation, parenteral (e.g., intravenous, subcutaneous, intradermal, intramuscular, and intraarticular) administration, and the like, as well as direct tissue or organ injection, alternatively, intrathecal, direct intramuscular, intraventricular, intravenous, intraperitoneal, intranasal, or intraocular injections. Injectables can be prepared in conventional forms, either as liquid solutions or suspensions, solid forms suitable for solution or suspension in liquid prior to injection, or as emulsions. Alternatively, one may administer the virus in a local rather than systemic manner, for example, in a depot or sustained-release formulation.

In other preferred embodiments, the inventive vector comprising the mutant FVIII gene is administered intramuscularly, more preferably by intramuscular injection or by local administration. The vectors disclosed herein may be administered to the lungs of a subject by any suitable means, but are preferably administered by administering an aerosol suspension of respirable particles comprised of the inventive parvovirus vectors, which the subject inhales. The respirable particles may be liquid or solid. Aerosols of liquid particles comprising the inventive parvovirus vectors may be produced by any suitable means, such as with a pressure-driven aerosol nebulizer or an ultrasonic nebulizer, as is known to those of skill in the art. See, e.g., U.S. Pat. No. 4,501,729.

Dosages of the virus vector with the mutant FVIII gene will depend upon the mode of administration, the disease or condition to be treated, the individual subject's condition, the particular viral vector, and the gene to be delivered, and can be determined in a routine manner. Exemplary doses for achieving therapeutic effects are virus titers of at least about $10^5$, $10^6$, $10^7$ $10^8$, $10^9$, $10^{10}$, $10^{11}$, $10^{12}$, $10^{13}$, $10^{14}$, $10^{15}$ transducing units or more, preferably about $10^8$-$10^{13}$ transducing units, yet more preferably $10^{12}$ transducing units. The mutant FVIII genes may be administered as components of a DNA molecule having regulatory elements appropriate for expression in the target cells. The mutant FVIII genes may be administered as components of viral plasmids, such as rAAV vectors. Viral particles may be administered as viral particles alone, whether as an in vivo direct delivery to the portal vasculature or as an ex vivo treatment comprising administering the vector viral particles in vitro to cells from the animal receiving treatment followed by introduction of the transduced cells back into the donor.

The present invention is further illustrated by the following examples which should not be construed as limiting. The contents of all references, patents, and published patent applications cited throughout this application are incorporated herein by reference.

Example 1: Construction, Expression and Purification of B-Domainless Factor VIII Mutants Plasmid pAAV—CB-F8 carries a B-domainless human factor VIII (hF8) cDNA under the control of a CB promoter (beta-actin promoter with a CMV enhancer). This plasmid, consistent with the construction shown in FIG. 10, was used as template for making various hF8 mutants. A hF8 cDNA fragment encoding the substitution mutations I86V, Y105F, A108S, D115E, Q117H, F129L, G132K, H134Q, M147T and L152P was synthesized chemically and used to replace the corresponding region of pAAV—CB-F8. The resulting plasmid (pAAV—CB-F8-X10) expresses a mutant factor VIII protein with the above 10 mutations (F8-X10; SEQ ID NO: 3).

A factor VIII cDNA fragment encoding the substitution mutations I86V, A108S, G132K, M147T, L152P was synthesized chemically and used to replace the corresponding region of pAAV—CB-F8. The resulting plasmid (pAAV—CB-F8-X5) expresses a mutant factor VIII protein with the above 5 mutations (F8-X5; SEQ ID NO:4).

Site-directed mutagenesis was used to introduce individual mutations corresponding to I86, Y105, A108, D115, Q117, F129, G132, H134, M147, L152 of human factor VIII in the pAAV—CB-F8 plasmid. The resulting plasmids include pAAV—CB-F8-I86V, pAAV—CB-F8-Y105F, pAAV—CB-F8-A108S, pAAV—CB-F8-D115E, pAAV—CB-F8-Q117H, pAAV—CB-F8-F129L, pAAV—CB-F8-

G132K, pAAV—CB-F8-H134Q and pAAV—CB-F8-M147T, pAAV—CB-F8-L152P.

Site-directed mutagenesis was also used to revert back individual mutations in amino acids 86, 105, 108, 115, 117, 129, 132, 134, 147, 152 of hF8-X10 in the pAAV-CB-F8-X10 plasmid to wild-type human amino acids. The resulting plasmids include pAAV-CB-F8-X10-V861, pAAV—CB-F8-X10-F105Y, pAAV—CB-F8-X10-S108A, pAAV—CB-F8-X10-E115D, pAAV—CB-F8-X10-HI17Q, pAAV—CB-F8-X10-L129F, pAAV—CB-F8-X10-K132G, pAAV—CB-F8-X10-Q134H, pAAV—CB-F8-X10-T147M, pAAV—CB-F8-X10-P152L. These mutants were tested as described Example 4 (FIG. 7) below.

A set of degenerated oligonucleotides with NNN corresponding to G132 position was used to create all 19 mutations corresponding to G132. The resulting factor VIII mutant plasmids include pAAV—CB-F8-G132A, pAAV—CB-F8-G1321, pAAV—CB-F8-G132V etc. The last letter indicates the amino acid substitution at that particular position. A similar strategy can be used to generate other substitutions in accordance with the present invention.

The above described plasmids contain an AAV-ITR and can be used to generate AAV vectors. A liver specific promoter can be used to replace the CB promoter to reduce the size of the expression cassette and to improve vector packaging and expression in the liver. Other tissue specific promoter can also be used as well.

Sequences between the FVIII heavy chain and the FVIII stop codon were removed from the FVIII expression vectors. The resulting heavy chain (HC) mutants contain the first 745 amino acid of FVIII and lack B domain (BDD) and light chain (LC) sequences. The plasmid pAAV—CB-HC-X10 contains mutations corresponding to I86V, Y105F, A108S, D115E, Q117H, F129L, G132K, H134Q, M147T and L152P in the heavy chain. The plasmid pAAV—CB-HC-X5 contains mutations corresponding to I86V, A108S, G132K, M147T, L152P in the heavy chain. The plasmid pAAV—CB-HC-G132K contains the G132K mutation in the heavy chain. Alternatively, acidic region 3 (a3) can be added to these constructs to obtain HC mutants in an HC1690 background.

Figure 7:
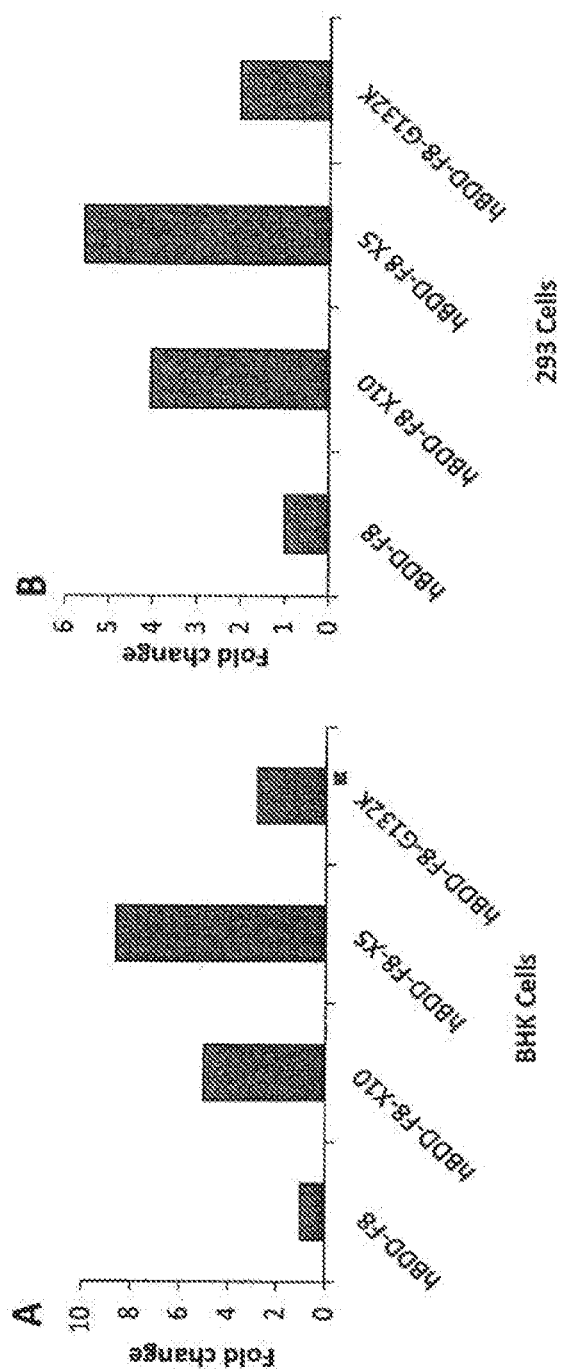
FIG. 7 shows a comparison of the secretion of different human factor VIII mutants in BHK cells (panel A) or 293 cells (panel B).

Example 2: Comparison of Different Factor VIII Mutants for Secretion in Tissue Culture Cells Plasmids pAAV-CB-hBDD-F8 (wt), pAAV-CB-hBDD-F8-X10, pAAV-CB-hBDD-F8-X5 and pAAV-CB-hBDD-F8-G312K were separately transfected in BHK cells (panel A) or 293 cells (panel B). Secreted F8 in the media was harvested and assayed by aPTT assay at 48 hours post transfection. The expression/secretion by wild type human BDD-F8(hBDD) was set as 100%. As shown in FIG. 7, the hF8 mutants were secreted at about 2-8.5 fold higher expression levels than the wild type hF8.

Example 3: Comparison of Human Factor VIII Mutant Secretion In Vivo

Figure 8:
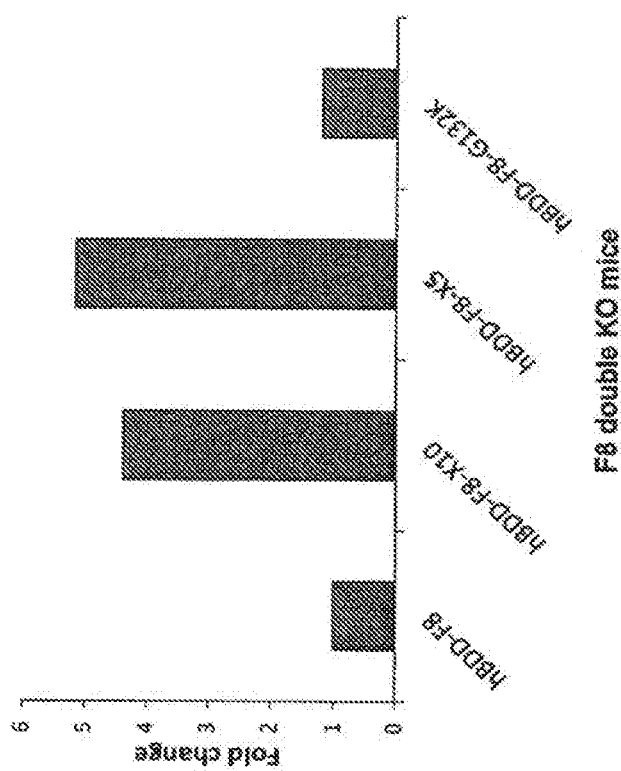
FIG. 8 shows a comparison of the secretion of different human factor VIII mutants in secretion in vivo. Plasmids pAAV-CB-hBDDF8 (carrying human factor VIII with B-domain deleted), pAAV-CB-hBDDF8-X10 (carrying hF8-BDD with 10 substitutions), pAAV-CB-hBDD-F8-X5 (carrying hBDDF8 with 5 substitutions) or pAAV-CB-hBDD-F8-G3 1 2K (hF8 with G132K substitutions) were injected in factor VIII double knock-out Balb/c mice.

Plasmids pAAV-CB-hBDDF8 (B-domain deleted (BDD) wt hF8), pAAV-CB-hBDDF8-X10 (hF8-BDD with 10 substitutions; SEQ ID NO:3), pAAV-CB-hBDD-F8-X5(hF8 with 5 substitutions; SEQ ID NO:4) and pAAV-CB-hBDD-F8-G312K (hF8 with G132K substitution) were separately injected to Balb/c and F8 double knock-out mice. Secreted F8 in the blood was collected and assayed by aPTT assay at 48 hours post injection. The expression/secretion by wild type human F8 (hBDD-F8) was set as 100%. All mutants described here outperform the wild type factor VIII. As shown in FIG. 8, the hF8 mutants were secreted at about 1.2-5.2 fold higher expression levels than the wild type hF8.

Example 4: Comparison of Different Factor VIII Mutants in Secretion

Plasmids encoding amino acids in hBDD-F8-X10 were modified to revert back the mutant substitutions to their corresponding wild type amino acids as indicated in the table. For example, hBDD-F8-X10-V861 means that "V86" in hBDD-F8-X10 was changed back to "I". In hBDD-F8-X10-6p, 6 of 10 mutant amino acids in hBDD-F8-X10 were reverted back to their corresponding wild type amino acids. The above plasmids were separately transfected in 293 cells. Secreted F8 in the media was harvested and assayed by aPTT assay at 48 hours post transfection. The expression/secretion by hBDD-F8-X10 was set as 100%. As shown in FIG. 9, all of the revertants exhibited reduced expression and secretion as compared to the hBDD-F8-X10 mutant.

Example 5: Comparison of Different Factor VIII Mutants in Secretion

AAV8 vector AAV-apoEhAAT-hF8HC1690 (carrying human factor VIII heavy chain aa#1-745 and a3 sequence, apoEhAAT: human alpha one antitrypsin promoter with apo E enhancer) and AAV-apoEhAAT-hF8-HC-X10 (hF8HC with 10 substitutions) were each separately injected in F8 knock-out mice with a light chain expression vector (dose: each vector 1E11 particles/mouse). Secreted F8 in the blood was collected and assayed by aPTT assay the indicated times. The expression/secretion by wild type human F8 heavy chain (hF8-HC1690) was set as 100%. The hF8-HC1690-X10 mutant described here outperform the wild type heavy chain expression. As shown in FIG. 10, the hF8-HC1690-X10 mutant was secreted at about 6-20 fold higher expression levels compared to wild type hF8HC.

Example 6: Comparison of G132 Factor VIII Heavy Chain Mutants in Secretion in 293 Cells Plasmid pAAV-CB-hF8-HC1690 (carrying human factor VIII heavy chain aa#1-745 and a3 sequence; see FIG. 1) or plasmids with indicated substitutions at G132 were transfected in 293 cells with an F8 light chain (LC) expression plasmid. Secreted F8 in the media was collected and assayed by aPTT assay at 48 hours post transfection. The expression/secretion by wild type human F8 heavy chain (hF8-HC1690) was set as 100%. As shown in FIG. 11, the F8 G132HC1690 mutants were secreted at about 1.4-3.4 fold higher expression levels compared to wild type hF811C.

Figure 6:
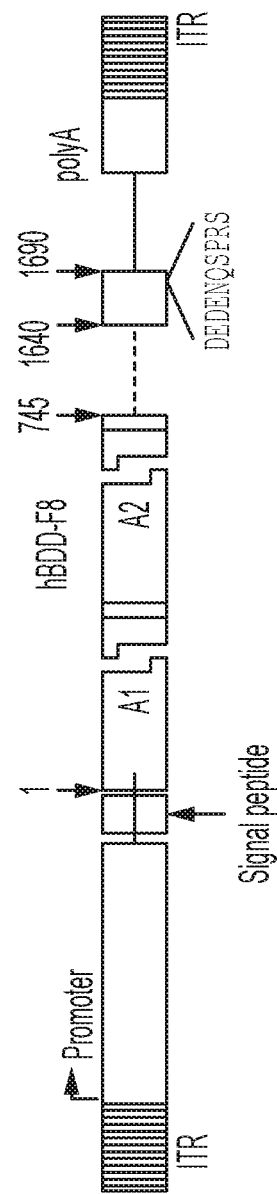
Figure 12:
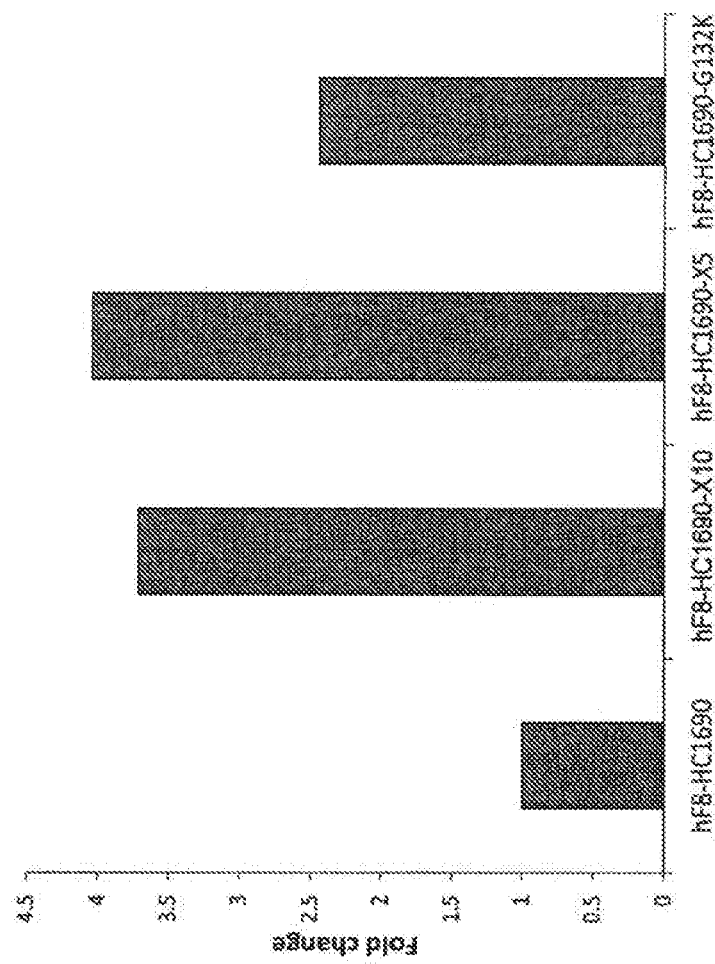
FIG. 12 shows a comparison of the secretion of different factor VIII heavy chain mutants in expression/secretion in factor VIII double knock-out Balb/c mice.

Example 7: Comparison of Different Factor VIII Heavy Chain Mutants in Expression/Secretion In Vivo Plasmids pAAV-CB-hF8-IIC1690 (carrying human factor VIII heavy chain aa#1-745 and acidic region 3 (a3) sequence; see FIGS. 1, 6), pAAV-CB-hF8-HC1690-X10 (hF8 heavy chain with 10 substitutions; SEQ ID NO:5), pAAV-CB-hF8-HC1690-X5 (hF8 heavy chain with 5 substitutions along with a3 sequence; SEQ ID NO:6) and pAAV-CB-hF8-HC1690-G312K (hF8 heavy chain with G132K substitution and a3 sequence) were separately injected in Balb/c and F8 double knock-out mice along with a light chain expression plasmid. Secreted F8 in the blood was collected and assayed by aPTT assay at 48 hours post injection. The expression/secretion by wild type human F8 heavy chain (hF8-HC1690) was set as 100%. As shown in FIG. 12, the hF8 mutants were secreted at about 2.5-4.5 fold higher expression levels than the wild type hF8HC.

Figure 13:
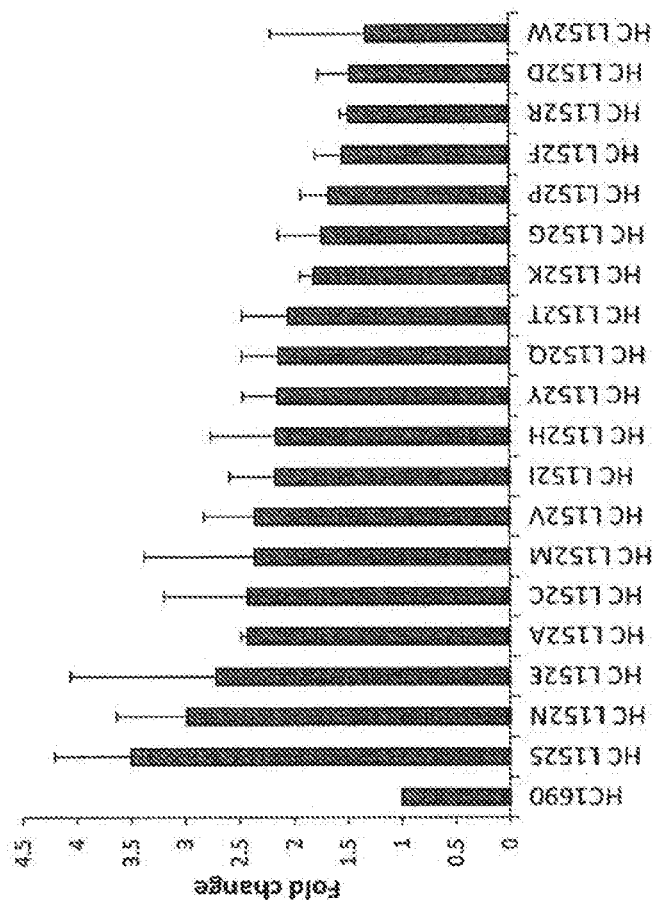
FIG. 13 shows a comparison of the secretion of different L152 factor VIII heavy chain mutants in 293 cells.

Example 8: Comparison of L152 Factor VIII Heavy Chain Mutants in Secretion in 293 Cells Plasmid pAAV-CB-hF8-HC1690 (carrying human factor VIII heavy chain aa#1-745 and a3 sequence; see FIGS. 1, 6) or plasmids with indicated substitutions at L152 were separately transfected in 293 cells with a hF8 light chain expression plasmid. Secreted hF8 in the media was collected and assayed by aPTT assay at 48 hours post transfection. The expression/secretion by wild type human F8 heavy chain (hF8-HC1690) was set as 100%. The hF8-L152HC mutants are identified by their specific amino acid substitutions in the Figure. As shown in FIG. 13, the hF8-L152HC mutants were secreted at about 1.4-3.5 fold higher expression levels compared to wild type hF8HC

Figure 14:
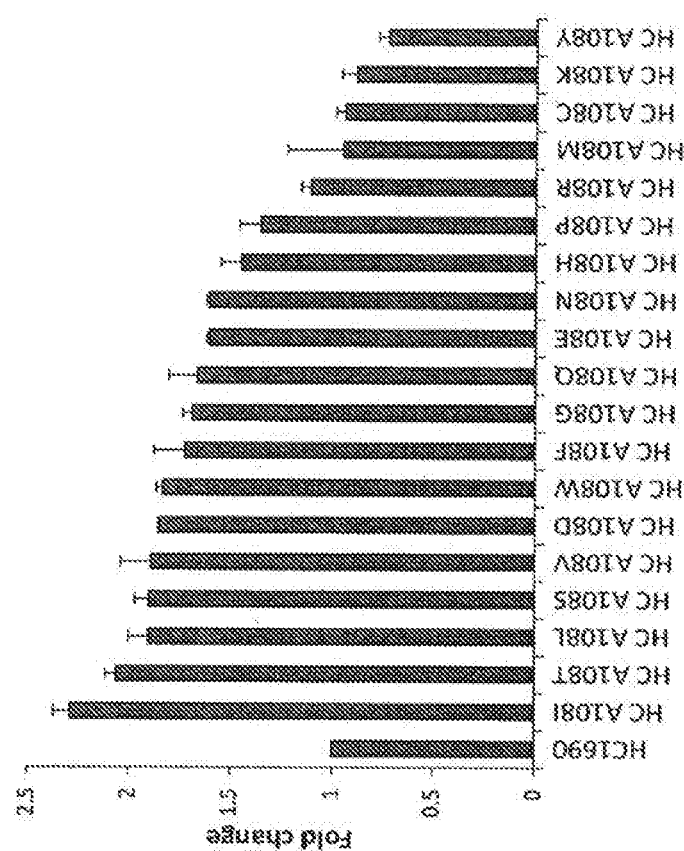
FIG. 14 shows a comparison of the secretion of different A108 factor VIII heavy chain mutants in 293 cells.

Example 9: Comparison of A108 Factor VIII Heavy Chain Mutants in Secretion in 293 Cells Plasmid pAAV-CB-hF8-HC1690 (carrying human factor VIII heavy chain aa#1-745 and a3 sequence; see FIG. 1) or plasmids with indicated substitutions at A108 were separately transfected in 293 cells with a hF8 light chain expression plasmid. Secreted hF8 in the media was collected and assayed by aPTT assay at 48 hours post transfection. The hF8-A108HC mutants are identified by their specific amino acid substitutions in the Figure. The expression/secretion by wild type human F8 heavy chain (hF8-HC1690) was set as 100%. As shown in FIG. 14, the majority of hF8-A108HC mutants were secreted at higher expression levels compared to wild type hF8HC.

Figure 15:
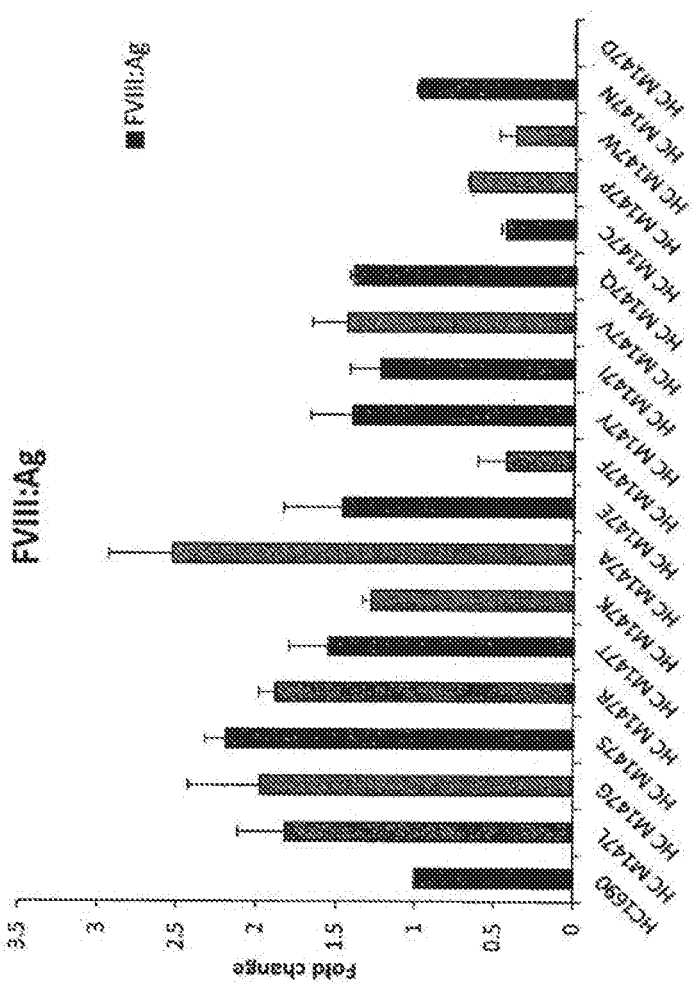
FIG. 15 shows a comparison of the secretion of different M147 factor VIII heavy chain mutants in 293 cells.
Figure 16:
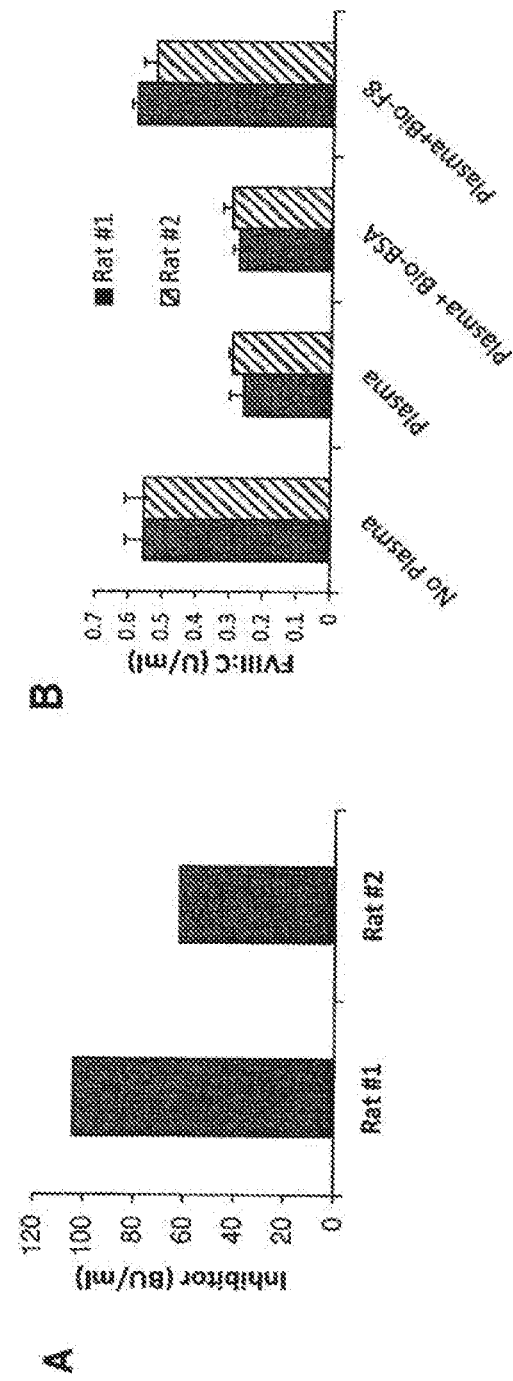
FIG. 16 shows that there was no formation of neutralizing antibodies against 5 mutated amino acids in the F8−/− rat model.

Example 10: Comparison of M147 Factor VIII Heavy Chain Mutants in Secretion in 293 Cells Plasmid pAAV-CB-hF8-HC1690 (carrying human factor VIII heavy chain aa#1-745 and a3 sequence; see FIG. 1) or plasmids with indicated substitutions at M147 were separately transfected in 293 cells with a hF8 light chain expression plasmid. Secreted hF8 in the media was collected and assayed by hF8 ELISA at 48 hours post transfection. The hF8-M147HC mutants are identified by their specific amino acid substitutions in the Figure. The expression/secretion by wild type human F8 heavy chain (hF8-HC1690) was set as 100%. As shown in FIG. 15, the majority of hF8-M1471-IC mutants were secreted at higher expression levels compared to wild type hF8HC.

Example 11: Neutralizing Antibodies Against 5 Mutated Amino Acids were not Detected in the F8−/− Rat Model F8−/− rats in a WAG/RijYcb background with single mutation in the A1 domain (Leu176Pro) were administered AAV-TTR-hF8-X10 at $1\times10^{12}$ viral particles/per rat. Of 3 injected rats, two were confirmed to develop rat anti-human factor VIII inhibitory antibodies against factor VIII as determined by a Bethesda assay. Panel A is representative of inhibitor levels in rat plasma at week 8. Panel B shows the activity of F8 remains in the supernatant after antibody absorption. To determine whether the inhibitory antibodies specifically target the 5 mutated amino acids, we used an excess of biotinylated recombinant human F8 (1.2 1.tg of Bio-F8) to saturate the inhibitory antibodies against regular FVIII in rat plasma. Then 30 1.1.1 of streptavidin agarose was used to pull down antigen-antibody complexes by rotation at room temperature for 1 hour and then centrifuged at 10,000 rpm for 2 min. An equivalent amount of biotinylated BSA (Bio-BSA) was used as a control. 200 ng of BDD-F8-X5 concentrate from a stably expressing cell line was then added to the rat plasma pretreated with Bio-F8 or Bio-BSA. Rat plasma without pretreatment was used as control. The F8 activity in the supernatant was determined by one-stage aPTT assay. As shown in FIG. 15, neutralizing antibodies against the five mutated amino acids were not detected in this F8−/− rat model.

The above Examples show that the mutant factor VIII products of the present invention express and/or secrete better than wild type factor VIII, therefore they can decrease the production cost and improve transgene expression levels when using a gene transfer vector. They can also allow lower vector doses to be administered and higher factor VIII expression levels. The above description is for the purpose of teaching a person of ordinary skill in the art how to practice the present invention. It is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence effective to meet the objectives there intended, unless the context specifically indicates the contrary.

What is claimed is:

1. An isolated polynucleotide encoding a polypeptide, wherein the polypeptide comprises wildtype human factor VIII with amino acid substitutions at positions I86, Y105, A108, D115, Q117, F129, G132, H134, M147 and L152.

2. An expression vector comprising the polynucleotide of claim 1.

3. A host cell comprising the polynucleotide of claim 1.

4. A host cell comprising the expression vector of claim 2.

5. A pharmaceutical composition comprising the expression vector of claim 2.

6. The isolated polynucleotide of claim 1, wherein the amino acid substitutions are selected from the group consisting of I86V, I86L, I86M, Y105F, Y105W, A108S, A108G, A108T, A108P, D115E, D115N, D115H, D115Q, D115R, D115K, Q117H, Q117N, Q117E, Q117D, Q117R, Q117K, F129L, F129V, F129I, F129M, F129P, F129T, F129K, G132K, G132E, G132D, G132R, G132T, G132M, G132N, G132S, G132W, H134Q, H134G, H134Y, H134N, H134E, H134D, H134R, H134K, M147T, M147A, M147G, M147S, M147P, L152P, L152S, L152G and L152T.

7. The isolated polynucleotide of claim 1, wherein the polypeptide comprises amino acid substitutions A108S, M147T, and L152P.

8. The isolated polynucleotide of claim 6, wherein the amino acid substitutions are selected from the group consisting of I86V, Y105F, A108S, D115E, Q117H, F129L, G132K, H134Q, M147T and L152P.

9. The isolated polynucleotide of claim 1, wherein the polypeptide comprises the amino acid substitution I86V.

10. The isolated polynucleotide of claim 6, wherein the amino acid substitutions are selected from the group consisting of I86V, A108S, G132K, M147T and L152P.

11. The isolated polynucleotide of claim 6, wherein the amino acid substitutions are selected from the group consisting of A108S, M147T, and L152P.

12. The isolated polynucleotide of claim 11, wherein the polypeptide further comprises amino acid substitutions I86V and G132K.

13. The isolated polynucleotide of claim 1, wherein the polypeptide comprises a deletion in the B domain.

14. An isolated polynucleotide comprising SEQ ID NO: 1, wherein the polynucleotide encodes a human factor VIII polypeptide comprising amino acid substitutions at positions I86, Y105, A108, D115, Q117, F129, G132, H134, M147 and L152.

15. The isolated polynucleotide of claim 14, wherein the polypeptide comprises a deletion in the B domain.

16. The isolated polynucleotide of claim 14, wherein the amino acid substitutions are selected from the group consisting of I86V, I86L, I86M, Y105F, Y105W, A108S, A108G, A108T, A108P, D115E, D115N, D115H, D115Q, D115R, D115K, Q117H, Q117N, Q117E, Q117D, Q117R, Q117K, F129L, F129V, F129I, F129M, F129P, F129T, F129K, G132K, G132E, G132D, G132R, G132T, G132M, G132N, G132S, G132W, H134Q, H134G, H134Y, H134N, H134E, H134D, H134R, H134K, M147T, M147A, M147G, M147S, M147P, L152P, L152S, L152G and L152T.

\* \* \* \* \*

SEQUENCE LISTING

```
<160> NUMBER OF SEQ ID NOS: 9

<210> SEQ ID NO 1
<211> LENGTH: 7056
<212> TYPE: DNA
<213> ORGANISM: Homo sapiens

<400> SEQUENCE: 1
atgcaaatag agctctccac ctgcttcttt ctgtgccttt tgcgattctg ctttagtgcc      60 accagaaagat actacctggg tgcagtggaa ctgtcatggg actatatgca aagtgatctc     120
ggtgagctgc ctgtggacgc aagatttcct cctagagtgc caaaatcttt tccattcaac     180
```

```
acctcagtcg tgtacaaaaa gactctgttt gtagaattca cggatcacct tttcaacatc    240
gctaagccaa ggccaccctg gatgggtctg ctaggtccta ccatccaggc tgaggtttat    300
gatacagtgg tcattacact taagaacatg gcttcccatc ctgtcagtct tcatgctgtt    360
ggtgtatcct actggaaagc ttctgaggga gctgaatatg atgatcagac cagtcaaagg    420
gagaaagaag atgataaagt cttccctggt ggaagccata catatgtctg gcaggtcctg    480
aaagagaatg gtccaatggc ctctgaccca ctgtgcctta cctactcata tctttctcat    540
gtggacctgg taaaagactt gaattcaggc ctcattggag ccctactagt atgtagagaa    600
gggagtctgg ccaaggaaaa gacacagacc ttgcacaaat ttatactact ttttgctgta    660
tttgatgaag ggaaaagttg gcactcagaa acaaagaact ccttgatgca ggatagggat    720
gctgcatctg ctcgggcctg gcctaaaatg cacacagtca atggttatgt aaacaggtct    780
ctgccaggtc tgattggatg ccacaggaaa tcagtctatt ggcatgtgat tggaatgggc    840
accactcctg aagtgcactc aatattcctc gaaggtcaca catttcttgt gaggaaccat    900
cgccaggcgt ccttggaaat ctcgccaata actttcctta ctgctcaaac actcttgatg    960
gaccttggac agtttctact gttttgtcat atctcttccc accaacatga tggcatggaa   1020
gcttatgtca agtagacag ctgtccagag aaccccaac tacgaatgaa aaataatgaa   1080
gaagcggaag actatgatga tgatcttact gattctgaaa tggatgtggt caggtttgat   1140
gatgacaact ctccttcctt tatccaaatt cgctcagttg ccaagaagca tcctaaaact   1200
tgggtacatt acattgctgc tgaagaggag gactgggact atgctcccctt agtcctcgcc   1260
cccgatgaca gaagttataa aagtcaatat ttgaacaatg gccctcagcg gattggtagg   1320
aagtacaaaa aagtccgatt tatggcatac acagatgaaa cctttaagac tcgtgaagct   1380
attcagcatg aatcaggaat cttgggacct ttactttatg gggaagttgg agacacactg   1440
ttgattatat ttaagaatca agcaagcaga ccatataaca tctaccctca cggaatcact   1500
gatgtccgtc ctttgtattc aaggagatta ccaaaaggtg taaaacattt gaaggatttt   1560
ccaattctgc caggagaaat attcaaatat aaatggacag tgactgtaga agatgggcca   1620
actaaatcag atcctcggtg cctgacccgc tattactcta gtttcgttaa tatgagagag   1680
gatctagctt caggactcat tggccctctc ctcatctgct acaaagaatc tgtagatcaa   1740
agaggaaacc agataatgtc agacaagagg aatgtcatcc tgttttctgt atttgatgag   1800
aaccgaagct ggtacctcac agagaatata caacgctttc tccccaatcc agctggagtg   1860
cagcttgagg atccagagtt ccaagcctcc aacatcatgc acagcatcaa tggctatgtt   1920
tttgatagtt tgcagttgtc agtttgtttg catgaggtgg catactggta cattctaagc   1980
attggagcac agactgactt cctttctgtc ttcttctctg gatataccctt caaacacaaa   2040
atggtctatg aagacacact caccctattc ccattctcag gagaaactgt cttcatgtcg   2100
atggaaaacc caggtctatg gattctgggg tgccacaact cagactttcg aacagaggc   2160
atgaccgcct tactgaaggt ttctagttgt gacaagaaca ctggtgatta ttacgaggac   2220
agttatgaag atatttcagc atacttgctg agtaaaaaca tgccattga accaagaagc   2280
ttctcccaga attcaagaca ccgtagcact aggcaaaagc aatttaatgc caccacaatt   2340
ccagaaaatg acatagagaa gactgacccct tggtttgcac acagaacacc tatgcctaaa   2400
atacaaaatg tctcctctag tgatttgttg atgctcttgc gacagagtcc tactccacat   2460
gggctatcct tatctgatct ccaagaagcc aaatatgaga cttttttctga tgatccatca   2520
cctggagcaa tagacagtaa taacagcctg tctgaaatga cacacttcag gccacagctc   2580
```

```
catcacagtg gggacatggt atttacccct gagtcaggcc tccaattaag attaaatgag    2640
aaactgggga caactgcagc aacagagttg aagaaacttg atttcaaagt ttctagtaca    2700
tcaaataatc tgatttcaac aattccatca gacaatttgg cagcaggtac tgataataca    2760
agttccttag acccccaag tatgccagtt cattatgata gtcaattaga taccactcta     2820
```

```
catcacagtg gggacatggt atttacccct gagtcaggcc tccaattaag attaaatgag    2640
aaactgggga caactgcagc aacagagttg aagaaacttg atttcaaagt ttctagtaca    2700
tcaaataatc tgatttcaac aattccatca gacaatttgg cagcaggtac tgataataca    2760
agttccttag acccccaag tatgccagtt cattatgata gtcaattaga taccactcta     2820
tttggcaaaa agtcatctcc ccttactgag tctggtggac ctctgagctt gagtgaagaa    2880
aataatgatt caaagttgtt agaatcaggt ttaatgaata gccaagaaag ttcatgggga    2940
aaaaatgtat cgtcaacaga gagtggtagg ttatttaaag ggaaaagagc tcatggacct    3000
gctttgttga ctaaagataa tgccttattc aaagttagca tctctttgtt aaagacaaac    3060
aaaacttcca ataattcagc aactaataga aagactcaca ttgatggccc atcattatta    3120
attgagaata gtccatcagt ctggcaaaat atattagaaa gtgacactga gtttaaaaaa    3180
gtgacacctt tgattcatga cagaatgctt atggacaaaa atgctacagc tttgaggcta    3240
aatcatatgt caaataaaac tacttcatca aaaacatgg aaatggtcca acagaaaaaa    3300
gagggcccca ttccaccaga tgcacaaaat ccagatatgt cgttctttaa gatgctattc    3360
ttgccagaat cagcaaggtg gatacaaagg actcatggaa agaactctct gaactctggg    3420
caaggcccca gtccaaagca attagtatcc ttaggaccag aaaaatctgt ggaaggtcag    3480
aatttcttgt ctgagaaaaa caaagtggta gtaggaaagg gtgaatttac aaaggacgta    3540
ggactcaaag agatggtttt tccaagcagc agaaacctat ttcttactaa cttggataat    3600
ttacatgaaa ataatacaca caatcaagaa aaaaaaattc aggaagaaat agaaagaag    3660 gaaacattaa tccaagagaa tgtagttttg cctcagatac atacagtgac tggcactaag    3720
aatttcatga agaacctttt cttactgagc actaggcaaa atgtagaagg ttcatatgac    3780
ggggcatatg ctccagtact tcaagatttt aggtcattaa atgattcaac aaatagaaca    3840
aagaaacaca cagctcattt ctcaaaaaaa ggggaggaag aaaacttgga aggcttggga    3900
aatcaaacca agcaaattgt agagaaatat gcatgcacca caaggatatc tcctaataca    3960
agccagcaga attttgtcac gcaacgtagt aagagagctt tgaaacaatt cagactccca    4020
ctagaagaaa cagaacttga aaaaaggata attgtggatg cacctcaac ccagtggtcc     4080 aaaaacatga acatttgac cccgagcacc ctcacacaga tagactacaa tgagaaggag    4140
aaaggggcca ttactcagtc tcccttatca gattgcctta cgaggagtca tagcatccct    4200
caagcaaata gatctccatt acccattgca aaggtatcat catttccatc tattagacct    4260
atatatctga ccagggtcct attccaagac aactcttctc atcttccagc agcatcttat    4320
agaaagaaag attctggggt ccaagaaagc agtcatttct acaaggagc caaaaaaaat    4380 aacctttctt tagccattct aaccttggag atgactggtg atcaaagaga ggttggctcc    4440
ctggggacaa gtgccacaaa ttcagtcaca tacaagaaag ttgagaacac tgttctcccg    4500
aaaccagact tgcccaaaac atctggcaaa gttgaattgc ttccaaaagt tcacattat    4560 cagaaggacc tattccctac ggaaactagc aatgggtctc ctggccatct ggatctcgtg    4620
gaagggagcc ttcttcaggg aacagaggga gcgattaagt ggaatgaagc aaacagacct    4680
ggaaaagttc cctttctgag agtagcaaca gaaagctctg caaagactcc ctccaagcta    4740
ttggatcctc ttgcttggga taaccactat ggtactcaga taccaaaaga agagtggaaa    4800
tcccaagaga agtcaccaga aaaaacagct tttaagaaaa aggataccat tttgtccctg    4860
aacgcttgtg aaagcaatca tgcaatagca gcaataaatg agggacaaaa taagcccgaa    4920
```

| | |
|---|---|
| atagaagtca cctgggcaaa gcaaggtagg actgaaaggc tgtgctctca aaacccacca | 4980 |
| gtcttgaaac gccatcaacg ggaaataact cgtactactc ttcagtcaga tcaagaggaa | 5040 |
| attgactatg atgataccat atcagttgaa atgaagaagg aagattttga catttatgat | 5100 |
| gaggatgaaa atcagagccc ccgcagcttt caaaagaaaa cacgacacta ttttattgct | 5160 |
| gcagtggaga ggctctggga ttatgggatg agtagctccc cacatgttct aagaaacagg | 5220 |
| gctcagagtg gcagtgtccc tcagttcaag aaagttgttt tccaggaatt tactgatggc | 5280 |
| tcctttactc agcccttata ccgtggagaa ctaaatgaac atttgggact cctggggcca | 5340 |
| tatataagag cagaagttga agataatatc atggtaactt tcagaaatca ggcctctcgt | 5400 |
| ccctattcct tctattctag ccttatttct tatgaggaag atcagaggca aggagcagaa | 5460 |
| cctagaaaaa actttgtcaa gcctaatgaa accaaaactt acttttggaa agtgcaacat | 5520 |
| catatggcac ccactaaaga tgagtttgac tgcaaagcct gggcttattt ctctgatgtt | 5580 |
| gacctgaaaa aagatgtgca ctcaggcctg attggacccc ttctggtctg ccacactaac | 5640 |
| acactgaacc ctgctcatgg gagacaagtg acagtacagg aatttgctct gttttttcacc | 5700 |
| atctttgatg agaccaaaag ctggtacttc actgaaaata tggaaagaaa ctgcagggct | 5760 |
| ccctgcaata tccagatgga agatcccact tttaaagaga attatcgctt ccatgcaatc | 5820 |
| aatggctaca taatggatac actacctggc ttagtaatgg ctcaggatca aaggattcga | 5880 |
| tggtatctgc tcagcatggg cagcaatgaa acatccatt ctattcattt cagtggacat | 5940 |
| gtgttcactg tacgaaaaaa agaggagtat aaaatggcac tgtacaatct ctatccaggt | 6000 |
| gttttttgaga cagtggaaat gttaccatcc aaagctggaa tttggcgggt ggaatgcctt | 6060 |
| attggcgagc atctacatgc tgggatgagc acacttttc tggtgtacag caataagtgt | 6120 |
| cagactcccc tggaatggc ttctggacac attagagatt ttcagattac agcttcagga | 6180 |
| caatatggac agtgggcccc aaagctggcc agacttcatt attccggatc aatcaatgcc | 6240 |
| tggagcacca aggagccctt ttcttggatc aaggtggatc tgttggcacc aatgattatt | 6300 |
| cacggcatca agacccaggg tgcccgtcag aagttctcca gcctctacat ctctcagttt | 6360 |
| atcatcatgt atagtcttga tgggaagaag tggcagactt atcgaggaaa ttccactgga | 6420 |
| accttaatgg tcttctttgg caatgtggat tcatctggga taaaacacaa tattttttaac | 6480 |
| cctccaatta ttgctcgata catccgtttg cacccaactc attatagcat tcgcagcact | 6540 |
| cttcgcatgg agttgatggg ctgtgattta aatagttgca gcatgccatt gggaatggag | 6600 |
| agtaaagcaa tatcagatgc acagattact gcttcatcct actttaccaa tatgtttgcc | 6660 |
| acctggtctc cttcaaaagc tcgacttcac ctccaaggga ggagtaatgc ctggagacct | 6720 |
| caggtgaata atccaaaaga gtggctgcaa gtggacttcc agaagacaat gaaagtcaca | 6780 |
| ggagtaacta ctcagggagt aaaatctctg cttaccagca tgtatgtgaa ggagttcctc | 6840 |
| atctccagca gtcaagatgg ccatcagtgg actctctttt ttcagaatgg caaagtaaag | 6900 |
| gtttttcagg gaaatcaaga ctccttcaca cctgtgtgta actctctaga cccaccgtta | 6960 |
| ctgactcgct accttcgaat tcaccccag agttgggtgc accagattgc cctgaggatg | 7020 |
| gaggttctgg gctgcgaggc acaggacctc tactga | 7056 |

<210> SEQ ID NO 2
<211> LENGTH: 2332
<212> TYPE: PRT
<213> ORGANISM: Homo sapiens

<400> SEQUENCE: 2

```
Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
            35                  40                  45

Thr Leu Phe Val Glu Phe Thr Asp His Leu Phe Asn Ile Ala Lys Pro
        50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
            115                 120                 125

Phe Pro Gly Gly Ser His Thr Tyr Val Trp Gln Val Leu Lys Glu Asn
130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
            165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
            195                 200                 205

His Ser Glu Thr Lys Asn Ser Leu Met Gln Asp Arg Asp Ala Ala Ser
210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
            245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
            275                 280                 285

Ser Pro Ile Thr Phe Leu Thr Ala Gln Thr Leu Leu Met Asp Leu Gly
            290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
            325                 330                 335

Met Lys Asn Asn Glu Glu Ala Glu Asp Tyr Asp Asp Leu Thr Asp
            340                 345                 350

Ser Glu Met Asp Val Val Arg Phe Asp Asp Asp Asn Ser Pro Ser Phe
            355                 360                 365

Ile Gln Ile Arg Ser Val Ala Lys Lys His Pro Lys Thr Trp Val His
        370                 375                 380

Tyr Ile Ala Ala Glu Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415
```

```
Gln Arg Ile Gly Arg Lys Tyr Lys Lys Val Arg Phe Met Ala Tyr Thr
                420                 425                 430
Asp Glu Thr Phe Lys Thr Arg Glu Ala Ile Gln His Glu Ser Gly Ile
            435                 440                 445
Leu Gly Pro Leu Leu Tyr Gly Glu Val Gly Asp Thr Leu Leu Ile Ile
        450                 455                 460
Phe Lys Asn Gln Ala Ser Arg Pro Tyr Asn Ile Tyr Pro His Gly Ile
465                 470                 475                 480
Thr Asp Val Arg Pro Leu Tyr Ser Arg Arg Leu Pro Lys Gly Val Lys
                485                 490                 495
His Leu Lys Asp Phe Pro Ile Leu Pro Gly Glu Ile Phe Lys Tyr Lys
            500                 505                 510
Trp Thr Val Thr Val Glu Asp Gly Pro Thr Lys Ser Asp Pro Arg Cys
        515                 520                 525
Leu Thr Arg Tyr Tyr Ser Ser Phe Val Asn Met Glu Arg Asp Leu Ala
        530                 535                 540
Ser Gly Leu Ile Gly Pro Leu Leu Ile Cys Tyr Lys Glu Ser Val Asp
545                 550                 555                 560
Gln Arg Gly Asn Gln Ile Met Ser Asp Lys Arg Asn Val Ile Leu Phe
                565                 570                 575
Ser Val Phe Asp Glu Asn Arg Ser Trp Tyr Leu Thr Glu Asn Ile Gln
            580                 585                 590
Arg Phe Leu Pro Asn Pro Ala Gly Val Gln Leu Glu Asp Pro Glu Phe
        595                 600                 605
Gln Ala Ser Asn Ile Met His Ser Ile Asn Gly Tyr Val Phe Asp Ser
        610                 615                 620
Leu Gln Leu Ser Val Cys Leu His Glu Val Ala Tyr Trp Tyr Ile Leu
625                 630                 635                 640
Ser Ile Gly Ala Gln Thr Asp Phe Leu Ser Val Phe Phe Ser Gly Tyr
                645                 650                 655
Thr Phe Lys His Lys Met Val Tyr Glu Asp Thr Leu Thr Leu Phe Pro
            660                 665                 670
Phe Ser Gly Glu Thr Val Phe Met Ser Met Glu Asn Pro Gly Leu Trp
        675                 680                 685
Ile Leu Gly Cys His Asn Ser Asp Phe Arg Asn Arg Gly Met Thr Ala
        690                 695                 700
Leu Leu Lys Val Ser Ser Cys Asp Lys Asn Thr Gly Asp Tyr Tyr Glu
705                 710                 715                 720
Asp Ser Tyr Glu Asp Ile Ser Ala Tyr Leu Leu Ser Lys Asn Asn Ala
                725                 730                 735
Ile Glu Pro Arg Ser Phe Ser Gln Asn Ser Arg His Pro Ser Thr Arg
            740                 745                 750
Gln Lys Gln Phe Asn Ala Thr Thr Ile Pro Glu Asn Asp Ile Glu Lys
        755                 760                 765
Thr Asp Pro Trp Phe Ala His Arg Thr Pro Met Pro Lys Ile Gln Asn
        770                 775                 780
Val Ser Ser Ser Asp Leu Leu Met Leu Leu Arg Gln Ser Pro Thr Pro
785                 790                 795                 800
His Gly Leu Ser Leu Ser Asp Leu Gln Glu Ala Lys Tyr Glu Thr Phe
                805                 810                 815
Ser Asp Asp Pro Ser Pro Gly Ala Ile Asp Ser Asn Asn Ser Leu Ser
            820                 825                 830
Glu Met Thr His Phe Arg Pro Gln Leu His His Ser Gly Asp Met Val
```

-continued

```
                835                840                845
Phe Thr Pro Glu Ser Gly Leu Gln Leu Arg Leu Asn Glu Lys Leu Gly
    850                855                860
Thr Thr Ala Ala Thr Glu Leu Lys Lys Leu Asp Phe Lys Val Ser Ser
865                870                875                880
Thr Ser Asn Asn Leu Ile Ser Thr Ile Pro Ser Asp Asn Leu Ala Ala
                885                890                895
Gly Thr Asp Asn Thr Ser Ser Leu Gly Pro Pro Ser Met Pro Val His
                900                905                910
Tyr Asp Ser Gln Leu Asp Thr Thr Leu Phe Gly Lys Lys Ser Ser Pro
                915                920                925
Leu Thr Glu Ser Gly Gly Pro Leu Ser Leu Ser Glu Glu Asn Asn Asp
    930                935                940
Ser Lys Leu Leu Glu Ser Gly Leu Met Asn Ser Gln Glu Ser Ser Trp
945                950                955                960
Gly Lys Asn Val Ser Ser Thr Glu Ser Gly Arg Leu Phe Lys Gly Lys
                965                970                975
Arg Ala His Gly Pro Ala Leu Leu Thr Lys Asp Asn Ala Leu Phe Lys
                980                985                990
Val Ser Ile Ser Leu Leu Lys Thr  Asn Lys Thr Ser Asn  Asn Ser Ala
    995                1000                1005
Thr Asn  Arg Lys Thr His Ile  Asp Gly Pro Ser Leu  Leu Ile Glu
    1010                1015                1020
Asn Ser  Pro Ser Val Trp  Gln Asn Ile Leu Glu Ser  Asp Thr Glu
    1025                1030                1035
Phe Lys  Lys Val Thr Pro  Leu Ile His Asp Arg Met  Leu Met Asp
    1040                1045                1050
Lys Asn  Ala Thr Ala Leu Arg  Leu Asn His Met Ser  Asn Lys Thr
    1055                1060                1065
Thr Ser  Ser Lys Asn Met Glu  Met Val Gln Gln Lys  Lys Glu Gly
    1070                1075                1080
Pro Ile  Pro Pro Asp Ala Gln  Asn Pro Asp Met Ser  Phe Phe Lys
    1085                1090                1095
Met Leu  Phe Leu Pro Glu Ser  Ala Arg Trp Ile Gln  Arg Thr His
    1100                1105                1110
Gly Lys  Asn Ser Leu Asn Ser  Gly Gln Gly Pro Ser  Pro Lys Gln
    1115                1120                1125
Leu Val  Ser Leu Gly Pro Glu  Lys Ser Val Glu Gly  Gln Asn Phe
    1130                1135                1140
Leu Ser  Glu Lys Asn Lys Val  Val Val Gly Lys Gly  Glu Phe Thr
    1145                1150                1155
Lys Asp  Val Gly Leu Lys Glu  Met Val Phe Pro Ser  Ser Arg Asn
    1160                1165                1170
Leu Phe  Leu Thr Asn Leu Asp  Asn Leu His Glu Asn  Asn Thr His
    1175                1180                1185
Asn Gln  Glu Lys Lys Ile Gln  Glu Glu Ile Glu Lys  Lys Glu Thr
    1190                1195                1200
Leu Ile  Gln Glu Asn Val Val  Leu Pro Gln Ile His  Thr Val Thr
    1205                1210                1215
Gly Thr  Lys Asn Phe Met Lys  Asn Leu Phe Leu Leu  Ser Thr Arg
    1220                1225                1230
Gln Asn  Val Glu Gly Ser Tyr  Asp Gly Ala Tyr Ala  Pro Val Leu
    1235                1240                1245
```

```
Gln Asp Phe Arg Ser Leu Asn Asp Ser Thr Asn Arg Thr Lys Lys
1250                1255                1260

His Thr Ala His Phe Ser Lys Lys Gly Glu Glu Glu Asn Leu Glu
1265                1270                1275

Gly Leu Gly Asn Gln Thr Lys Gln Ile Val Glu Lys Tyr Ala Cys
1280                1285                1290

Thr Thr Arg Ile Ser Pro Asn Thr Ser Gln Gln Asn Phe Val Thr
1295                1300                1305

Gln Arg Ser Lys Arg Ala Leu Lys Gln Phe Arg Leu Pro Leu Glu
1310                1315                1320

Glu Thr Glu Leu Glu Lys Arg Ile Ile Val Asp Asp Thr Ser Thr
1325                1330                1335

Gln Trp Ser Lys Asn Met Lys His Leu Thr Pro Ser Thr Leu Thr
1340                1345                1350

Gln Ile Asp Tyr Asn Glu Lys Glu Lys Gly Ala Ile Thr Gln Ser
1355                1360                1365

Pro Leu Ser Asp Cys Leu Thr Arg Ser His Ser Ile Pro Gln Ala
1370                1375                1380

Asn Arg Ser Pro Leu Pro Ile Ala Lys Val Ser Ser Phe Pro Ser
1385                1390                1395

Ile Arg Pro Ile Tyr Leu Thr Arg Val Leu Phe Gln Asp Asn Ser
1400                1405                1410

Ser His Leu Pro Ala Ala Ser Tyr Arg Lys Lys Asp Ser Gly Val
1415                1420                1425

Gln Glu Ser Ser His Phe Leu Gln Gly Ala Lys Lys Asn Asn Leu
1430                1435                1440

Ser Leu Ala Ile Leu Thr Leu Glu Met Thr Gly Asp Gln Arg Glu
1445                1450                1455

Val Gly Ser Leu Gly Thr Ser Ala Thr Asn Ser Val Thr Tyr Lys
1460                1465                1470

Lys Val Glu Asn Thr Val Leu Pro Lys Pro Asp Leu Pro Lys Thr
1475                1480                1485

Ser Gly Lys Val Glu Leu Leu Pro Lys Val His Ile Tyr Gln Lys
1490                1495                1500

Asp Leu Phe Pro Thr Glu Thr Ser Asn Gly Ser Pro Gly His Leu
1505                1510                1515

Asp Leu Val Glu Gly Ser Leu Leu Gln Gly Thr Glu Gly Ala Ile
1520                1525                1530

Lys Trp Asn Glu Ala Asn Arg Pro Gly Lys Val Pro Phe Leu Arg
1535                1540                1545

Val Ala Thr Glu Ser Ser Ala Lys Thr Pro Ser Lys Leu Leu Asp
1550                1555                1560

Pro Leu Ala Trp Asp Asn His Tyr Gly Thr Gln Ile Pro Lys Glu
1565                1570                1575

Glu Trp Lys Ser Gln Glu Lys Ser Pro Glu Lys Thr Ala Phe Lys
1580                1585                1590

Lys Lys Asp Thr Ile Leu Ser Leu Asn Ala Cys Glu Ser Asn His
1595                1600                1605

Ala Ile Ala Ala Ile Asn Glu Gly Gln Asn Lys Pro Glu Ile Glu
1610                1615                1620

Val Thr Trp Ala Lys Gln Gly Arg Thr Glu Arg Leu Cys Ser Gln
1625                1630                1635
```

```
Asn Pro Pro Val Leu Lys Arg His Gln Arg Glu Ile Thr Arg Thr
1640                1645                1650

Thr Leu Gln Ser Asp Gln Glu Glu Ile Asp Tyr Asp Asp Thr Ile
    1655                1660                1665

Ser Val Glu Met Lys Lys Glu Asp Phe Asp Ile Tyr Asp Glu Asp
    1670                1675                1680

Glu Asn Gln Ser Pro Arg Ser Phe Gln Lys Lys Thr Arg His Tyr
    1685                1690                1695

Phe Ile Ala Ala Val Glu Arg Leu Trp Asp Tyr Gly Met Ser Ser
    1700                1705                1710

Ser Pro His Val Leu Arg Asn Arg Ala Gln Ser Gly Ser Val Pro
    1715                1720                1725

Gln Phe Lys Lys Val Val Phe Gln Glu Phe Thr Asp Gly Ser Phe
    1730                1735                1740

Thr Gln Pro Leu Tyr Arg Gly Glu Leu Asn Glu His Leu Gly Leu
    1745                1750                1755

Leu Gly Pro Tyr Ile Arg Ala Glu Val Glu Asp Asn Ile Met Val
    1760                1765                1770

Thr Phe Arg Asn Gln Ala Ser Arg Pro Tyr Ser Phe Tyr Ser Ser
    1775                1780                1785

Leu Ile Ser Tyr Glu Glu Asp Gln Arg Gln Gly Ala Glu Pro Arg
    1790                1795                1800

Lys Asn Phe Val Lys Pro Asn Glu Thr Lys Thr Tyr Phe Trp Lys
    1805                1810                1815

Val Gln His His Met Ala Pro Thr Lys Asp Glu Phe Asp Cys Lys
    1820                1825                1830

Ala Trp Ala Tyr Phe Ser Asp Val Asp Leu Glu Lys Asp Val His
    1835                1840                1845

Ser Gly Leu Ile Gly Pro Leu Leu Val Cys His Thr Asn Thr Leu
    1850                1855                1860

Asn Pro Ala His Gly Arg Gln Val Thr Val Gln Glu Phe Ala Leu
    1865                1870                1875

Phe Phe Thr Ile Phe Asp Glu Thr Lys Ser Trp Tyr Phe Thr Glu
    1880                1885                1890

Asn Met Glu Arg Asn Cys Arg Ala Pro Cys Asn Ile Gln Met Glu
    1895                1900                1905

Asp Pro Thr Phe Lys Glu Asn Tyr Arg Phe His Ala Ile Asn Gly
    1910                1915                1920

Tyr Ile Met Asp Thr Leu Pro Gly Leu Val Met Ala Gln Asp Gln
    1925                1930                1935

Arg Ile Arg Trp Tyr Leu Leu Ser Met Gly Ser Asn Glu Asn Ile
    1940                1945                1950

His Ser Ile His Phe Ser Gly His Val Phe Thr Val Arg Lys Lys
    1955                1960                1965

Glu Glu Tyr Lys Met Ala Leu Tyr Asn Leu Tyr Pro Gly Val Phe
    1970                1975                1980

Glu Thr Val Glu Met Leu Pro Ser Lys Ala Gly Ile Trp Arg Val
    1985                1990                1995

Glu Cys Leu Ile Gly Glu His Leu His Ala Gly Met Ser Thr Leu
    2000                2005                2010

Phe Leu Val Tyr Ser Asn Lys Cys Gln Thr Pro Leu Gly Met Ala
    2015                2020                2025

Ser Gly His Ile Arg Asp Phe Gln Ile Thr Ala Ser Gly Gln Tyr
```

Gly Gln Trp Ala Pro Lys Leu Ala Arg Leu His Tyr Ser Gly Ser
            2045                2050                2055

Ile Asn Ala Trp Ser Thr Lys Glu Pro Phe Ser Trp Ile Lys Val
2060                2065                2070

Asp Leu Leu Ala Pro Met Ile Ile His Gly Ile Lys Thr Gln Gly
    2075                2080                2085

Ala Arg Gln Lys Phe Ser Ser Leu Tyr Ile Ser Gln Phe Ile Ile
    2090                2095                2100

Met Tyr Ser Leu Asp Gly Lys Lys Trp Gln Thr Tyr Arg Gly Asn
    2105                2110                2115

Ser Thr Gly Thr Leu Met Val Phe Phe Gly Asn Val Asp Ser Ser
    2120                2125                2130

Gly Ile Lys His Asn Ile Phe Asn Pro Pro Ile Ile Ala Arg Tyr
    2135                2140                2145

Ile Arg Leu His Pro Thr His Tyr Ser Ile Arg Ser Thr Leu Arg
    2150                2155                2160

Met Glu Leu Met Gly Cys Asp Leu Asn Ser Cys Ser Met Pro Leu
    2165                2170                2175

Gly Met Glu Ser Lys Ala Ile Ser Asp Ala Gln Ile Thr Ala Ser
    2180                2185                2190

Ser Tyr Phe Thr Asn Met Phe Ala Thr Trp Ser Pro Ser Lys Ala
    2195                2200                2205

Arg Leu His Leu Gln Gly Arg Ser Asn Ala Trp Arg Pro Gln Val
    2210                2215                2220

Asn Asn Pro Lys Glu Trp Leu Gln Val Asp Phe Gln Lys Thr Met
    2225                2230                2235

Lys Val Thr Gly Val Thr Thr Gln Gly Val Lys Ser Leu Leu Thr
    2240                2245                2250

Ser Met Tyr Val Lys Glu Phe Leu Ile Ser Ser Ser Gln Asp Gly
    2255                2260                2265

His Gln Trp Thr Leu Phe Phe Gln Asn Gly Lys Val Lys Val Phe
    2270                2275                2280

Gln Gly Asn Gln Asp Ser Phe Thr Pro Val Val Asn Ser Leu Asp
    2285                2290                2295

Pro Pro Leu Leu Thr Arg Tyr Leu Arg Ile His Pro Gln Ser Trp
    2300                2305                2310

Val His Gln Ile Ala Leu Arg Met Glu Val Leu Gly Cys Glu Ala
    2315                2320                2325

Gln Asp Leu Tyr
    2330

<210> SEQ ID NO 3
<211> LENGTH: 9720
<212> TYPE: DNA
<213> ORGANISM: Artificial Sequence
<220> FEATURE:
<223> OTHER INFORMATION: pAAV-CB-hBDD-F8-X10

<400> SEQUENCE: 3
aattcccatc atcaataata taccttattt tggattgaag ccaatatgat aatgagggggg    60 tggagtttgt gacgtggcgc ggggcgtggg aacgggcgg gtgacgtagt agtctctaga    120 ggtcccagc gaccttgacg ggcatctgcc cggcatttct gacagctttg tgaactgggt    180
ggccgagaag gaatgggagt tgccgccaga ttctgacatg gatctgaatc tgattgagca    240

```
ggcacccctg accgtggccg agaagctgca tcgctggcgt aatagcgaag aggcccgcac    300
cgatcgccct tcccaacagt tgcgcagcct gaatggcgaa tggaattcca gacgattgag    360
cgtcaaaatg taggtatttc catgagcgtt tttcctgttg caatggctgg cggtaatatt    420
gttctggata ttaccagcaa ggccgatagt ttgagttctt ctactcaggc aagtgatgtt    480
attactaatc aaagaagtat tgcgacaacg gttaatttgc gtgatggaca gactctttta    540
ctcggtggcc tcactgatta taaaaacact tctcaggatt ctggcgtacc gttcctgtct    600
aaaatccctt aatcggcct cctgtttagc tcccgctctg attctaacga ggaaagcacg    660
ttatacgtgc tcgtcaaagc aaccatagta cgcgccctgt agcggcgcat taagcgcggc    720
gggtgtggtg gttacgcgca gcgtgaccgc tacacttgcc agcgccctag cgcccgctcc    780
tttcgctttc ttcccttcct ttctcgccac gttcgccggc tttccccgtc aagctctaaa    840 tcggggggctc cctttagggt tccgatttag tgctttacgg cacctcgacc ccaaaaaact    900
tgattagggt gatggttcac gtagtgggcc atcgccctga tagacggttt ttcgcccttt    960
gacgttggag tccacgttct ttaatagtgg actcttgttc caaactggaa caacactcaa   1020
ccctatctcg gtctattctt ttgatttata agggattttg ccgatttcgg cctattggtt   1080
aaaaaatgag ctgatttaac aaaaatttaa cgcgaatttt aacaaaatat taacgtttac   1140
aatttaaata tttgcttata caatcttcct gttttggggg cttttctgat tatcaaccgg   1200
ggtacatatg attgacatgc tagttttacg attaccgttc atcgcctgca ggggggggggg   1260 gggggggggtt ggccactccc tctctgcgcg ctcgctcgct cactgaggcc gggcgaccaa   1320
aggtcgcccg acgcccgggc tttgcccggg cggcctcagt gagcgagcga gcgcgcagag   1380
agggagtggc caactccatc actagggggtt cctagatctg aattcggtac gtacctctgg   1440
tcgttacata acttacggta aatggcccgc ctggctgacc gcccaacgac cccgcccatt   1500
gacgtcaata atgacgtatg ttcccatagt aacgccaata gggactttcc attgacgtca   1560
atgggtggag tatttacggt aaactgccca cttggcagta catcaagtgt atcatatgcc   1620
aagtacgccc cctattgacg tcaatgacgg taaatggccc gcctggcatt atgcccagta   1680
catgacctta tgggactttc ctacttggca gtacatctac tcgaggccac gttctgcttc   1740
actctcccca tctccccccc ctccccaccc ccaattttgt atttatttat tttttaatta   1800
ttttgtgcag cgatggggc gggggggggg gggggggggg cgcgcgccag gcggggcggg   1860
gcggggcgag gggcggggcg gggcgaggcg gagaggtgcg gcggcagcca atcagagcgg   1920
cgcgctccga aagtttcctt ttatggcgag gcggcggcgg cggcggccct ataaaaagcg   1980
aagcgcgcgg cgggcgggag cgggatcagc caccgcggtg gcggcctaga gtcgacgagg   2040
aactgaaaaa ccagaaagtt aactggtaag tttagtcttt tgtcttttta tttcaggtcc   2100
cggatccggt ggtggtgcaa atcaaagaac tgctcctcag tggatgttgc ctttacttct   2160
aggcctgtac ggaagtgtta cttctgctct aaaagctgcg gaattgtacc cgcggccgct   2220
tttcaaaatg caaatagagc tctccacctg cttctttctg tgccttttgc gattctgctt   2280
tagtgccacc agaagatact acctgggtgc agtggaactg tcatgggact atatgcaaag   2340
tgatctcggt gagctgcctg tggacgcaag atttcctcct agagtgccaa atctttttcc   2400
attcaacacc tcagtcgtgt acaaaaagac tctgtttgta gaattcacgg atcacctttt   2460
caacatcgct aagccaaggc caccctggat gggtctgcta ggtcctacca tccaggctga   2520
ggtttacgac acggtggtcg ttaccctgaa gaacatggct tctcatcccg ttagtcttca   2580
```

```
cgctgtcggc gtctccttct ggaaatcttc cgaaggcgct gaatatgagg atcacaccag    2640
ccaaagggag aaggaagacg ataaagtcct tcccggtaaa agccaaacct acgtctggca    2700
ggtcctgaaa gaaaatggtc caacagcctc tgacccacca tgtcttacct actcatacct    2760
gtctcacgtg gacctggtga aagacctgaa ttcgggcctc attggagccc tactagtatg    2820
tagagaaggg agtctggcca aggaaaagac acagaccttg cacaaattta tactactttt    2880
tgctgtattt gatgaaggga aaagttggca ctcagaaaca aagaactcct tgatgcagga    2940
tagggatgct gcatctgctc gggcctggcc taaaatgcac acagtcaatg gttatgtaaa    3000
caggtctctg ccaggtctga ttggatgcca caggaaatca gtctattggc atgtgattgg    3060
aatgggcacc actcctgaag tgcactcaat attcctcgaa ggtcacacat tcttgtgag    3120 gaaccatcgc caggcgtcct tggaaatctc gccaataact ttccttactg ctcaaacact    3180
cttgatggac cttggacagt ttctactgtt ttgtcatatc tcttcccacc aacatgatgg    3240
catggaagct tatgtcaaag tagacagctg tccagaggaa ccccaactac gaatgaaaaa    3300
taatgaagaa gcggaagact atgatgatga tcttactgat tctgaaatgg atgtggtcag    3360
gtttgatgat gacaactctc cttcctttat ccaaattcgc tcagttgcca agaagcatcc    3420
taaaacttgg gtacattaca ttgctgctga agaggaggac tgggactatg ctcccttagt    3480
cctcgccccc gatgacagaa gttataaaag tcaatatttg aacaatggcc ctcagcggat    3540
tggtaggaag tacaaaaaag tccgatttat ggcatacaca gatgaaacct ttaagactcg    3600
tgaagctatt cagcatgaat caggaatctt gggacctta ctttatgggg aagttggaga    3660
cacactgttg attatattta agaatcaagc aagcagacca tataacatct accctcacgg    3720
aatcactgat gtccgtcctt tgtattcaag gagattacca aaggtgtaa acatttgaa    3780 ggatttttcca attctgccag gagaaatatt caaatataaa tggacagtga ctgtagaaga    3840
tgggccaact aaatcagatc ctcggtgcct gacccgctat tactctagtt tcgttaatat    3900
ggagagagat ctagcttcag gactcattgg ccctctcctc atctgctaca agaatctgt    3960 agatcaaaga ggaaaccaga taatgtcaga caagaggaat gtcatcctgt tttctgtatt    4020
tgatgagaac cgaagctggt acctcacaga gaatatacaa cgctttctcc ccaatccagc    4080
tggagtgcag cttgaggatc cagagttcca agcctccaac atcatgcaca gcatcaatgg    4140
ctatgttttt gatagtttgc agttgtcagt ttgtttgcat gaggtggcat actggtacat    4200
tctaagcatt ggagcacaga ctgacttcct ttctgtcttc ttctctggat ataccttcaa    4260
acacaaaatg gtctatgaag acacactcac cctattccca ttctcaggag aaactgtctt    4320
catgtcgatg gaaaacccag gtctatggat tctggggtgc cacaactcag actttcggaa    4380
cagaggcatg accgccttac tgaaggtttc tagttgtgac aagaacactg gtgattatta    4440
cgaggacagt tatgaagata tttcagcata cttgctgagt aaaaacaatg ccattgaacc    4500
aagaagcttc tcccagaatt caagacaccc tagcactagg caaaagcaat taatgccac    4560 cacaccacca gtcttgaaac gccatcaacg cgaaataact cgtactactc ttcagtcaga    4620
tcaagaggaa attgactatg atgataccat atcagttgaa atgaagaagg aagattttga    4680
catttatgat gaggatgaaa atcagagccc ccgcagcttt caaaagaaaa cacgacacta    4740
ttttattgct gcagtggaga ggctctggga ttatgggatg agtagctccc cacatgttct    4800
aagaaacagg gctcagagtg gcagtgtccc tcagttcaag aaagttgttt ccaggaatt    4860 tactgatggc tcctttactc agcccttata ccgtggagaa ctaaatgaac atttgggact    4920
cctggggcca tatataagag cagaagttga agataatatc atggtaactt tcagaaatca    4980
```

```
ggcctctcgt ccctattcct tctattctag ccttatttct tatgaggaag atcagaggca   5040
aggagcagaa cctagaaaaa actttgtcaa gcctaatgaa accaaaactt acttttggaa   5100
agtgcaacat catatggcac ccactaaaga tgagtttgac tgcaaagcct gggcttattt   5160
ctctgatgtt gacctggaaa agatgtgca ctcaggcctg attggacccc ttctggtctg    5220
ccacactaac acactgaacc ctgctcatgg gagacaagtg acagtacagg aatttgctct   5280 gttttttcacc atctttgatg agaccaaaag ctggtacttc actgaaaata tggaaagaaa   5340
ctgcagggct ccctgcaata tccagatgga agatcccact tttaaagaga attatcgctt   5400
ccatgcaatc aatggctaca taatggatac actacctggc ttagtaatgg ctcaggatca   5460
aaggattcga tggtatctgc tcagcatggg cagcaatgaa acatccatt ctattcattt    5520 cagtggacat gtgttcactg tacgaaaaaa agaggagtat aaaatggcac tgtacaatct   5580
ctatccaggt gtttttgaga cagtggaaat gttaccatcc aaagctggaa tttggcgggt   5640
ggaatgcctt attggcgagc atctacatgc tgggatgagc acactttttc tggtgtacag   5700
caataagtgt cagactcccc tgggaatggc ttctggacac attagagatt ttcagattac   5760
agcttcagga caatatggac agtgggcccc aaagctggcc agacttcatt attccggatc   5820
aatcaatgcc tggagcacca aggagccctt tcttggatc aaggtggatc tgttggcacc    5880
aatgattatt cacggcatca agacccaggg tgcccgtcag aagttctcca gcctctacat   5940
ctctcagttt atcatcatgt atagtcttga tgggaagaag tggcagactt atcgaggaaa   6000
ttccactgga accttaatgg tcttctttgg caatgtggat tcatctggga taaaacacaa   6060
tatttttaac cctccaatta ttgctcgata catccgtttg cacccaactc attatagcat   6120
tcgcagcact cttcgcatgg agttgatggg ctgtgattta aatagttgca gcatgccatt   6180
gggaatggag agtaaagcaa tatcagatgc acagattact gcttcatcct actttaccaa   6240
tatgtttgcc acctggtctc cttcaaaagc tcgacttcac ctccaaggga ggagtaatgc   6300
ctggagacct caggtgaata atccaaaaga gtggctgcaa gtggacttcc agaagacaat   6360
gaaagtcaca ggagtaacta ctcagggagt aaaatctctg cttaccagca tgtatgtgaa   6420
ggagttcctc atctccagca gtcaagatgg ccatcagtgg actctctttt ttcagaatgg   6480
caaagtaaag gttttttcagg gaaatcaaga ctccttcaca cctgtggtga actctctaga   6540
cccaccgtta ctgactcgct accttcgaat tcaccccag agttgggtgc accagattgc    6600
cctgaggatg gaggttctgg gctgcgaggc acaggacctc tactgacaat tgacgctgat   6660
cagcctcgac tgtgccttct agttgccagc catctgttgt ttgcccctcc ccgtgccttt   6720
ccttgaccct ggaaggtgcc actcccactg tcctttccta ataaaatgag gaaattgcat   6780
cgcattgtct gagtaggtgt cattctattc tggggggtgg ggtggggcag acagcaagg    6840 gggaggattg ggaagacaat agcaggcatg ctggggagag atctaggaac ccctagtgat   6900
ggagttggcc actccctctc tgcgcgctcg ctcgctcact gaggccgccc gggcaaagcc   6960
cgggcgtcgg gcgacctttg gtcgcccggc ctcagtgagc gagcgagcgc gcagagaggg   7020
agtggccaac ccccccccc cccccctgc aggcgattct cttgtttgct ccagactctc     7080
aggcaatgac ctgatagcct tgtagagac ctctcaaaaa tagctaccct ctccggcatg    7140
aatttatcag ctagaacggt tgaatatcat attgatggtg atttgactgt ctccggcctt   7200
tctcacccgt ttgaatcttt acctacacat tactcaggca ttgcatttaa aatatatgag   7260
ggttctaaaa attttttatcc ttgcgttgaa ataaaggctt ctcccgcaaa agtattacag   7320
```

```
ggtcataatg ttttggtac aaccgattta gctttatgct ctgaggcttt attgcttaat    7380
tttgctaatt ctttgccttg cctgtatgat ttattggatg ttggaattcc tgatgcggta    7440
ttttctcctt acgcatctgt gcggtatttc acaccgcata tggtgcactc tcagtacaat    7500
ctgctctgat gccgcatagt taagccagcc ccgacacccg ccaacacccg ctgacgcgcc    7560
ctgacgggct tgtctgctcc cggcatccgc ttacagacaa gctgtgaccg tctccgggag    7620
ctgcatgtgt cagaggtttt caccgtcatc accgaaacgc gcgagacgaa agggcctcgt    7680
gatacgccta ttttataggt taatgtcat gataataatg gtttcttaga cgtcaggtgg    7740
cacttttcgg ggaaatgtgc gcggaacccc tatttgttta ttttctaaa tacattcaaa    7800 tatgtatccg ctcatgagac aataaccctg ataaatgctt caataatatt gaaaaaggaa    7860
gagtatgagt attcaacatt tccgtgtcgc ccttattccc ttttttgcgg cattttgcct    7920
tcctgttttt gctcacccag aaacgctggt gaaagtaaaa gatgctgaag atcagttggg    7980
tgcacgagtg ggttacatcg aactggatct caacagcggt aagatccttg agagttttcg    8040
ccccgaagaa cgttttccaa tgatgagcac ttttaaagtt ctgctatgtg gcgcggtatt    8100
atcccgtatt gacgccgggc aagagcaact cggtcgccgc atacactatt ctcagaatga    8160
cttggttgag tactcaccag tcacagaaaa gcatcttacg gatggcatga cagtaagaga    8220
attatgcagt gctgccataa ccatgagtga taacactgcg gccaacttac ttctgacaac    8280
gatcggagga ccgaaggagc taaccgcttt tttgcacaac atgggggatc atgtaactcg    8340
ccttgatcgt tgggaaccgg agctgaatga agccatacca aacgacgagc gtgacaccac    8400
gatgcctgta gcaatggcaa caacgttgcg caaactatta actggcgaac tacttactct    8460
agcttcccgg caacaattaa tagactggat ggaggcggat aaagttgcag gaccacttct    8520
gcgctcggcc cttccggctg gctggtttat tgctgataaa tctggagccg gtgagcgtgg    8580
gtctcgcggt atcattgcag cactggggcc agatggtaag ccctcccgta tcgtagttat    8640
ctacacgacg gggagtcagg caactatgga tgaacgaaat agacagatcg ctgagatagg    8700
tgcctcactg attaagcatt ggtaactgtc agaccaagtt tactcatata ctttagat    8760 tgatttaaaa cttcattttt aatttaaaag gatctaggtg aagatccttt ttgataatct    8820
catgaccaaa atcccttaac gtgagttttc gttccactga gcgtcagacc ccgtagaaaa    8880
gatcaaagga tcttcttgag atccttttt tctgcgcgta atctgctgct tgcaaacaaa    8940
aaaaccaccg ctaccagcgg tggtttgttt gccggatcaa gagctaccaa ctctttttcc    9000
gaaggtaact ggcttcagca gagcgcagat accaaatact gtccttctag tgtagccgta    9060
gttaggccac cacttcaaga actctgtagc accgcctaca tacctcgctc tgctaatcct    9120
gttaccagtg gctgctgcca gtggcgataa gtcgtgtctt accgggttgg actcaagacg    9180
atagttaccg gataaggcgc agcggtcggg ctgaacgggg ggttcgtgca cacagcccag    9240
cttggagcga acgacctaca ccgaactgag atacctacag cgtgagctat gagaaagcgc    9300
cacgcttccc gaagggagaa aggcggacag gtatccggta agcggcaggg tcggaacagg    9360
agagcgcacg agggagcttc caggggggaaa cgcctggtat ctttatagtc ctgtcgggtt    9420
tcgccacctc tgacttgagc gtcgattttt gtgatgctcg tcaggggggc ggagcctatg    9480
gaaaaacgcc agcaacgcgg ccttttacg gttcctggcc ttttgctggc cttttgctca    9540
catgttcttt cctgcgttat cccctgattc tgtggataac cgtattaccg cctttgagtg    9600
agctgatacc gctcgccgca gccgaacgac cgagcgcagc gagtcagtga gcgaggaagc    9660
ggaagagcgc ccaatacgca aaccgcctct ccccgcgcgt tggccgattc attaatgcag    9720
```

<210> SEQ ID NO 4
<211> LENGTH: 9720
<212> TYPE: DNA
<213> ORGANISM: Artificial Sequence
<220> FEATURE:
<223> OTHER INFORMATION: pAAV-CB-hBB-F8-X5

<400> SEQUENCE: 4

| | | | | | |
|---|---|---|---|---|---|
| aattcccatc | atcaataata | taccttattt | tggattgaag | ccaatatgat | aatgaggggg | 60 |
| tggagtttgt | gacgtggcgc | ggggcgtggg | aacggggcgg | gtgacgtagt | agtctctaga | 120 |
| ggtccccagc | gaccttgacg | ggcatctgcc | cggcatttct | gacagctttg | tgaactgggt | 180 |
| ggccgagaag | gaatgggagt | tgccgccaga | ttctgacatg | gatctgaatc | tgattgagca | 240 |
| ggcaccctg | accgtggccg | agaagctgca | tcgctggcgt | aatagcgaag | aggcccgcac | 300 |
| cgatcgccct | tcccaacagt | tgcgcagcct | gaatggcgaa | tggaattcca | gacgattgag | 360 |
| cgtcaaaatg | taggtatttc | catgagcgtt | tttcctgttg | caatggctgg | cggtaatatt | 420 |
| gttctggata | ttaccagcaa | ggccgatagt | ttgagttctt | ctactcaggc | aagtgatgtt | 480 |
| attactaatc | aaagaagtat | tgcgacaacg | gttaatttgc | gtgatggaca | gactcttta | 540 |
| ctcggtggcc | tcactgatta | taaaaacact | tctcaggatt | ctggcgtacc | gttcctgtct | 600 |
| aaaatccctt | taatcggcct | cctgtttagc | tcccgctctg | attctaacga | ggaaagcacg | 660 |
| ttatacgtgc | tcgtcaaagc | aaccatagta | cgcgccctgt | agcggcgcat | taagcgcggc | 720 |
| gggtgtggtg | gttacgcgca | gcgtgaccgc | tacacttgcc | agcgccctag | cgcccgctcc | 780 |
| tttcgctttc | ttcccttcct | ttctcgccac | gttcgccggc | tttccccgtc | aagctctaaa | 840 |
| tcggggctc | cctttagggt | tccgatttag | tgctttacgg | cacctcgacc | ccaaaaaact | 900 |
| tgattagggt | gatggttcac | gtagtgggcc | atcgccctga | tagacggttt | ttcgcccttt | 960 |
| gacgttggag | tccacgttct | ttaatagtgg | actcttgttc | caaactggaa | caacactcaa | 1020 |
| ccctatctcg | gtctattctt | ttgatttata | agggattttg | ccgatttcgg | cctattggtt | 1080 |
| aaaaaatgag | ctgatttaac | aaaaatttaa | cgcgaatttt | aacaaaatat | taacgtttac | 1140 |
| aatttaaata | tttgcttata | caatcttcct | gttttggggg | cttttctgat | tatcaaccgg | 1200 |
| ggtacatatg | attgacatgc | tagttttacg | attaccgttc | atcgcctgca | gggggggggg | 1260 |
| ggggggggtt | ggccactccc | tctctgcgcg | ctcgctcgct | cactgaggcc | gggcgaccaa | 1320 |
| aggtcgcccg | acgcccgggc | tttgcccggg | cggcctcagt | gagcgagcga | gcgcgcagag | 1380 |
| agggagtggc | caactccatc | actagggtt | cctagatctg | aattcggtac | gtacctctgg | 1440 |
| tcgttacata | acttacggta | aatggcccgc | ctggctgacc | gcccaacgac | ccgcccatt | 1500 |
| gacgtcaata | atgacgtatg | ttcccatagt | aacgccaata | gggactttcc | attgacgtca | 1560 |
| atgggtggag | tatttacggt | aaactgccca | cttggcagta | catcaagtgt | atcatatgcc | 1620 |
| aagtacgccc | cctattgacg | tcaatgacgg | taaatggccc | gcctggcatt | atgcccagta | 1680 |
| catgacctta | tgggactttc | ctacttggca | gtacatctac | tcgaggccac | gttctgcttc | 1740 |
| actctcccca | tctcccccc | ctccccaccc | ccaattttgt | atttatttat | tttttaatta | 1800 |
| ttttgtgcag | cgatggggc | gggggggggg | gggggggggg | cgcgcgccag | gcggggcggg | 1860 |
| gcggggcgag | gggcggggcg | gggcgaggcg | gagaggtgcg | gcggcagcca | atcagagcgg | 1920 |
| cgcgctccga | aagtttcctt | ttatggcgag | gcggcggcgg | cggcggccct | ataaaaagcg | 1980 |
| aagcgcgcgg | cgggcgggag | cgggatcagc | caccgcggtg | gcggcctaga | gtcgacgagg | 2040 |

```
aactgaaaaa ccagaaagtt aactggtaag tttagtcttt ttgtctttta tttcaggtcc    2100
cggatccggt ggtggtgcaa atcaaagaac tgctcctcag tggatgttgc ctttacttct    2160
aggcctgtac ggaagtgtta cttctgctct aaaagctgcg gaattgtacc cgcggccgct    2220
tttcaaaatg caaatagagc tctccacctg cttctttctg tgccttttgc gattctgctt    2280
tagtgccacc agaagatact acctgggtgc agtggaactg tcatgggact atatgcaaag    2340
tgatctcggt gagctgcctg tggacgcaag atttcctcct agagtgccaa aatcttttcc    2400
attcaacacc tcagtcgtgt acaaaaagac tctgtttgta gaattcacgg atcaccttt    2460 caacatcgct aagccaaggc caccctggat gggtctgcta ggtcctacca tccaggctga    2520
ggtttatgat acagtggtcg ttacacttaa gaacatggct tcccatcctg tcagtcttca    2580
tgctgttggt gtatcctact ggaaatcttc tgagggagct gaatatgatg atcagaccag    2640
tcaaagggag aaagaagatg ataaagtctt ccctggtaaa agccatacat atgtctggca    2700
ggtcctgaaa gagaatggtc caacagcctc tgacccacca tgccttacct actcatatct    2760
ttctcatgtg gacctggtaa aagacttgaa ttcaggcctc attggagccc tactagtatg    2820
tagagaaggg agtctggcca aggaaaagac acagaccttg cacaaattta tactactttt    2880
tgctgtattt gatgaaggga aaagttggca ctcagaaaca aagaactcct tgatgcagga    2940
tagggatgct gcatctgctc gggcctggcc taaaatgcac acagtcaatg gttatgtaaa    3000
caggtctctg ccaggtctga ttggatgcca caggaaatca gtctattggc atgtgattgg    3060
aatgggcacc actcctgaag tgcactcaat attcctcgaa ggtcacacat tcttgtgag    3120 gaaccatcgc caggcgtcct tggaaatctc gccaataact ttccttactg ctcaaacact    3180
cttgatggac cttggacagt ttctactgtt ttgtcatatc tcttcccacc aacatgatgg    3240 catgaagct tatgtcaaag tagacagctg tccagaggaa ccccaactac gaatgaaaaa    3300
taatgaagaa gcggaagact atgatgatga tcttactgat tctgaaatgg atgtggtcag    3360
gtttgatgat gacaactctc cttcctttat ccaaattcgc tcagttgcca agaagcatcc    3420
taaaacttgg gtacattaca ttgctgctga agaggaggac tgggactatg ctcccttagt    3480
cctcgccccc gatgacagaa gttataaaag tcaatatttg aacaatggcc ctcagcggat    3540
tggtaggaag tacaaaaaag tccgatttat ggcatacaca gatgaaacct ttaagactcg    3600
tgaagctatt cagcatgaat caggaatctt gggacctta cttatgggg aagttggaga    3660 cacactgttg attatatta agaatcaagc aagcagacca tataacatct accctcacgg    3720
aatcactgat gtccgtcctt tgtattcaag gagattacca aaaggtgtaa acatttgaa    3780 ggatttttca attctgccag gagaaatatt caaatataaa tggacagtga ctgtagaaga    3840
tgggccaact aaatcagatc ctcggtgcct gacccgctat tactctagtt tcgttaatat    3900
ggagagagat ctagcttcag gactcattgg ccctctcctc atctgctaca agaatctgt    3960 agatcaaaga ggaaaccaga taatgtcaga caagaggaat gtcatcctgt tttctgtatt    4020
tgatgagaac cgaagctggt acctcacaga gaatatacaa cgctttctcc ccaatccagc    4080
tggagtgcag cttgaggatc cagagttcca agcctccaac atcatgcaca gcatcaatgg    4140
ctatgttttt gatagtttgc agttgtcagt ttgtttgcat gaggtggcat actggtacat    4200
tctaagcatt ggagcacaga ctgacttcct ttctgtcttc ttctctggat ataccttcaa    4260
acacaaaatg gtctatgaag acacactcac cctattccca ttctcaggag aaactgtctt    4320
catgtcgatg gaaaacccag gtctatggat tctggggtgc cacaactcag actttcggaa    4380
cagaggcatg accgccttac tgaaggtttc tagttgtgac aagaacactg gtgattatta    4440
```

```
cgaggacagt tatgaagata tttcagcata cttgctgagt aaaaacaatg ccattgaacc    4500
aagaagcttc tcccagaatt caagacaccc tagcactagg caaaagcaat ttaatgccac    4560
cacaccacca gtcttgaaac gccatcaacg cgaaataact cgtactactc ttcagtcaga    4620
tcaagaggaa attgactatg atgataccat atcagttgaa atgaagaagg aagattttga    4680
catttatgat gaggatgaaa atcagagccc ccgcagcttt caaaagaaaa cacgacacta    4740
ttttattgct gcagtggaga ggctctggga ttatgggatg agtagctccc acatgttct    4800 aagaaacagg gctcagagtg gcagtgtccc tcagttcaag aaagttgttt tccaggaatt    4860
tactgatggc tcctttactc agcccttata ccgtggagaa ctaaatgaac atttgggact    4920
cctggggcca tatataagag cagaagttga agataatatc atggtaactt tcagaaatca    4980
ggcctctcgt ccctattcct tctattctag ccttatttct tatgaggaag atcagaggca    5040
aggagcagaa cctagaaaaa actttgtcaa gcctaatgaa accaaaactt acttttggaa    5100
agtgcaacat catatggcac ccactaaaga tgagtttgac tgcaaagcct gggcttattt    5160
ctctgatgtt gacctggaaa agatgtgca ctcaggcctg attggacccc ttctggtctg    5220
ccacactaac acactgaacc ctgctcatgg gagacaagtg acagtacagg aatttgctct    5280 gttttttcacc atctttgatg agaccaaaag ctggtacttc actgaaaata tggaaagaaa    5340
ctgcagggct ccctgcaata tccagatgga agatcccact tttaaagaga attatcgctt    5400
ccatgcaatc aatggctaca taatggatac actacctggc ttagtaatgg ctcaggatca    5460
aaggattcga tggtatctgc tcagcatggg cagcaatgaa acatccatt ctattcattt    5520 cagtggacat gtgttcactg tacgaaaaaa agaggagtat aaaatggcac tgtacaatct    5580
ctatccaggt gttttttgaga cagtggaaat gttaccatcc aaagctggaa tttggcgggt    5640
ggaatgcctt attggcgagc atctacatgc tgggatgagc acttttttc tggtgtacag    5700 caataagtgt cagactcccc tgggaatggc ttctggacac attagagatt tcagattac    5760 agcttcagga caatatggac agtgggcccc aaagctggcc agacttcatt attccggatc    5820
aatcaatgcc tggagcacca aggagcccctt ttcttggatc aaggtggatc tgttggcacc    5880
aatgattatt cacggcatca agacccaggg tgcccgtcag aagttctcca gcctctacat    5940
ctctcagttt atcatcatgt atagtcttga tgggaagaag tggcagactt atcgaggaaa    6000
ttccactgga accttaatgg tcttctttgg caatgtggat tcatctggga taaaacacaa    6060 tattttttaac cctccaatta ttgctcgata catccgtttg cacccaactc attatagcat    6120
tcgcagcact cttcgcatgg agttgatggg ctgtgattta aatagttgca gcatgccatt    6180
gggaatggag agtaaagcaa tatcagatgc acagattact gcttcatcct actttaccaa    6240
tatgtttgcc acctggtctc cttcaaaagc tcgacttcac ctccaaggga ggagtaatgc    6300
ctggagacct caggtgaata tccaaaaga gtggctgcaa gtggacttcc agaagacaat    6360
gaaagtcaca ggagtaacta ctcagggagt aaaatctctg cttaccagca tgtatgtgaa    6420
ggagttcctc atctccagca gtcaagatgg ccatcagtgg actctctttt ttcagaatgg    6480
caaagtaaag gttttttcagg gaaatcaaga ctccttcaca cctgtggtga actctctaga    6540
cccaccgtta ctgactcgct accttcgaat tcacccccag agttgggtgc accagattgc    6600
cctgaggatg gaggttctgg gctgcgaggc acaggacctc tactgacaat tgacgctgat    6660
cagcctcgac tgtgccttct agttgccagc catctgttgt ttgcccctcc ccgtgccttt    6720
ccttgaccct ggaaggtgcc actcccactg tcctttccta ataaaatgag gaaattgcat    6780
```

```
cgcattgtct gagtaggtgt cattctattc tggggggtgg ggtggggcag gacagcaagg    6840
gggaggattg ggaagacaat agcaggcatg ctggggagag atctaggaac ccctagtgat    6900
ggagttggcc actccctctc tgcgcgctcg ctcgctcact gaggccgccc gggcaaagcc    6960
cgggcgtcgg gcgacctttg gtcgcccggc ctcagtgagc gagcgagcgc gcagagaggg    7020
agtggccaac cccccccccc ccccccctgc aggcgattct cttgtttgct ccagactctc    7080
aggcaatgac ctgatagcct ttgtagagac ctctcaaaaa tagctaccct ctccggcatg    7140
aatttatcag ctagaacggt tgaatatcat attgatggtg atttgactgt ctccggcctt    7200
tctcacccgt ttgaatcttt acctacacat tactcaggca ttgcatttaa aatatatgag    7260
ggttctaaaa attttatcc ttgcgttgaa ataaaggctt ctcccgcaaa agtattacag     7320
ggtcataatg ttttggtac aaccgattta gctttatgct ctgaggcttt attgcttaat     7380
tttgctaatt ctttgccttg cctgtatgat ttattggatg ttggaattcc tgatgcggta    7440
ttttctcctt acgcatcgt gcggtatttc acaccgcata tggtgcactc tcagtacaat     7500
ctgctctgat gccgcatagt taagccagcc ccgacacccg ccaacacccg ctgacgcgcc    7560
ctgacgggct tgtctgctcc cggcatccgc ttacagacaa gctgtgaccg tctccgggag    7620
ctgcatgtgt cagaggtttt caccgtcatc accgaaacgc gcgagacgaa agggcctcgt    7680
gatacgccta ttttttatagg ttaatgtcat gataataatg gtttcttaga cgtcaggtgg   7740
cacttttcgg ggaaatgtgc gcggaacccc tatttgttta tttttctaaa tacattcaaa    7800
tatgtatccg ctcatgagac aataaccctg ataaatgctt caataatatt gaaaaaggaa    7860
gagtatgagt attcaacatt tccgtgtcgc ccttattccc ttttttgcgg cattttgcct    7920
tcctgttttt gctcacccag aaacgctggt gaaagtaaaa gatgctgaag atcagttggg    7980
tgcacgagtg ggttacatcg aactggatct caacagcggt aagatccttg agagttttcg    8040
ccccgaagaa cgttttccaa tgatgagcac ttttaaagtt ctgctatgtg gcgcggtatt    8100
atcccgtatt gacgccgggc aagagcaact cggtcgccgc atacactatt ctcagaatga    8160
cttggttgag tactcaccag tcacagaaaa gcatcttacg gatggcatga cagtaagaga    8220
attatgcagt gctgccataa ccatgagtga taacactgcg ccaacttac ttctgacaac     8280
gatcggagga ccgaaggagc taaccgcttt tttgcacaac atgggggatc atgtaactcg    8340
ccttgatcgt tgggaaccgg agctgaatga agccatacca aacgacgagc gtgacaccac    8400
gatgcctgta gcaatggcaa caacgttgcg caaactatta actggcgaac tacttactct    8460
agcttcccgg caacaattaa tagactggat ggaggcggat aaagttgcag gaccacttct    8520
gcgctcggcc cttccggctg gctggtttat tgctgataaa tctggagccg gtgagcgtgg    8580
gtctcgcggt atcattgcag cactggggcc agatggtaag ccctcccgta tcgtagttat    8640
ctacacgacg gggagtcagg caactatgga tgaacgaaat agacagatcg ctgagatagg    8700
tgcctcactg attaagcatt ggtaactgtc agaccaagtt tactcatata ctttagat     8760
tgatttaaaa cttcattttt aatttaaaag gatctaggtg aagatccttt ttgataatct    8820
catgaccaaa atcccttaac gtgagttttc gttccactga gcgtcagacc ccgtagaaaa    8880
gatcaaagga tcttcttgag atcctttttt tctgcgcgta atctgctgct tgcaaacaaa    8940
aaaaccaccg ctaccagcgg tggtttgttt gccggatcaa gagctaccaa ctctttttcc    9000
gaaggtaact ggcttcagca gagcgcagat accaaatact gtccttctag tgtagccgta    9060
gttaggccac cacttcaaga actctgtagc accgcctaca tacctcgctc tgctaatcct    9120
gttaccagtg gctgctgcca gtggcgataa gtcgtgtctt accgggttgg actcaagacg    9180
```

```
atagttaccg gataaggcgc agcggtcggg ctgaacgggg ggttcgtgca cacagcccag   9240
cttggagcga acgacctaca ccgaactgag atacctacag cgtgagctat gagaaagcgc   9300
cacgcttccc gaagggagaa aggcggacag gtatccggta agcggcaggg tcggaacagg   9360
agagcgcacg agggagcttc caggggggaaa cgcctggtat ctttatagtc ctgtcgggtt   9420
tcgccacctc tgacttgagc gtcgattttt gtgatgctcg tcagggggggc ggagcctatg   9480 gaaaaacgcc agcaacgcgg ccttttttacg gttcctggcc ttttgctggc cttttgctca   9540
catgttcttt cctgcgttat cccctgattc tgtggataac cgtattaccg cctttgagtg   9600
agctgatacc gctcgccgca gccgaacgac cgagcgcagc gagtcagtga gcgaggaagc   9660
ggaagagcgc ccaatacgca aaccgcctct ccccgcgcgt tggccgattc attaatgcag   9720
```

<210> SEQ ID NO 5
<211> LENGTH: 7757
<212> TYPE: DNA
<213> ORGANISM: Artificial Sequence
<220> FEATURE:
<223> OTHER INFORMATION: pAAV-CB-hHC1690-X10

<400> SEQUENCE: 5

```
aattcccatc atcaataata taccttattt tggattgaag ccaatatgat aatgaggggg     60
tggagtttgt gacgtggcgc ggggcgtggg aacggggcgg gtgacgtagt agtctctaga    120
ggtccccagc gaccttgacg ggcatctgcc cggcatttct gacagctttg tgaactgggt    180
ggccgagaag gaatgggagt tgccgccaga ttctgacatg gatctgaatc tgattgagca    240
ggcacccctg accgtggccg agaagctgca tcgctggcgt aatagcgaag aggcccgcac    300
cgatcgccct tcccaacagt tgcgcagcct gaatggcgaa tggaattcca gacgattgag    360
cgtcaaaatg taggtatttc catgagcgtt tttcctgttg caatggctgg cggtaatatt    420
gttctggata ttaccagcaa ggccgatagt ttgagttctt ctactcaggc aagtgatgtt    480
attactaatc aaagaagtat tgcgacaacg gttaatttgc gtgatggaca gactcttttta    540 ctcggtggcc tcactgatta taaaaacact tctcaggatt ctggcgtacc gttcctgtct    600
aaaatccctt taatcggcct cctgtttagc tcccgctctg attctaacga ggaaagcacg    660
ttatacgtgc tcgtcaaagc aaccatagta cgcgccctgt agcggcgcat taagcgcggc    720
gggtgtggtg gttacgcgca gcgtgaccgc tacacttgcc agcgccctag cgcccgctcc    780
tttcgctttc ttcccttcct ttctcgccac gttcgccggc tttccccgtc aagctctaaa    840
tcgggggctc cctttagggt tccgatttag tgctttacgg cacctcgacc ccaaaaaact    900
tgattagggt gatggttcac gtagtgggcc atcgccctga tagacggttt ttcgcccttt    960
gacgttggag tccacgttct ttaatagtgg actcttgttc caaactggaa caacactcaa   1020
ccctatctcg gtctattctt ttgatttata agggattttg ccgatttcgg cctattggtt   1080
aaaaaatgag ctgatttaac aaaaatttaa cgcgaatttt aacaaaatat taacgtttac   1140
aatttaaata tttgcttata caatcttcct gttttttgggg cttttctgat tatcaaccgg   1200
ggtacatatg attgacatgc tagttttacg attaccgttc atcgcctgca ggggggggggg   1260 ggggggggtt ggccactccc tctctgcgcg ctcgctcgct cactgaggcc gggcgaccaa   1320
aggtcgcccg acgcccgggc tttgcccggg cggcctcagt gagcgagcga gcgcgcagag   1380
agggagtggc caactccatc actaggggtt cctagatctg aattcggtac gtacctctgg   1440
tcgttacata acttacggta aatggcccgc ctggctgacc gcccaacgac cccgcccatt   1500
```

```
gacgtcaata atgacgtatg ttcccatagt aacgccaata gggactttcc attgacgtca    1560
atgggtggag tatttacggt aaactgccca cttggcagta catcaagtgt atcatatgcc    1620
aagtacgccc cctattgacg tcaatgacgg taaatggccc gcctggcatt atgcccagta    1680
catgacctta tgggactttc ctacttggca gtacatctac tcgaggccac gttctgcttc    1740
actctcccca tctcccccc ctccccaccc ccaattttgt atttatttat tttttaatta    1800
ttttgtgcag cgatggggc ggggggggggg gggggggggg cgcgcgccag cggggcggg    1860 gcgggcgag gggcggggcg gggcgaggcg gagaggtgcg gcgcagcca atcagagcgg    1920 cgcgctccga aagtttcctt ttatggcgag cggcggcgg cggcggccct ataaaaagcg    1980
aagcgcgcgg cgggcgggag cgggatcagc caccgcggtg gcggcctaga gtcgacgagg    2040
aactgaaaaa ccagaaagtt aactggtaag tttagtcttt ttgtctttta tttcaggtcc    2100
cggatccggt ggtggtgcaa atcaaagaac tgctcctcag tggatgttgc ctttacttct    2160
aggcctgtac ggaagtgtta cttctgctct aaaagctgcg gaattgtacc cgcggccgct    2220
tttcaaaatg caaatagagc tctccacctg cttctttctg tgccttttgc gattctgctt    2280
tagtgccacc agaagatact acctgggtgc agtggaactg tcatgggact atatgcaaag    2340
tgatctcggt gagctgcctg tggacgcaag atttcctcct agagtgccaa atcttttcc    2400 attcaacacc tcagtcgtgt acaaaaagac tctgtttgta gaattcacgg atcaccttt    2460 caacatcgct aagccaaggc caccctggat gggtctgcta ggtcctacca tccaggctga    2520
ggtttacgac acgtggtcg ttaccctgaa gaacatggct tctcatcccg ttagtcttca    2580
cgctgtcggc gtctccttct ggaaatcttc cgaaggcgct gaatatgagg atcacaccag    2640 ccaagggag aaggaagacg ataaagtcct tcccggtaaa agccaaacct acgtctggca    2700
ggtcctgaaa gaaaatggtc caacagcctc tgacccacca tgtcttacct actcataccc    2760
gtctcacgtg gacctggtga agacctgaa ttcgggcctc attggagccc tactagtatg    2820
tagagaaggg agtctggcca aggaaaagac acagaccttg cacaaattta tactactttt    2880
tgctgtattt gatgaaggga aaagttggca ctcagaaaca agaactcct tgatgcagga    2940 tagggatgct gcatctgctc gggcctggcc taaaatgcac acagtcaatg gttatgtaaa    3000
caggtctctg ccaggtctga ttggatgcca caggaaatca gtctattggc atgtgattgg    3060
aatgggcacc actcctgaag tgcactcaat attcctcgaa ggtcacacat tcttgtgag    3120 gaaccatcgc caggcgtcct tggaaatctc gccaataact ttccttactg ctcaaacact    3180
cttgatggac cttggacagt ttctactgtt ttgtcatatc tcttcccacc aacatgatgg    3240
catggaagct tatgtcaaag tagacagctg tccagaggaa ccccaactac gaatgaaaaa    3300
taatgaagaa gcggaagact atgatgatga tcttactgat tctgaaatgg atgtggtcag    3360
gtttgatgat gacaactctc cttcctttat ccaaattcgc tcagttgcca agaagcatcc    3420
taaaacttgg gtacattaca ttgctgctga agaggaggac tgggactatg ctcccttagt    3480
cctcgccccc gatgacagaa gttataaaag tcaatatttg aacaatggcc ctcagcggat    3540
tggtaggaag tacaaaaaag tccgatttat ggcatacaca gatgaaacct taagactcg    3600 tgaagctatt cagcatgaat caggaatctt gggacccttta ctttatgggg aagttggaga    3660
cacactgttg attatattta agaatcaagc aagcagacca tataacatct accctcacgg    3720
aatcactgat gtccgtccct tgtattcaag gagattacca aaaggtgtaa acatttgaa    3780 ggattttcca attctgccag gagaaatatt caaatataaa tggacagtga ctgtagaaga    3840
tgggccaact aaatcagatc ctcggtgcct gacccgctat tactctagtt tcgttaatat    3900
```

```
ggagagagat ctagcttcag gactcattgg ccctctcctc atctgctaca aagaatctgt    3960
agatcaaaga ggaaaccaga taatgtcaga caagaggaat gtcatcctgt tttctgtatt    4020
tgatgagaac cgaagctggt acctcacaga gaatatacaa cgctttctcc ccaatccagc    4080
tggagtgcag cttgaggatc cagagttcca agcctccaac atcatgcaca gcatcaatgg    4140
ctatgttttt gatagtttgc agttgtcagt ttgtttgcat gaggtggcat actggtacat    4200
tctaagcatt ggagcacaga ctgacttcct ttctgtcttc ttctctggat ataccttcaa    4260
acacaaaatg gtctatgaag acacactcac cctattccca ttctcaggag aaactgtctt    4320
catgtcgatg gaaaacccag gtctatggat tctggggtgc cacaactcag actttcggaa    4380
cagaggcatg accgccttac tgaaggtttc tagttgtgac aagaacactg gtgattatta    4440
cgaggacagt tatgaagata tttcagcata cttgctgagt aaaaacaatg ccattgaacc    4500
aagaagcttc tcccagaatc caccagtctt gaaacgccat caacgcgaaa taactcgtac    4560
tactcttcag tcagatcaag aggaaattga ctatgatgat accatatcag ttgaaatgaa    4620
gaaggaagat tttgacattt atgatgagga tgaaaatcag agcccccgca gctagcaatt    4680
gtagtctgaa cgctgatcag cctcgactgt gccttctagt tgccagccat ctgttgtttg    4740 cccctcccc gtgccttcct tgaccctgga aggtgccact cccactgtcc tttcctaata    4800
aaatgaggaa attgcatcgc attgtctgag taggtgtcat tctattctgg ggggtggggt    4860
ggggcaggac agcaaggggg aggattggga agacaatagc aggcatgctg gggagagatc    4920 taggaaccc tagtgatgga gttggccact ccctctctgc gcgctcgctc gctcactgag    4980
gccgcccggg caaagcccgg gcgtcgggcg acctttggtc gcccggcctc agtgagcgag    5040
cgagcgcgca gagagggagt ggccaacccc cccccccc cccctgcagg cgattctctt    5100
gtttgctcca gactctcagg caatgacctg atagcctttg tagagacctc tcaaaaatag    5160
ctaccctctc cggcatgaat ttatcagcta gaacggttga atatcatatt gatggtgatt    5220
tgactgtctc cggccttcct cacccgtttg aatctttacc tacacattac tcaggcattg    5280
catttaaaat atatgagggt tctaaaaatt tttatccttg cgttgaaata aaggcttctc    5340
ccgcaaaagt attacagggt cataatgttt ttggtacaac cgatttagct ttatgctctg    5400
aggctttatt gcttaatttt gctaattctt tgccttgcct gtatgattta ttggatgttg    5460
gaattcctga tgcggtattt tctccttacg catctgtgcg gtatttcaca ccgcatatgg    5520
tgcactctca gtacaatctg ctctgatgcc gcatagttaa gccagccccg acacccgcca    5580
acacccgctg acgcgccctg acgggcttgt ctgctcccgg catccgctta cagacaagct    5640
gtgaccgtct ccgggagctg catgtgtcag aggttttcac cgtcatcacc gaaacgcgcg    5700
agacgaaagg gcctcgtgat acgcctattt ttataggtta atgtcatgat aataatggtt    5760
tcttagacgt caggtggcac ttttcgggga atgtgcgcg gaacccctat ttgtttattt    5820
ttctaaatac attcaaatat gtatccgctc atgagacaat aaccctgata aatgcttcaa    5880
taatattgaa aaaggaagag tatgagtatt caacatttcc gtgtcgccct tattcccttt    5940
tttgcggcat tttgccttcc tgttttgct cacccagaaa cgctggtgaa agtaaaagat    6000
gctgaagatc agttgggtgc acgagtgggt tacatcgaac tggatctcaa cagcggtaag    6060
atccttgaga gttttcgccc cgaagaacgt tttccaatga tgagcacttt taaagttctg    6120
ctatgtggcg cggtattatc ccgtattgac gccgggcaag agcaactcgg tcgccgcata    6180
cactattctc agaatgactt ggttgagtac tcaccagtca cagaaaagca tcttacggat    6240
```

-continued

```
ggcatgacag taagagaatt atgcagtgct gccataacca tgagtgataa cactgcggcc      6300
aacttacttc tgacaacgat cggaggaccg aaggagctaa ccgcttttt  gcacaacatg      6360 ggggatcatg taactcgcct tgatcgttgg gaaccggagc tgaatgaagc cataccaaac      6420
gacgagcgtg acaccacgat gcctgtagca atggcaacaa cgttgcgcaa actattaact      6480
ggcgaactac ttactctagc ttcccggcaa caattaatag actggatgga ggcggataaa      6540
gttgcaggac cacttctgcg ctcggccctt ccggctggct ggtttattgc tgataaatct      6600
ggagccggtg agcgtgggtc tcgcggtatc attgcagcac tggggccaga tggtaagccc      6660
tcccgtatcg tagttatcta cacgacgggg agtcaggcaa ctatgatga  acgaaataga      6720 cagatcgctg agataggtgc ctcactgatt aagcattggt aactgtcaga ccaagtttac      6780
tcatatatac tttagattga tttaaaactt cattttta at ttaaaggat ctaggtgaag      6840 atcctttttg ataatctcat gaccaaaatc ccttaacgtg agttttcgtt ccactgagcg      6900
tcagaccccg tagaaaagat caaaggatct tcttgagatc ctttttttct gcgcgtaatc      6960
tgctgcttgc aaacaaaaaa accaccgcta ccagcggtgg tttgtttgcc ggatcaagag      7020
ctaccaactc tttttccgaa ggtaactggc ttcagcagag cgcagatacc aaatactgtc      7080
cttctagtgt agccgtagtt aggccaccac ttcaagaact ctgtagcacc gcctacatac      7140
ctcgctctgc taatcctgtt accagtggct gctgccagtg gcgataagtc gtgtcttacc      7200
gggttggact caagacgata gttaccggat aaggcgcagc ggtcgggctg aacggggggt      7260
tcgtgcacac agcccagctt ggagcgaacg acctacaccg aactgagata cctacagcgt      7320
gagctatgag aaagcgccac gcttcccgaa gggagaaagg cggacaggta tccggtaagc      7380
ggcagggtcg gaacaggaga gcgcacgagg gagcttccag ggggaaacgc ctggtatctt      7440
tatagtcctg tcgggtttcg ccacctctga cttgagcgtc gatttttgtg atgctcgtca      7500
ggggggcgga gcctatggaa aaacgccagc aacgcggcct ttttacggtt cctggccttt      7560
tgctggcctt tgctcacat  gttctttcct gcgttatccc ctgattctgt ggataaccgt      7620
attaccgcct ttgagtgagc tgataccgct cgccgcagcc gaacgaccga gcgcagcgag      7680
tcagtgagcg aggaagcgga agagcgccca atacgcaaac cgcctctccc cgcgcgttgg      7740
ccgattcatt aatgcag                                                    7757
```

<210> SEQ ID NO 6
<211> LENGTH: 7757
<212> TYPE: DNA
<213> ORGANISM: Artificial Sequence
<220> FEATURE:
<223> OTHER INFORMATION: pAAV-CB-hHC1690-X5

<400> SEQUENCE: 6

```
aattcccatc atcaataata taccttattt tggattgaag ccaatatgat aatgagggg       60 tggagtttgt gacgtggcgc ggggcgtggg aacgggcgg  gtgacgtagt agtctctaga      120
ggtccccagc gaccttgacg ggcatctgcc cggcatttct gacagctttg tgaactgggt      180
ggccgagaag gaatgggagt tgccgccaga ttctgacatg gatctgaatc tgattgagca      240
ggcacccctg accgtggccg agaagctgca tcgctgcgt  aatagcgaag aggcccgcac      300
cgatcgccct tcccaacagt tgcgcagcct gaatggcgaa tggaattcca gacgattgag      360
cgtcaaaatg taggtatttc catgagcgtt tttcctgttg caatggctgg cggtaatatt      420 gttctgata  ttaccagcaa ggccgatagt ttgagttctt ctactcaggc aagtgatgtt      480
attactaatc aaagaagtat tgcgacaacg gttaatttgc gtgatggaca gactcttta       540
```

```
ctcggtggcc tcactgatta taaaaacact tctcaggatt ctggcgtacc gttcctgtct      600
aaaatccctt taatcggcct cctgtttagc tcccgctctg attctaacga ggaaagcacg      660
ttatacgtgc tcgtcaaagc aaccatagta cgcgccctgt agcggcgcat taagcgcggc      720
gggtgtggtg gttacgcgca gcgtgaccgc tacacttgcc agcgccctag cgcccgctcc      780
tttcgctttc ttcccttcct ttctcgccac gttcgccggc tttccccgtc aagctctaaa      840 tcggggctc cctttagggt tccgatttag tgctttacgg cacctcgacc ccaaaaaact       900
tgattagggt gatggttcac gtagtgggcc atcgccctga tagacggttt tcgcccttt      960 gacgttggag tccacgttct ttaatagtgg actcttgttc caaactggaa caacactcaa     1020
ccctatctcg gtctattctt ttgatttata agggattttg ccgatttcgg cctattggtt     1080
aaaaaatgag ctgatttaac aaaaatttaa cgcgaatttt aacaaaatat taacgtttac     1140
aatttaaata tttgcttata caatcttcct gttttggggg cttttctgat tatcaaccgg     1200
ggtacatatg attgacatgc tagttttacg attaccgttc atcgcctgca gggggggggg     1260 gggggggggtt ggccactccc tctctgcgcg ctcgctcgct cactgaggcc gggcgaccaa    1320
aggtcgcccg acgcccgggc tttgcccggg cggcctcagt gagcgagcga gcgcgcagag     1380
agggagtggc caactccatc actaggggtt cctagatctg aattcggtac gtacctctgg     1440
tcgttacata acttacggta aatggcccgc ctggctgacc gcccaacgac cccgcccatt     1500
gacgtcaata atgacgtatg ttcccatagt aacgccaata gggactttcc attgacgtca     1560
atgggtggag tatttacggt aaactgccca cttggcagta catcaagtgt atcatatgcc     1620
aagtacgccc cctattgacg tcaatgacgg taaatggccc gcctggcatt atgcccagta     1680
catgacctta tgggactttc ctacttggca gtacatctac tcgaggccac gttctgcttc     1740
actctcccca tctcccccc ctcccacccc ccaatttgt atttatttat tttttaatta      1800
ttttgtgcag cgatggggc ggggggggg ggggggggg cgcgcgccag cggggcggg       1860 gcggggcgag gggcggggcg gggcgaggcg gagaggtgcg gcggcagcca atcagagcgg     1920
cgcgctccga aagtttcctt ttatggcgag gcggcggcgg cggcggccct ataaaaagcg     1980
aagcgcgcgg cgggcgggag cgggatcagc caccgcggtg gcggcctaga gtcgacgagg     2040
aactgaaaaa ccagaaagtt aactggtaag tttagtcttt ttgtctttta tttcaggtcc     2100
cggatccggt ggtggtgcaa atcaagaac tgctcctcag tggatgttgc ctttacttct      2160
aggcctgtac ggaagtgtta cttctgctct aaaagctgcg gaattgtacc cgcggccgct     2220
tttcaaaatg caaatagagc tctccacctg cttctttctg tgccttttgc gattctgctt     2280
tagtgccacc agaagatact acctgggtgc agtggaactg tcatgggact atatgcaaag     2340
tgatctcggt gagctgcctg tggacgcaag atttcctcct agagtgccaa aatcttttcc     2400
attcaacacc tcagtcgtgt acaaaaagac tctgtttgta gaattcacgg atcaccttt     2460 caacatcgct aagccaaggc caccctggat ggtctgcta ggtcctacca tccaggctga      2520
ggtttatgat acagtggtcg ttacacttaa gaacatggct tcccatcctg tcagtcttca     2580
tgctgttggt gtatcctact ggaaatcttc tgagggagct gaatatgatg atcagaccag     2640
tcaaaggagg aaagaagatg ataagtctt ccctggtaaa agccatacat atgtctggca     2700
ggtcctgaaa gagaatggtc caacagcctc tgacccacca tgccttacct actcatatct     2760
ttctcatgtg gacctggtaa aagacttgaa ttcaggcctc attggagccc tactagtatg     2820
tagagaaggg agtctggcca aggaaaagac acagaccttg cacaaattta tactactttt     2880
```

```
tgctgtattt gatgaaggga aaagttggca ctcagaaaca agaactcct tgatgcagga    2940 tagggatgct gcatctgctc gggcctggcc taaaatgcac acagtcaatg gttatgtaaa   3000
caggtctctg ccaggtctga ttggatgcca caggaaatca gtctattggc atgtgattgg   3060
aatgggcacc actcctgaag tgcactcaat attcctcgaa ggtcacacat tcttgtgag    3120 gaaccatcgc caggcgtcct tggaaatctc gccataact tccttactg ctcaaacact    3180 cttgatggac cttggacagt ttctactgtt ttgtcatatc tcttcccacc aacatgatgg   3240
catggaagct tatgtcaaag tagacagctg tccagaggaa ccccaactac gaatgaaaaa   3300
taatgaagaa gcggaagact atgatgatga tcttactgat tctgaaatgg atgtggtcag   3360
gtttgatgat gacaactctc cttcctttat ccaaattcgc tcagttgcca agaagcatcc   3420
taaaacttgg gtacattaca ttgctgctga agaggaggac tgggactatg ctcccttagt   3480
cctcgccccc gatgacagaa gttataaaag tcaatatttg aacaatggcc ctcagcggat   3540
tggtaggaag tacaaaaaag tccgatttat ggcatacaca gatgaaacct ttaagactcg   3600
tgaagctatt cagcatgaat caggaatctt gggaccttta ctttatgggg aagttggaga   3660
cacactgttg attatattta agaatcaagc aagcagacca tataacatct accctcacgg   3720
aatcactgat gtccgtcctt tgtattcaag agattacca aaaggtgtaa acatttgaa    3780 ggattttcca attctgccag agaaatatt caaatataaa tggacagtga ctgtagaaga   3840
tgggccaact aaatcagatc ctcggtgcct gacccgctat tactctagtt tcgttaatat   3900
ggagagagat ctagcttcag gactcattgg ccctctcctc atctgctaca agaatctgt    3960 agatcaaaga ggaaaccaga taatgtcaga caagaggaat gtcatcctgt tttctgtatt   4020
tgatgagaac cgaagctggt acctcacaga gaatatacaa cgctttctcc ccaatccagc   4080
tggagtgcag cttgaggatc cagagttcca agcctccaac atcatgcaca gcatcaatgg   4140
ctatgttttt gatagtttgc agttgtcagt ttgtttgcat gaggtggcat actggtacat   4200
tctaagcatt ggagcacaga ctgacttcct ttctgtcttc ttctctggat ataccttcaa   4260
acacaaaatg gtctatgaag acacactcac cctattccca ttctcaggag aaactgtctt   4320
catgtcgatg gaaaacccag gtctatggat tctggggtgc cacaactcag actttcggaa   4380
cagaggcatg accgccttac tgaaggtttc tagttgtgac aagaacactg gtgattatta   4440
cgaggacagt tatgaagata tttcagcata cttgctgagt aaaaacaatg ccattgaacc   4500
aagaagcttc tcccagaatc accagtctt gaaacgccat caacgcgaaa taactcgtac    4560
tactcttcag tcagatcaag aggaaattga ctatgatgat accatatcag ttgaaatgaa   4620
gaaggaagat tttgacattt atgatgagga tgaaaatcag agccccgca gctagcaatt    4680 gtagtctgaa cgctgatcag cctcgactgt gccttctagt tgccagccat ctgttgtttg   4740
cccctccccc gtgccttcct tgaccctgga aggtgccact cccactgtcc tttcctaata   4800
aaatgaggaa attgcatcgc attgtctgag taggtgtcat tctattctgg ggggtggggt   4860
ggggcaggac agcaaggggg aggattggga agacaatagc aggcatgctg gggagagatc   4920 taggaaccccc tagtgatgga gttggccact ccctctctgc gcgctcgctc gctcactgag   4980
gccgcccggg caaagcccgg gcgtcgggcg acctttggtc gcccggcctc agtgagcgag   5040
cgagcgcgca gagagggagt ggccaacccc cccccccccc ccctgcagg cgattctctt    5100 gtttgctcca gactctcagg caatgacctg atagcctttg tagagacctc tcaaaaatag   5160
ctaccctctc cggcatgaat ttatcagcta gaacggttga atatcatatt gatggtgatt   5220
tgactgtctc cggcctttct cacccgtttg aatctttacc tacacattac tcaggcattg   5280
```

```
catttaaaat atatgagggt tctaaaaatt tttatccttg cgttgaaata aaggcttctc   5340
ccgcaaaagt attacagggt cataatgttt ttggtacaac cgatttagct ttatgctctg   5400
aggctttatt gcttaatttt gctaattctt tgccttgcct gtatgattta ttggatgttg   5460
gaattcctga tgcggtattt tctccttacg catctgtgcg gtatttcaca ccgcatatgg   5520
tgcactctca gtacaatctg ctctgatgcc gcatagttaa gccagccccg acacccgcca   5580
acaccgctg acgcgccctg acgggcttgt ctgctcccgg catccgctta cagacaagct   5640
gtgaccgtct ccgggagctg catgtgtcag aggttttcac cgtcatcacc gaaacgcgcg   5700
agacgaaagg gcctcgtgat acgcctattt ttataggtta atgtcatgat aataatggtt   5760
tcttagacgt caggtggcac ttttcgggga atgtgcgcg gaacccctat tgtttatttt   5820
ttctaaatac attcaaatat gtatccgctc atgagacaat aaccctgata aatgcttcaa   5880
taatattgaa aaggaagag tatgagtatt caacatttcc gtgtcgccct tattccctt    5940
tttgcggcat tttgccttcc tgtttttgct cacccagaaa cgctggtgaa agtaaaagat   6000
gctgaagatc agttgggtgc acgagtgggt tacatcgaac tggatctcaa cagcggtaag   6060
atccttgaga gttttcgccc cgaagaacgt tttccaatga tgagcacttt taaagttctg   6120
ctatgtggcg cggtattatc ccgtattgac gccgggcaag agcaactcgg tcgccgcata   6180
cactattctc agaatgactt ggttgagtac tcaccagtca cagaaaagca tcttacggat   6240
ggcatgacag taagagaatt atgcagtgct gccataacca tgagtgataa cactgcggcc   6300
aacttacttc tgacaacgat cggaggaccg aaggagctaa ccgcttttt gcacaacatg   6360
ggggatcatg taactcgcct tgatcgttgg gaaccggagc tgaatgaagc cataccaaac   6420
gacgagcgtg acaccacgat gcctgtagca atggcaacaa cgttgcgcaa actattaact   6480
ggcgaactac ttactctagc ttcccggcaa caattaatag actggatgga ggcggataaa   6540
gttgcaggac cacttctgcg ctcggccctt ccggctggct ggtttattgc tgataaatct   6600
ggagccggtg agcgtgggtc tcgcggtatc attgcagcac tggggccaga tggtaagccc   6660
tcccgtatcg tagttatcta cacgacgggg agtcaggcaa ctatggatga acgaaataga   6720
cagatcgctg agataggtgc ctcactgatt aagcattggt aactgtcaga ccaagtttac   6780
tcatatatac tttagattga tttaaaactt catttttaat ttaaaaggat ctaggtgaag   6840
atcctttttg ataatctcat gaccaaaatc ccttaacgtg agttttcgtt ccactgagcg   6900
tcagaccccg tagaaaagat caaaggatct tcttgagatc cttttttct gcgcgtaatc   6960
tgctgcttgc aaacaaaaaa accaccgcta ccagcggtgg tttgtttgcc ggatcaagag   7020
ctaccaactc tttttccgaa ggtaactggc ttcagcagag cgcagatacc aaatactgtc   7080
cttctagtgt agccgtagtt aggccaccac ttcaagaact ctgtagcacc gcctacatac   7140
ctcgctctgc taatcctgtt accagtggct gctgccagtg gcgataagtc gtgtcttacc   7200
gggttggact caagacgata gttaccggat aaggcgcagc ggtcgggctg aacggggggt   7260
tcgtgcacac agcccagctt ggagcgaacg acctacaccg aactgagata cctacagcgt   7320
gagctatgag aaagcgccac gcttcccgaa gggagaaagg cggacaggta tccggtaagc   7380
ggcagggtcg gaacaggaga gcgcacgagg gagcttccag ggggaaacgc ctggtatctt   7440
tatagtcctg tcgggtttcg ccacctctga cttgagcgtc gatttttgtg atgctcgtca   7500
ggggggcgga gcctatggaa aaacgccagc aacgcggcct ttttacggtt cctggccttt   7560
tgctggcctt ttgctcacat gttctttcct gcgttatccc ctgattctgt ggataaccgt   7620
```

```
attaccgcct ttgagtgagc tgataccgct cgccgcagcc gaacgaccga gcgcagcgag    7680
tcagtgagcg aggaagcgga agagcgccca atacgcaaac cgcctctccc cgcgcgttgg    7740
ccgattcatt aatgcag                                                   7757
```

<210> SEQ ID NO 7
<211> LENGTH: 200
<212> TYPE: PRT
<213> ORGANISM: Homo sapiens

<400> SEQUENCE: 7

```
Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala
        195                 200
```

<210> SEQ ID NO 8
<211> LENGTH: 200
<212> TYPE: PRT
<213> ORGANISM: Homo sapiens

<400> SEQUENCE: 8

```
Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Val Thr Leu Lys Asn Met Ala Ser His Pro Val
                85                  90                  95
```

```
Ser Leu His Ala Val Gly Val Ser Phe Trp Lys Ser Ser Glu Gly Ala
            100                 105                 110

Glu Tyr Glu Asp His Thr Ser Gln Arg Glu Lys Glu Asp Asp Lys Val
        115                 120                 125

Leu Pro Gly Lys Ser Gln Thr Tyr Val Trp Gln Val Leu Lys Glu Asn
    130                 135                 140

Gly Pro Thr Ala Ser Asp Pro Pro Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala
        195                 200

<210> SEQ ID NO 9
<211> LENGTH: 200
<212> TYPE: PRT
<213> ORGANISM: Homo sapiens

<400> SEQUENCE: 9

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Thr Leu Lys Asn Met Ala Ser His Pro Val
                85                  90                  95

Ser Leu His Ala Val Gly Val Ser Tyr Trp Lys Ser Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Lys Ser His Thr Tyr Val Trp Gln Val Leu Lys Glu Asn
    130                 135                 140

Gly Pro Thr Ala Ser Asp Pro Pro Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala
        195                 200
```